(12) United States Patent
Salituro et al.

(10) Patent No.: US 9,938,259 B2
(45) Date of Patent: *Apr. 10, 2018

(54) THERAPEUTIC COMPOSITIONS AND RELATED METHODS OF USE

(71) Applicant: Agios Pharmaceuticals, Inc., Cambridge, MA (US)

(72) Inventors: Francesco G. Salituro, Marlborough, MA (US); Jeffrey O. Saunders, Lincoln, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/488,174

(22) Filed: Apr. 14, 2017

(65) Prior Publication Data
US 2017/0283401 A1 Oct. 5, 2017

Related U.S. Application Data

(60) Division of application No. 14/836,330, filed on Aug. 26, 2015, now Pat. No. 9,657,004, which is a continuation of application No. 14/277,957, filed on May 15, 2014, now abandoned, which is a division of application No. 13/267,494, filed on Oct. 6, 2011, now Pat. No. 8,742,119, which is a continuation of application No. PCT/US2010/030139, filed on Apr. 6, 2010.

(60) Provisional application No. 61/233,470, filed on Aug. 12, 2009, provisional application No. 61/167,017, filed on Apr. 6, 2009.

(51) Int. Cl.
*A61K 31/506* (2006.01)
*C07D 405/14* (2006.01)
*C07D 401/04* (2006.01)
*C07D 403/04* (2006.01)
*C07D 417/04* (2006.01)
*C07D 409/04* (2006.01)

(52) U.S. Cl.
CPC ......... *C07D 405/14* (2013.01); *C07D 401/04* (2013.01); *C07D 403/04* (2013.01); *C07D 409/04* (2013.01); *C07D 417/04* (2013.01)

(58) Field of Classification Search
CPC .. C07D 405/14; C07D 401/04; C07D 403/04; C07D 409/04; C07D 417/04
See application file for complete search history.

(56) References Cited

U.S. PATENT DOCUMENTS

| | | | |
|---|---|---|---|
| 3,046,122 A | 7/1962 | Siis et al. | |
| 3,097,210 A | 7/1963 | Bicking | |
| 3,998,828 A | 12/1976 | Wiedermann | |
| 4,235,871 A | 11/1980 | Papahadjopoulos et al. | |
| 4,315,940 A | 2/1982 | Hitzel et al. | |
| 4,474,599 A | 10/1984 | Rogers et al. | |
| 4,501,728 A | 2/1985 | Geho et al. | |
| 4,591,548 A | 5/1986 | Delprato | |
| 4,593,102 A | 6/1986 | Shanklin, Jr. | |
| 4,775,762 A | 10/1988 | Knox et al. | |
| 4,837,028 A | 6/1989 | Allen | |
| 4,849,424 A | 7/1989 | Ikeda et al. | |
| 4,881,965 A | 11/1989 | Yamamoto et al. | |
| 4,889,553 A | 12/1989 | Rowson et al. | |
| 4,959,094 A | 9/1990 | Wegner et al. | |
| 5,019,369 A | 5/1991 | Presant et al. | |
| 5,094,682 A | 3/1992 | Tarara et al. | |
| 5,122,530 A | 6/1992 | Tomioka et al. | |
| 5,180,732 A | 1/1993 | Tomioka et al. | |
| 5,220,028 A | 6/1993 | Iwasawa et al. | |
| 5,252,590 A | 10/1993 | Tomioka et al. | |
| 5,484,760 A * | 1/1996 | Bussler .................. | A01N 25/32 504/103 |
| 5,556,866 A | 9/1996 | Aga et al. | |
| 5,834,485 A | 11/1998 | Dyke et al. | |
| 5,962,490 A | 10/1999 | Chan et al. | |
| 5,965,559 A | 10/1999 | Faull et al. | |
| 5,965,569 A | 10/1999 | Camps Garcia et al. | |
| 6,020,357 A | 2/2000 | Pinto et al. | |
| 6,106,849 A | 8/2000 | Malkan et al. | |
| 6,150,356 A | 11/2000 | Lloyd et al. | |
| 6,172,005 B1 | 1/2001 | Selby | |
| 6,265,588 B1 | 7/2001 | Mullner et al. | |
| 6,313,127 B1 | 11/2001 | Waterson et al. | |
| 6,492,368 B1 | 12/2002 | Dorsch et al. | |
| 6,511,977 B1 | 1/2003 | Lloyd et al. | |
| 6,818,631 B1 | 11/2004 | Nakagawa et al. | |
| 7,173,025 B1 | 2/2007 | Stocker et al. | |
| 7,288,554 B2 | 10/2007 | Finkelstein et al. | |
| 7,524,848 B2 | 4/2009 | Powers et al. | |

(Continued)

FOREIGN PATENT DOCUMENTS

| | | |
|---|---|---|
| AU | 2008345225 A1 | 7/2009 |
| CA | 2235621 A1 | 5/1997 |
| CA | 2709784 A1 | 7/2009 |
| CN | 101296909 A | 10/2008 |
| DE | 3813886 A1 | 11/1989 |
| DE | 19841985 A1 | 3/2000 |
| EP | 0189069 A2 | 7/1986 |
| EP | 0246749 A2 | 11/1987 |
| EP | 0628551 A1 | 12/1994 |
| EP | 1586558 A2 | 10/2005 |
| EP | 2219646 A2 | 8/2010 |
| EP | 2417123 A2 | 2/2012 |
| FR | 2735127 A1 | 12/1996 |
| GB | 1274436 A | 5/1972 |

(Continued)

OTHER PUBLICATIONS

CAS Abstract U.S. Pat. No. 5,484,760 (1996).*

(Continued)

*Primary Examiner* — Alexander R Pagano
(74) *Attorney, Agent, or Firm* — Goodwin Procter LLP

(57) ABSTRACT

Compositions comprising compounds that modulate pyruvate kinase M2 (PKM2) are described herein. Also described herein are methods of using the compounds that modulate PKM2 in the treatment of cancer.

23 Claims, No Drawings

(56) References Cited

U.S. PATENT DOCUMENTS

| | | | |
|---|---|---|---|
| 7,572,913 B2 | 8/2009 | McKerracher et al. | |
| 7,615,553 B2 | 11/2009 | Van Emelen et al. | |
| 7,863,444 B2 | 1/2011 | Calderwood et al. | |
| 8,058,313 B2 | 11/2011 | Reddy et al. | |
| 8,642,660 B2 | 2/2014 | Goldfarb | |
| 8,742,119 B2 * | 6/2014 | Salituro | C07D 401/04 546/268.4 |
| 9,657,004 B2 * | 5/2017 | Salituro | C07D 401/04 |
| 2002/0035103 A1 | 3/2002 | Bennani et al. | |
| 2003/0082877 A1 | 5/2003 | Ootsuka et al. | |
| 2003/0095958 A1 | 5/2003 | Bhisetti et al. | |
| 2003/0106381 A1 | 6/2003 | Krouth et al. | |
| 2003/0158232 A1 | 8/2003 | Cheng et al. | |
| 2003/0187001 A1 | 10/2003 | Calderwood et al. | |
| 2003/0207882 A1 | 11/2003 | Stocker et al. | |
| 2004/0048283 A1 | 3/2004 | Pau et al. | |
| 2004/0152648 A1 | 8/2004 | Ullrich et al. | |
| 2004/0198979 A1 | 10/2004 | Dhanak et al. | |
| 2004/0235755 A1 | 11/2004 | Eigenbrodt et al. | |
| 2005/0176675 A1 | 8/2005 | Gorny | |
| 2007/0032418 A1 | 2/2007 | Shapiro et al. | |
| 2007/0127505 A1 | 6/2007 | Laurila et al. | |
| 2007/0280918 A1 | 12/2007 | Schwartz et al. | |
| 2008/0004269 A1 | 1/2008 | Xu et al. | |
| 2008/0021116 A1 | 1/2008 | Ullrich et al. | |
| 2008/0044833 A1 | 2/2008 | Connors | |
| 2008/0051414 A1 | 2/2008 | Hurley et al. | |
| 2009/0048227 A1 | 2/2009 | Chakravarty et al. | |
| 2009/0054453 A1 | 2/2009 | Alcaraz et al. | |
| 2009/0163545 A1 | 6/2009 | Goldfarb | |
| 2009/0247499 A1 | 10/2009 | Fletcher et al. | |
| 2009/0270454 A1 | 10/2009 | Weingarten et al. | |
| 2010/0105657 A1 | 4/2010 | Nordvall et al. | |
| 2010/0179150 A1 | 7/2010 | Basarab et al. | |
| 2010/0331307 A1 | 12/2010 | Salituro et al. | |
| 2011/0046083 A1 | 2/2011 | Cantley et al. | |
| 2011/0224252 A1 | 9/2011 | Dumeunier et al. | |
| 2011/0312931 A1 | 12/2011 | Cioffi et al. | |
| 2012/0122885 A1 | 5/2012 | Salituro et al. | |
| 2014/0249150 A1 | 9/2014 | Kung | |
| 2014/0323729 A1 | 10/2014 | Salituro et al. | |

FOREIGN PATENT DOCUMENTS

| | | |
|---|---|---|
| IT | 1176770 B | 8/1987 |
| JP | S61129129 A | 6/1986 |
| JP | H06025177 A | 2/1994 |
| JP | H07165708 A | 6/1995 |
| JP | 2002193710 A | 7/2002 |
| JP | 2007238458 A | 9/2007 |
| JP | 2008514590 A | 5/2008 |
| JP | 2011507910 A | 3/2011 |
| WO | 8501289 A1 | 3/1985 |
| WO | 1992011761 A1 | 7/1992 |
| WO | 9313072 A1 | 7/1993 |
| WO | 1996030343 A1 | 10/1996 |
| WO | 9728128 A1 | 8/1997 |
| WO | 9728129 A1 | 8/1997 |
| WO | 9728141 A1 | 8/1997 |
| WO | 1997044322 A1 | 11/1997 |
| WO | 9803350 A1 | 1/1998 |
| WO | 199916751 A1 | 4/1999 |
| WO | 990062506 A1 | 12/1999 |
| WO | 00/17202 A1 | 3/2000 |
| WO | 0053596 A2 | 9/2000 |
| WO | 0107440 A1 | 2/2001 |
| WO | 2001019788 A2 | 3/2001 |
| WO | 2001019798 A2 | 3/2001 |
| WO | 2001064642 A2 | 9/2001 |
| WO | 2001064643 A2 | 9/2001 |
| WO | 2002072077 A2 | 9/2002 |
| WO | 02095063 A1 | 11/2002 |
| WO | 2002100822 A1 | 12/2002 |
| WO | 03016300 A1 | 2/2003 |
| WO | 0322277 A1 | 3/2003 |
| WO | 03037252 A2 | 5/2003 |
| WO | 03062235 A1 | 7/2003 |
| WO | 03076422 A1 | 9/2003 |
| WO | 2003073999 A2 | 9/2003 |
| WO | 2003093297 A2 | 11/2003 |
| WO | 2004004730 A2 | 1/2004 |
| WO | 2004014851 A2 | 2/2004 |
| WO | 2004037251 A1 | 5/2004 |
| WO | 2004073619 A2 | 9/2004 |
| WO | 2004074438 A2 | 9/2004 |
| WO | 2004089470 A2 | 10/2004 |
| WO | 2004110375 A2 | 12/2004 |
| WO | 2005072642 A1 | 8/2005 |
| WO | 2005117591 A2 | 12/2005 |
| WO | 2005120474 A2 | 12/2005 |
| WO | 2006004195 A1 | 1/2006 |
| WO | 2006016062 A1 | 2/2006 |
| WO | 2006033628 A1 | 3/2006 |
| WO | 2006034341 A2 | 3/2006 |
| WO | 2006038594 A1 | 4/2006 |
| WO | 2006043950 A1 | 4/2006 |
| WO | 2006/052190 A1 | 5/2006 |
| WO | 2006070198 A1 | 7/2006 |
| WO | 2006077821 A1 | 7/2006 |
| WO | 2006117762 A2 | 11/2006 |
| WO | 2006122546 A1 | 11/2006 |
| WO | 2007003934 A2 | 1/2007 |
| WO | 2007023186 A1 | 3/2007 |
| WO | 2007117465 A2 | 10/2007 |
| WO | 2007127505 A2 | 11/2007 |
| WO | 2008019139 A2 | 2/2008 |
| WO | 2008024284 A2 | 2/2008 |
| WO | 2008026658 A1 | 3/2008 |
| WO | 2008047198 A1 | 4/2008 |
| WO | 2008050168 A1 | 5/2008 |
| WO | 2008052190 A2 | 5/2008 |
| WO | 2008073670 A2 | 6/2008 |
| WO | 2009012430 A1 | 1/2009 |
| WO | 2009013126 A1 | 1/2009 |
| WO | 2009025781 A1 | 2/2009 |
| WO | 2009053102 A1 | 4/2009 |
| WO | 2009086303 A2 | 7/2009 |
| WO | 2010042867 A2 | 4/2010 |
| WO | 2010105243 A1 | 9/2010 |
| WO | 2010118063 A2 | 10/2010 |
| WO | 2010129596 A1 | 11/2010 |
| WO | 2010130638 A1 | 11/2010 |
| WO | 2011002816 A1 | 1/2011 |
| WO | 2011002817 A1 | 1/2011 |
| WO | 2011032169 A2 | 3/2011 |
| WO | 2011047432 A1 | 4/2011 |
| WO | 2011072174 A1 | 6/2011 |
| WO | 2011137089 A1 | 11/2011 |
| WO | 2012092442 A1 | 7/2012 |
| WO | 2012151452 A1 | 11/2012 |

OTHER PUBLICATIONS

Communication to CAS Help (Jul. 8, 2017).*
Lee. "Consolidation effect of phenylalanine-administration of antitumor activty of a 5-fluorouracil," Med. J. Kagoshima Univ., 1985, vol. 37, No. 3-4, p. 285-308.
Lee et al. "Pyruvate kinases isozyme type M2 (PKM2) interacts and cooperates with Oct-4 in regulating transcription," International J. Biochem. & Cell Biol., 2008, vol. 40, No. 5, p. 1043-54.
Li et al. "Quantitative proteome analysis of multidrug resistance in human ovarian cancer cell line," J. Cell Biochem., 2010, vol. 109, No. 4, p. 625-33.
Li et al. "Screening and identification of interactive proteins of SH2D4A," Yi Chuan, 2010, vol. 32, No. 7, p. 712-8, (abstract only).
Luo et al. "Synthesis and fungicidal activty of N-benzo[b][1,4]oxazin-6-yl-2,4-dimethylthiazole-5-carboxamides," Agrochemicals, 2009, vol. 48, No. 1, p. 19-22.
Mass. "The HER receptor family: a rich target for therapeutic development," Int. J. Radiation Oncology Bio. Phys., 2004, vol. 58, No. 3, p. 932-40.

(56) References Cited

OTHER PUBLICATIONS

Morshed et al. "Computational approach to the identification of novel Aurora-A inhibitors," Bioorganic & Medicinal Chemistry, 2011, col. 19, No. 2, p. 907-916.
Oeda. "On some 2,5-dialikl-piperazines," Bull. Chem. Soc., 1938, vol. 13, p. 465-70.
Park. "Prevention of type 2 diabetes mellitus from the viewpoint of genetics," Diabetes Research and Clinical Practice, 2004, vol. 66S, p. S33-S35.
Patel et al. "Synthesis of some new idolinone derivatives containing piperazine moiety," Bulgarian Chemical Communications, 2003, vol. 35, No. 4, p. 242-4.
Paudler et al. "3,7-disubstituted octahydro-1,5-diazocines. Their conversion into tetrahydro-1,5-diazocines and into ring-contracted products," J. Org. Chem., 1967, vol. 32, No. 8, p. 2425-30.
Pollard et al. "Some amides of piperazines," J. Am. Chem. Soc., 1953, vol. 75, No. 2, p. 491.
Proisy et al. "Rapid synthesis of 3-aminoisoquinoline-5-sulfonamides using the Buchwald-Hartwig reaction," Synthesis, 2009, No. 4, p. 0561-6.
Pujal et al. "Is there a case for cisplatin in the treatment of small cell lung cancer? A meta-analysis of randomized trials of cisplatin-containing regimen versus a regimen without this alkylating agent," British Journal of Cancer, Cancer Research Campaign, 2000, vol. 83, iss. 1, p. 8-15.
Remington. "Structure Activity Relationship and Drug Design," Pharmaceutical Sciences, 1980, p. 420-5.
Rich et al. "Development of novel targeted therapies in the treatment of malignant glioma," Nature Rev. Drug Disc., 2004, vol. 3, p. 430-46.
Root et al. "Genome-scale loss-of-function screening with a lentiviral RNAi library," Nat. Methods, 2006, vol. 3, p. 715-9.
Ruan et al. "HSP60, a protein downregulated by IGFBP7 in colorectal carcinoma," J. Exp. Clin. Cancer Res., 2010, vol. 29, p. 41.
Sabatine et al. "Metabolomic identification of novel biomarkers of myocardial ischemia," Circulation, 2005, vol. 112, p. 3868-75.
Schneider et al. "Tumor M2-pyruvate kinase in the follow-up of inoperable lung cancer patients: a pilot study," Cancer Letters, 2003, vol. 193, p. 91-98.
Schroth et al. "Ringschlu breaktion von diacetylen mit diaminen: Eine ciniache von 2,3-dihydro-1,4-diazepinen," Zeitschritt Fur Chemie., 1969, vol. 6, No. 4, p. 143.
Siebel et al. "Synthesis and evaluation of B-lactams (piperazones) as elastase inhibitors," Bioorg. Med. Chem. Lett., 2003, vol. 13, No. 3, p. 387-9.
Shi et al. "Silencing of PKM2 increases the efficacy of doxetaxel in human lung cancer xenografts in mice," Cancer Science, 2010, vol. 101, No. 6, p. 1447-53.
Steiner et al. "Synthesis and antihypertensive activity of new 6-heteroaryl-3-hydrazinopyridazine derivatives," Journal of Medicinal Chemistry, 1981, vol. 24, No. 1, p. 59-63.
Stewart et al. "Piperazines. I. Derivatives of piperazine-1-carboxylic acid and -1,4-dicarboxylic acid," J. Org. Chem., 1953, vol. 18, No. 1, p. 1478-83.
STN file CA, Registry No. 1023411-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN file CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 321433-63-0, entered STN on Feb. 12, 2001, Chemical Abstracts Index Name "1H-Pyrrole-2-sulfonamide, 1-[3-chloro-5-(trifluoromethyl)-2-pyridinyl]-N-phenyl" Available though Key Organics (under the BIONET brand) Jan. 1994.
STN File CA, Registry No. 321433-64-1, entered STN on Feb. 12, 2001, Chemical Abstracts Index Name "1H-Pyrrole-2-sulfonamide, 1-[3-chloro-5-(trifluoromethyl)-2-pyridinyl]-N-(4-methphenyl)" Available though Key Organics (under the BIONET brand) Jan. 1994.
STN File CA, Registry No. 321433-65-2, entered STN on Feb. 12, 2001, Chemical Abstracts Index Name "1H-Pyrrole-2-sulfonamide, 1-[3-chloro-5-(trifluoromethyl)-2-pyridinyl]-N-(3,5-dimethylphenyl)" Available though Key Organics (under the BIONET brand) Jan. 1994.
STN File CA, Registry No. 321433-66-3, entered STN on Feb. 12, 2001, Chemical Abstracts Index Name "1 H-Pyrrole-2-sulfonamide, 1-[3-chloro-5-(trifluoromethyl)-2-pyridinyl]-N-(4-methoxyphenyl)" Available though Key Organics (under the BIONET brand) Jan. 1994.
STN File CA, Registry No. 321433-68-5, entered STN on Feb. 12, 2001, Chemical Abstracts Index Name "1 H-Pyrrole-2-sulfonamide, 1-[3-chloro-5-(trifluoromethyl)-2-pyridinyl]-N-propyl" Available though Key Organics (under the BIONET brand) Jan. 1994.
STN File CA, Registry No. 321433-69-6, entered STN on Feb. 12, 2001, Chemical Abstracts Index Name "1H-Pyrrole-2-sulfonamide, 1-[3-chloro-5-(trifluoromethyl)-2-pyridinyl]-N-(2-methoxyethyl)" Available though Key Organics (under the BIONET brand) Jan. 1994.
STN File CA, Registry No. 338397-92-5, entered STN on May 25, 2001, Chemical Abstracts Index Name "1H-Pyrrole-2-sulfonamide, 1-[3-chloro-5-(trifluoromethyl)-2-pyridinyl]-N,N-dimethyl" Available though Key Organics (under the BIONET brand) Feb. 1993.
STN File CA, Registry No. 338397-95-8, entered STN on May 25, 2001, Chemical Abstracts Index Name "1H-Pyrrole-2-sulfonamide, N-[(4-chlorophenyl)-1-[3-chloro-5-(trifluoromethyl)-2-pyridinyl]" Available though Key Organics under the BIONET brand) Feb. 1993.
STN File CA, Registry No. 338397-96-9, entered STN on May 25, 2001, Chemical Abstracts Index Name "1H-Pyrrole-2-sulfonic acid, 1-[3-chloro-5-(trifluoromethyl)-2-pyridinyl]-4-chlorophenyl ester" Available though Key Organics under the BIONET brand) Feb. 1993.
STN File CA, Registry No. 338406-58-9, entered STN on May 25, 2001, Chemical Abstracts Index Name "1 H-Pyrrole-2-sulfonamide, 1-[3-chloro-5-(trifluoromethyl)-2-pyridinyl]-N-[2-(trifluoromethyl)phenyl]" Available though Key Organics (under the BIONET brand) Mar. 1993.
STN File CA, Registry No. 338406-64-7, entered STN on May 25, 2001, Chemical Abstracts Index Name "1H-Pyrrole-2-sulfonamide, 1-[3-chloro-5-(trifluoromethyl)-2-pyridinyl]-N-(3-pyridinylmethyl)" Available though Key Organics under the BIONET brand) Mar. 1993.
STN File CA, Registry No. 338406-72-7, entered STN on May 25, 2001, Chemical Abstracts Index Name "1H-Dyrrole-2-sulfonamide, N-[(4-chlorophenyl)methyl]-1-[3-chloro-5-(trifluoromethyl)-2-pyridinyl]" Available though Key Organics (under the BIONET brand) Mar. 1993.
STN File CA, Registry No. 338407-11-7, entered STN on May 25, 2001, Chemical Abstracts Index Name "1H-Pyrrole-2-sulfonamide, 1-[3-chloro-5-(trifluoromethyl)-2-pyridinyl]-N-[3-chloro-4-[[5-(trifluoromethyl)-2-pyridinyl] oxyphenyll]" Available though Key Organics (under the BIONET brand) Mar. 1993.
STN File CA, Registry No. 338407-13-9, entered STN on May 25, 2001, Chemical Abstracts Index Name "Benzoic acid,3-[[[1-[3-chloro-5-(trifluoromethyl)-2-pyridinyl]-1H-pyrrol-2-yl]sulfonyl]amino]" Available though Key Organics under the BIONET brand) Mar. 1993.
STN File CA, Registry No. 713505-78-3, entered STN on Jul. 21, 2004, Chemical Abstracts Index Name "1-Diperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-diftuoro-N-[3-334-(phenylmethyl0-1-piperazinyl] carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N ,4-dimethyl-" or "Piperazine, 1-(1,3-

(56) References Cited

OTHER PUBLICATIONS benzodioxol-5-ylmethyl)-4-[5-[[(4-ethoxyphenyl)methylamino]sulfonyl]-2-methylbenzoyl]-".
STN Tokyo, Registry No. 1001833-18-6, Entered STN on Feb. 6, 2008, Chemical Abstracts Index Name "1,4-Benzodioxin-6-sulfonamide, 2,3-dihydro-N-[4-[(4-methyl-1-piperazinyl)carbonyl]phenyl]-".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4-[[4-[(5-methyl-3-isoxazolyl)methyl]-l-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4-[[4-(2-pyridinyl)-l-piperazinyl]carbonyl]phenyl]-".
STN Tokyo, Registry No. 1240875-006, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4-[[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[ (4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-[{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4-[[4-( cyclopropylcarbonyl)-1-piperazinyl]carbonyl]phenyl]-2,3-dihydro-".
STN Tokyo, Registry No. 9200679-46-5, Entered STN on Feb. 13, 2007, Chemical Abstracts Index Name "1,4-Benzodioxin-6-sulfonamide, 2,3-dihydro-N-[4-[[4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4-[[4-(4-fluoropheyl)-1-piperazinyl]carbonyl]phenyl]-2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4-[[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4-[[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4-[[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4-[[4-(2-thienylmethyl)-l-piperazinyl]carbonyl]phenyl]-".
STN Tokyo, Registry No. 920921-09-1 Entered STN on Feb. 14, 2007, Chemical Abstracts Index Name "2H-1,5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4-[[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-1-piperazinyl)carbonyl]phenyl]-".
Supplemental EP Search Report for EP 10714131.9 dated Oct. 17, 2014.
Surh. "Cancer Chemoprevention with Dietary Phytochemicals", Nature Reviews Cancer, 2003, vol. 3, p. 768-780.
Szoka et al. "Comparative properties and methods of preparation of lipid vesicles (liposomes )," Ann. Rev. Biophys. Bioeng., 1980, vol. 9, p. 467-508.
Tawaka et al., Caplus an 1998:794998.
Uozumi et al., "Catalytic asymmetric construction of morpholines and piperazines by palladium-catalyzed tandem allylic substitution reactions," J. Org. Chem., 1993, vol. 58, No. 24, p. 6826-6832.
Vanderheiden et al., "Growth Factors Can Influence Cell Growth and Survival Through Effects on Glucose Metabolism," Mol Cell Biol., 2001, vol. 21, p. 5899-5912.
Vanderheiden et al., "Identification of Small Molecule Inhibitors of Pyruvate Kinase M2," Biochemical Pharmacology, 2010, vol. 79, No. 8, p. 1118-1124.
Villen et al. "Large-Scale Phosphorylation Analysis of Mouse Liver," Proc Natl. Acad Sci USA, 2007, vol. 104, p. 1488-1493.
Villoutreix et al., Caplus an 2010:20993.
Walsh et al. "2-oxo-N-aryl-1,2,3,4-tetrahydroquinoline-6-sulfonamides as activators of the tumor cell specific M2 isoform of pyruvate kinase" Bioorg Med Chem Lett., 2011, vol. 21, No. 21, p. 6322-6327.
Web posting, Pyruvate kinase M2 isozyme {PKM2), SciBX 5(42), Published online Oct. 25, 2012, Abstract only.
Wong et al. "PKM2, a Central Point of Regulation in Cancer Metabolism," International Journal of Cell Biology, 2013, vol., p. 1-11.
Yamada et al. "Nutrient and Hormonal Regulation of Pyruvate Kinase Gene Expression," Biochem J., 1999, vol. 337, p. 1-11.
Yan et al., "IDH1 and IDH2 Mutations in Gliomas." The New England Journal of Medicine, 2009, vol. 360, No. 8, p. 765-73.
Yar et al., "An Annulation Reaction for the Synthesis of Morpholines, Thiomorpholines, and Piperazines from B-Heteroatom Amino Compounds and Vinyl Sulfonium Salts," Angewandte Chemie., 2008, vol. 47, No. 20, p. 3784-3786.
Ye et al. "Pyruvate kinase M2 promotes de nova serine synthesis to sustain mTORC1 activity and cell proliferation," PNAS, 2012, vol. 109, No. 18, p. 6904-6909.
E-mail Communication to CAS Support (2016).
CAS abstract WO 03016300 (2003).
Adveenko et al. "Thiocyanation of N-arylsulfonyl-, N-aroyl-, and N-[(N-arylsulfonyl)benzimidoyl]-1,4-benzoquinone imines," Russian Journal of Organic Chemistry, 2009, vol. 45, No. 3, p. 408-416.
Balss. "Analysis of the IDH1 codon 132 mutation in brain tumors," Acta Neuropathol, 2008, vol. 116, p. 597-602.
Baxter et al. "Preparation and some reactions of 6-arylsulphonimidobenzoxazol-2(3H)-one," Journal of the Chemical Society, 1970, p. 850-853.
Behun et al. "The chemistry of pyrazine and its dervatives. IV. The alkylation and arylation of methylpyrazine," J. Org. Chem., 1961, vol. 26, No. 9, p. 3379-3382.
Benesch et al. "The clinicopathological and prognostic relevance of pyruvate kinase M2 and pAkt expression in breast cancer," Anticancer Res., 2010, vol. 30, No. 5, p. 1689-94.

(56) References Cited

OTHER PUBLICATIONS

Berger et al. "Treatment of the pancreatic cancer: Challenge of the facts," World J. Surg., Societe Internationale de Chirugie, 2003, vol. 27, p. 1075-1083.
Bonuccelli et al. "The reverse Warburg effect: Glycolysis inhibitors prevent the tumor promoting effects of caveolin-1 deficient cancer associated fibroblasts," Cell Cycle, 2010, vol. 9, No. 10.
Boxer et al. "Identification of activators for the M2 isoform of human pyruvate kinase version 3," Probe Reports from the NIH Molecular Libraries Program [Internet]. Bethesda (MD): National Center for Biotechnology Information (US), 2009.
Boxer et al. "Evaluation of substituted N,N-diarylsulfonamides as activators of the tumor cell specific M2 isoform of pyruvate kinase," J. Med. Chem., 2010, vol. 53, No. 2, p. 1048.
Budinger et al. "Cellular energy utilization and supply during hypoxia in embryonic cardiac myocytes," Am. J. Physiol, 1996, vol. 270, p. L44-53.
Bushchow et al. "MHC class II-associated proteins in B-cell exosomes and potential functional implications for exocome biogenesis," Immunol. Cell Biol., 2010.
Cecil Textbook of Medicine, edited by Bennet, J.C. and Plum, F., 1996, 20th edition, vol. 1, p. 1004-1010.
Chabner et al. "Chemotherapy and the war on cancer," Nature Rev. Cancer, Nature Publishing Group, 2005, vol. 5, p. 65-72.
Chan et al. "Synthesis and characterization of poly(amide sulfonamide)s (PASAs)," J. Polymer Sci, 1995, vol. 33, No. 15, p. 2525-2531.
Christofk et al. "Pyruvate knase M2 is a phosphotyrosine-binding protein," Nature, 2008, vol. 452, p. 181-186.
Christofk et al. "The M2 splice isoform of pyruvate kinase is important for cancer metabolism and tumour growth," Nature, 2008, vol. 452, p. 230-233.
Clement et al. "Production of intracellular superoxide mediates dithiothreitol-dependent inhibition of apoptotic cell death," Antioxidants and Redox Signaling, 2005, vol. 7, p. 456-464.
Cohen et al. "The development and therapeutic potential of protein kinase inhibitors," Current Opinion in Chemical Biology, 1999, vol. 3, p. 459-465.
Conti et al. "Su alcuni anologhi assigenati della benzo-tiazine 2,3-diidro-3-cheto-benzo-1,4-ossazine 6-sostitute," Bollettino Scientifico Della Facolta Di Chimica Industriale Di Bologna, 1957, vol. 15, No. 2, p. 33-36.
Crawford et al, Caplus an 2010:1218943.
Cuzick et al. "Overview of the main outcomes in breast-cancer prevention trials," The Lancet, 2003, vol. 361, p. 296-300, 2003.
Database Chemcats, Chemical Abstracts Service, Columbus, OH, US, "Bionet screening compounds," Key Organics Ltd., Camelford, Cornwall, 2001.
Dermer et al. "Another anniversary for the war on cancer," Bio/Technology, 1994, vol. 12, p. 320.
Dombrauckas et al. "Structural basis for tumor pyruvate kinasa M2 allosteric regulation and catalysis," Biochemistry, 2005, vol. 44, p. 9717-9429.
Eigenbrodt et al. "Double role for pyruvate kinase type M2 in the expansion of phosphometabolite pools found in tumor cells," Crit. Rev. Oncog.,1992, vol. 3, p. 91-115, (abstract only).
Engelman et al. "Allelic dilution obscures detection of a biologically significant resistance mutation in EGFR-amplified lunch cancer," J. Clin. Invest., 2006, vol. 116, p. 2695-2706.
Eswaran et al. "Crystal structures and inhibitor identification for PTP5, PTPRR and PTPN7: a family of human MAPK-specific protein tyrosine phosphatases," Biochem J., 2006, vol. 395, p. 783-491.

Fabbro et al. "Protein kinases as targets for anticancer agents: from inhibitors to useful drugs," Pharmacology and Therapeutics, 2002, vol. 93, p. 79-89.
Freshney et al. "Culture of animal cells," A Manual of Basic Technique, Alan R. Liss, Inc., 1983, New York, p. 4.
Friedman et al. "Leptin and the regulation of body weight in mammals," Nature, 1996, vol. 395.
Furuya et al. "Inactivation of the 3-phosphoglycerate dehydrogenase gene in mice: changes in gene expression and associated regulatory networks resulting from serine deficiency," Funct. Integr. Genomics, 2008, vol. 8, p. 235-249.
Ge et al. "Anaplasma phagocytophillum inhibits human neutrophil apoptosis via upregulation of bfl-1, maintenance of mitochondrial membrane potential and prevention of caspase 3 activation," Cellular Microbiology, 2005, vol. 7, p. 29-38.
Golub et al. "Molecular classification of cancer: Class discovery and class prediction by gene expression monitoring," Science, 1999, vol. 286, 531-537.
Gupta et al. "Dominant negative mutations affect oligomerisation of human pyruvate kinase M2 isozyme and promote cellular growth of polyploidy," J. Biol. Chem, 2010.
Hitsugi et al. "Tyrosine phosphorylation inhibits PKM2 to promote the Warbug effect and tumor growth," Sci. Signal., 2009, vol. 2, iss. 97, p. ra73.
Hulleman et al. "Pyruvate kinase M2 and prednisolone resistance in acute lymphoblastic leukemia," Haematologica, 2009, vol. 94, No. 9, p. 1322-1324.
Inglese et al. "Quantitative high-throughput screening: a titration-based approach that efficiently identifies biological activities in large chemical libraries," Proc. Natl. Acad. Sci., 2006, vol. 103, No. 31, p. 11473-8.
International Search Report and Written Opinion for PCT/US2010/030139 dated Dec. 10, 2010.
Jiang et al. "Evaluation of thieno[3,2-b]pyrrole[3,2-dipyridazinones as activators of the tumor specific M2 isoform of pyruvate kinase," Bioorg. Med. Chem. Lett., 2010, vol. 20, No. 11, p. 3387-3393.
Jurica et al. "The allosteric regulation of pyruvate kinase by fructose-1,6-bisphosphate," Structure, 1998, vol. 6, p. 195-210.
Joshi et al. "Age-related faecal calprotectin, lactoferrin and tumour M2-PK concentrations in healty volunteers," Ann. Clin. Biochem., 2010, vol. 47, p. 259-63.
Kao et al. "A small-molecule inhibitor of the ribonucleolytic activity of human angiogenin that possesses antitumor activity," Proc. Natl. Acad. Sci. USA, 2002, vol. 99, vol. 15, p. 10066-71.
Kharalkar et al. "Identification of novel allosteric regulators of human-erythrocyte pyruvate kinase," Chem. Biodivers., 2007, vol. 4, p. 2603-17.
Klapars et al. "A general and efficient copper catalyst for the amidation of aryl halides and the N-arylation of nitrogen heterocycles," J. Am. Chem. Soc., 2001, vol. 123, No. 31, p. 7727-9.
Komoriya et al. "Design, synthesis, and biological activity of non-basic compounds as factor Xa inhibitors: SAR study of S1 and aryl binding sites," Bioorganic & Medicinal Chemistry, 2005, vol. 13, p. 3927-3954.
Kumar et al. "In vivo factors influencing tumour M2-pyruvate kinase level in human pancreatic cancer cell lines," Tumour Biol., 2010, vol. 31, No. 2, p. 69-77.
Kung et al. "Small molecule activation of PKM2 in cancer cells induces serine auxotrophy," Chemistry & Biology, 2012, vol. 19, p. 1187-98.
Lee et al. "An efficient synthesis of 2,8-diazabicyclo[4,3,0]-nonane derivatives via intramolecular cyclization reaction," Synth. Comm., 1995, vol. 25, No. 23, p. 3741-6.

\* cited by examiner

THERAPEUTIC COMPOSITIONS AND RELATED METHODS OF USE

CLAIM OF PRIORITY

This application is a divisional of U.S. Ser. No. 14/836,330, filed Aug. 26, 2015, which is a continuation of U.S. Ser. No. 14/277,957, filed May 15, 2014, which is a divisional of U.S. Ser. No. 13/267,494, filed Oct. 6, 2011, now U.S. Pat. No. 8,742,119, issued Jun. 3, 2014, which is a continuation of International Application No. PCT/US2010/030139, filed Apr. 6, 2010, which claims priority from U.S. Ser. No. 61/233,470, filed Aug. 12, 2009, and U.S. Ser. No. 61/167,017, filed Apr. 6, 2009, each of which is incorporated herein by reference in its entirety.

BACKGROUND OF INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Thus, the modulation (e.g., inhibition or activation) of PKM2 may be effective in the treatment of, e.g., obesity, diabetes, autoimmune conditions, and proliferation-dependent diseases, e.g., benign prostatic hyperplasia (BPH). Current modulators (e.g., inhibitors) of pyruvate kinase are not selective, making it difficult to treat disease related to pyruvate kinase function.

Furthermore, phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 can also inhibit the growth and proliferation of cancer cells, activated immune cells, and fat cells.

There is a continuing need for novel treatments of diseases such as cancer, diabetes, obesity, autoimmune conditions, proliferation-dependent diseases (e.g., BPH), and other diseases related to the function of pyruvate kinase (e.g., PKM2).

SUMMARY OF INVENTION

Described herein are compounds that modulate pyruvate kinase M2 (PKM2) and pharmaceutically acceptable salts, solvates, and hydrates thereof, for example, compounds that modulate PKM2. This invention also provides compositions and pharmaceutical kits comprising a compound of this invention and the use of such compositions and kits in methods of treating diseases and conditions that are related to pyruvate kinase function (e.g., PKM2 function), including, e.g., cancer, diabetes, obesity, autoimmune disorders, and benign prostatic hyperplasia (BPH).

In one aspect, the present invention features a compound or pharmaceutically acceptable salt thereof of formula (I):

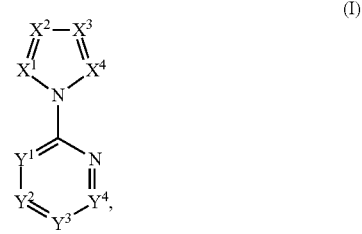

wherein
$X^1$ is N or CE;
$X^2$ is N or CD;
$X^3$ is N or CB;
$X^4$ is N or CA;
$Y^1$, $Y^2$, $Y^3$ and $Y^4$ are each independently selected from N and $CR^1$;
A, B, D and E are each independently selected from H, $R^3$ and —$SO_2$—$NR^4R^5$;
wherein at least one of $X^1$, $X^2$, $X^3$, $X^4$, $Y^1$, $Y^2$, $Y^3$ and $Y^4$ is N; and at least one of $X^1$, $X^2$, $X^3$, $X^4$, is C—$SO_2$—$NR^4R^5$;
each $R^4$ is independently selected from $C_{1-8}$ alkyl, aryl and heteroaryl, each of which is substituted with n occurrences of $R^2$;
each $R^5$ is independently hydrogen or $C_{1-8}$ alkyl;
each $R^1$ is independently selected from hydrogen, $C_{1-8}$ alkyl, $C_{1-8}$ terminal alkynyl, $C_{1-8}$ alkoxy, halogen, haloalkyl and haloalkoxy;
each $R^2$ is independently selected from halo, haloalkyl, $C_{1-4}$ alkyl, $C_{2-4}$ alkenyl, $C_{2-4}$ alknynyl, aryl, heteroaryl, aralkyl, heteroaralkyl, cyano, —$OR^a$, —$COOR^b$ and —$CONR^cR^c$; wherein two $R^2$, together with the carbons to which they are attached, may form an optionally substituted ring, each of which can be further substituted;
each $R^3$ is independently selected from $C_{1-8}$ alkyl, —$OR^a$, halogen, haloalkyl, haloalkoxy and optionally substituted heteroaryl;
each $R^a$ is independently selected from alkyl, haloalkyl, optionally substituted heteroaryl and optionally substituted heterocyclyl;
each $R^b$ is independently alkyl; and
each $R^c$ is independently selected from hydrogen and alkyl; and
n is 0, 1, 2 or 3.

In some embodiments, one of $X^1$, $X^2$, $X^3$, $X^4$, is C—$SO_2$—$NR^4R^5$;
In some embodiments, $X^4$ is A and A is —$SO_2$—$NR^4R^5$. In some embodiments, $X^3$ is B and B is —$SO_2$—$NR^4R^5$. In some embodiments, $X^2$ is D and D is —$SO_2$—$NR^4R^5$. In some embodiments, $X^1$ is CE and E is —$SO_2$—$NR^4R^5$.

In some embodiments, the compound is a compound of formula (Ia):

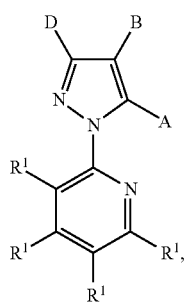
(Ia)

wherein A, B, D, $R^1$, $R^2$, $R^3$, $R^4$, $R^5$ and n are as defined in formula (I).

In some embodiments, A or B is —$SO_2$—$NR^4R^5$.

In some embodiments, the compound is a compound of formula (Ib):

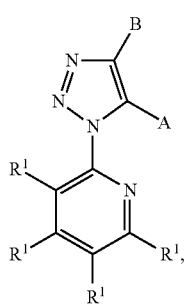
(Ib)

wherein A, B, $R^1$, $R^2$, $R^3$, $R^4$, $R^5$ and n are as defined in formula (I).

In some embodiments, A or B is —$SO_2$—$NR^4R^5$.

In some embodiments, the compound is a compound of formula (Ic):

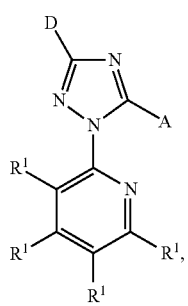
(Ic)

wherein A, D, $R^1$, $R^2$, $R^3$, $R^4$, $R^5$ and n are as defined in formula (I).

In some embodiments, A or D is —$SO_2$—$NR^4R^5$.

In some embodiments, the compound is a compound of formula (Id):

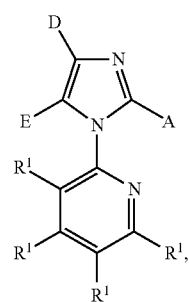
(Id)

wherein A, D, E, $R^1$, $R^2$, $R^3$, $R^4$, $R^5$ and n are as defined in formula (I).

In some embodiments, A is —$SO_2$—$NR^4R^5$.

In some embodiments, the compound is a compound of formula (Ie):

(Ie)

wherein A, B, E, $R^1$, $R^2$, $R^3$, $R^4$, $R^5$ and n are as defined in formula (I).

In some embodiments, A or B is —$SO_2$—$NR^4R^5$.

In some embodiments, the compound is a compound of formula (If):

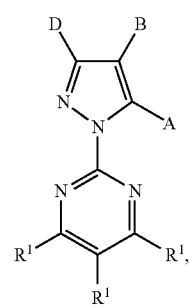
(If)

wherein A, B, D, $R^1$, $R^2$, $R^3$, $R^4$, $R^5$ and n are as defined in formula (I).

In some embodiments, A or B is —$SO_2$—$NR^4R^5$.

In some embodiments, the compound is a compound of formula (Ig):

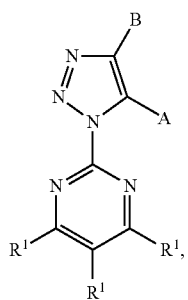

(Ig)

wherein A, B, $R^1$, $R^2$, $R^3$, $R^4$, $R^5$ and n are as defined in formula (I).

In some embodiments, A is —$SO_2$—$NR^4R^5$.
In some embodiments, B is —$SO_2$—$NR^4R^5$.
In some embodiments, the compound is a compound of formula (Ih):

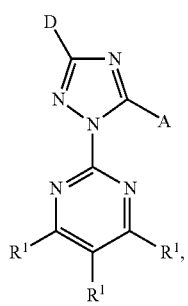

(Ih)

wherein A, D, $R^1$, $R^2$, $R^3$, $R^4$, $R^5$ and n are as defined in formula (I).

In some embodiments, A is —$SO_2$—$NR^4R^5$.
In some embodiments, the compound is a compound of formula (Ij):

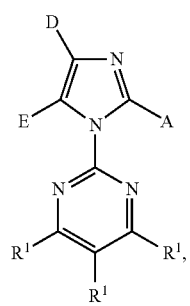

(Ij)

wherein A, D, E, $R^1$, $R^2$, $R^3$, $R^4$, $R^5$ and n are as defined in formula (I).

In some embodiments, A is —$SO_2$—$NR^4R^5$.
In some embodiments, the compound is a compound of formula (Ik):

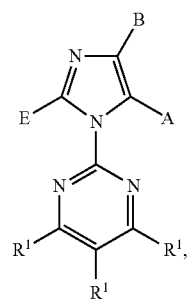

(Ik)

wherein A, B, E, $R^1$, $R^2$, $R^3$, $R^4$, $R^5$ and n are as defined in formula (I).

In some embodiments, A or B is —$SO_2$—$NR^4R^5$.
In some embodiments, the compound is a compound of formula (Im):

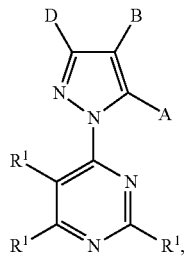

(Im)

wherein A, B, D, $R^1$, $R^2$, $R^3$, $R^4$, $R^5$ and n are as defined in formula (I).

In some embodiments, A or B is —$SO_2$—$NR^4R^5$.
In some embodiments, the compound is a compound of formula (In):

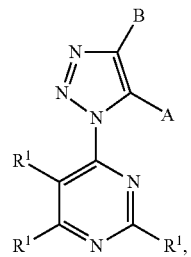

(In)

wherein A, B, $R^1$, $R^2$, $R^3$, $R^4$, $R^5$ and n are as defined in formula (I).

In some embodiments, A is —$SO_2$—$NR^4R^5$.
In some embodiments, B is —$SO_2$—$NR^4R^5$.
In some embodiments, the compound is a compound of formula (Io):

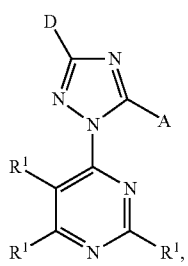
(Io)

wherein A, D, $R^1$, $R^2$, $R^3$, $R^4$, $R^5$ and n are as defined in formula (I).

In some embodiments, A is —$SO_2$—$NR^4R^5$.

In some embodiments, the compound is a compound of formula (Ip):

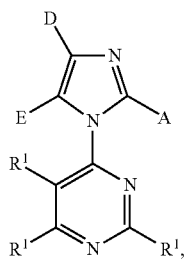
(Ip)

wherein A, D, E, $R^1$, $R^2$, $R^3$, $R^4$, $R^5$ and n are as defined in formula (I).

In some embodiments, A is —$SO_2$—$NR^4R^5$.

In some embodiments, the compound is a compound of formula (Iq):

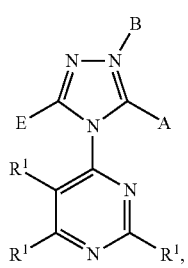
(Iq)

wherein A, B, E, $R^1$, $R^2$, $R^3$, $R^4$, $R^5$ and n are as defined in formula (I).

In some embodiments, A or B is —$SO_2$—$NR^4R^5$.

In some embodiments, the compound is a compound of formula (Ir):

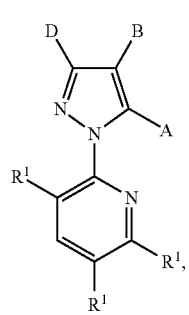
(Ir)

wherein A, B, D, $R^1$, $R^2$, $R^3$, $R^4$, $R^5$ and n are as defined in formula (I).

In some embodiments, A or B is —$SO_2$—$NR^4R^5$.

In some embodiments, the compound is a compound of formula (Is):

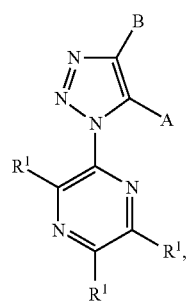
(Is)

wherein A, B, D, E, $R^1$, $R^2$, $R^3$, $R^4$, $R^5$, m and n are as defined in formula (I).

In some embodiments, A is —$SO_2$—$NR^4R^5$.
In some embodiments, B is —$SO_2$—$NR^4R^5$.

In some embodiments, the compound is a compound of formula (It):

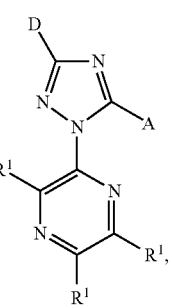
(It)

wherein A, D, $R^1$, $R^2$, $R^3$, $R^4$, $R^5$ and n are as defined in formula (I).

In some embodiments, A is —$SO_2$—$NR^4R^5$.

In some embodiments, the compound is a compound of formula (Iu):

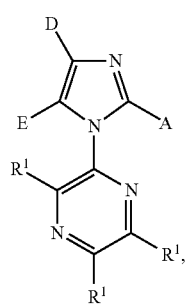
(Iu)

wherein A, D, E, $R^1$, $R^2$, $R^3$, $R^4$, $R^5$ and n are as defined in formula (I).

In some embodiments, A is —$SO_2$—$NR^4R^5$.

In some embodiments, the compound is a compound of formula (Iv):

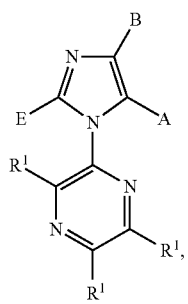

(Iv)

wherein A, B, E, $R^1$, $R^2$, $R^3$, $R^4$, $R^5$ and n are as defined in formula (I).

In some embodiments, A or B is $-SO_2-NR^4R^5$.

In some embodiments, the compound is a compound of formula (Iw):

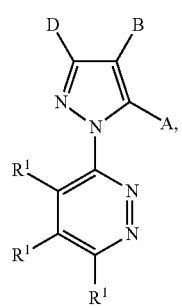

(Iw)

wherein A, B, D, $R^1$, $R^2$, $R^3$, $R^4$, $R^5$ and n are as defined in formula (I).

In some embodiments, A or B is $-SO_2-NR^4R^5$.

In some embodiments, the compound is a compound of formula (Ix):

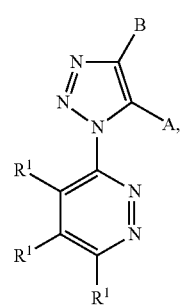

(Ix)

wherein A, B, $R^1$, $R^2$, $R^3$, $R^4$, $R^5$ and n are as defined in formula (I).

In some embodiments, A is $-SO_2-NR^4R^5$.

In some embodiments, B is $-SO_2-NR^4R^5$.

In some embodiments, the compound is a compound of formula (Iy):

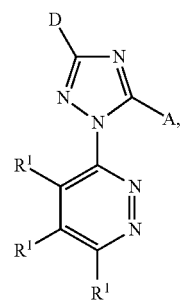

(Iy)

wherein A, D, $R^1$, $R^2$, $R^3$, $R^4$, $R^5$ and n are as defined in formula (I).

In some embodiments, A is $-SO_2-NR^4R^5$.

In some embodiments, the compound is a compound of formula (Iz):

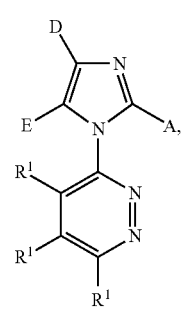

(Iz)

wherein A, D, E, $R^1$, $R^2$, $R^3$, $R^4$, $R^5$ and n are as defined in formula (I).

In some embodiments, A is $-SO_2-NR^4R^5$.

In some embodiments, the compound is a compound of formula (Iaa):

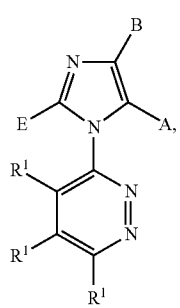

(Iaa)

wherein A, B, E, $R^1$, $R^2$, $R^3$, $R^4$, $R^5$ and n are as defined in formula (I).

In some embodiments, A is $-SO_2-NR^4R^5$.

In some embodiments, B is $-SO_2-NR^4R^5$.

In some embodiments, the compound is a compound of formula (Ibb):

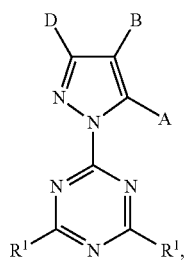

(Ibb)

wherein A, B, D, R$^1$, R$^2$, R$^3$, R$^4$, R$^5$ and n are as defined in formula (I).

In some embodiments, A is —SO$_2$—NR$^4$R$^5$.

In some embodiments, B is —SO$_2$—NR$^4$R$^5$.

In some embodiments, the compound is a compound of formula (Icc)

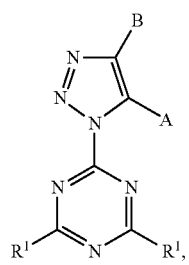

(Icc)

wherein A, B, R$^1$, R$^2$, R$^3$, R$^4$, R$^5$ and n are as defined in formula (I).

In some embodiments, A is —SO$_2$—NR$^4$R$^5$.

In some embodiments, B is —SO$_2$—NR$^4$R$^5$.

In some embodiments, the compound is a compound of formula (Idd):

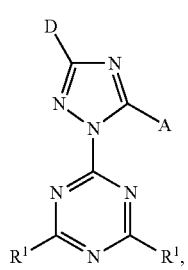

(Idd)

wherein A, D, R$^1$, R$^2$, R$^3$, R$^4$, R$^5$ and n are as defined in formula (I).

In some embodiments, A is —SO$_2$—NR$^4$R$^5$.

In some embodiments, the compound is a compound of formula (Iee):

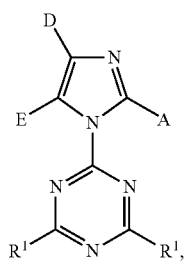

(Iee)

wherein A, D, E, R$^1$, R$^2$, R$^3$, R$^4$, R$^5$ and n are as defined in formula (I).

In some embodiments, A is —SO$_2$—NR$^4$R$^5$.

In some embodiments, the compound is a compound of formula (Iff):

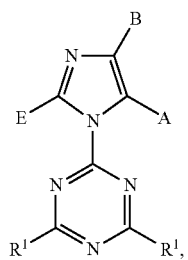

(Iff)

wherein A, B, E, R$^1$, R$^2$, R$^3$, R$^4$, R$^5$ and n are as defined in formula (I).

In some embodiments, A is —SO$_2$—NR$^4$R$^5$.

In some embodiments, B is —SO$_2$—NR$^4$R$^5$.

In one aspect, the invention features a pharmaceutical composition comprising a compound of formula (I) as described herein, or a pharmaceutically acceptable salt thereof.

In one aspect, the invention features a method of treating a disorder described herein (e.g., cancer) comprising administering to a subject a compound of formula (I) as described herein or a pharmaceutically acceptable salt thereof.

In one aspect, the invention features a method of preventing (e.g., preventing the onset of at least one symptom) or delaying the onset of a disorder as described herein (e.g., cancer) comprising administering to a subject a compound of formula (I) as described herein or a pharmaceutically acceptable salt thereof.

In one aspect, the present invention features a compound or pharmaceutically acceptable salt thereof of formula (II):

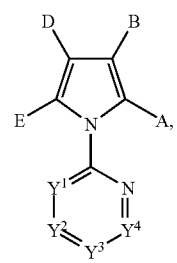

(II)

wherein

A, B, D and E are each independently selected from H, —SO$_2$—NR$^4$R$^5$ and R$^3$; wherein at least one of A, B, D, or E is —SO$_2$—NR$^4$R$^5$;

$Y^1$, $Y^2$, $Y^3$ and $Y^4$ are each independently selected from N and $CR^1$, wherein at least one of $Y^1$, $Y^2$, $Y^3$ and $Y^4$ are N;

each $R^4$ is independently selected from $C_{1-8}$ alkyl, aryl and heteroaryl, each of which is substituted with n occurrences of $R^2$;

each $R^5$ is independently hydrogen or $C_{1-8}$ alkyl;

each $R^1$ is independently selected from hydrogen, $C_{1-8}$ alkyl, $C_{1-8}$ terminal alkynyl, $C_{1-8}$ alkoxy, halogen, haloalkyl and haloalkoxy;

each $R^2$ is independently selected from halo, haloalkyl, $C_{1-4}$ alkyl, $C_{2-4}$ alkenyl, $C_{2-4}$ alknynyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from $C_{1-8}$ alkyl, —$OR^a$, halogen, haloalkyl, haloalkoxy and optionally substituted heteroaryl;

each $R^a$ is independently selected from alkyl, haloalkyl, optionally substituted heteroaryl and optionally substituted heterocyclyl;

each $R^b$ is independently alkyl; and each $R^c$ is independently selected from hydrogen and alkyl; and n is 0, 1, 2 or 3.

In some embodiments, at least one of $Y^1$, $Y^2$, $Y^3$ and $Y^4$ is N. In some embodiments, at least one of $Y^1$, $Y^2$, $Y^3$ and $Y^4$ are CH. In some embodiments, $Y^1$ is N. In some embodiments, $Y^3$ is N.

In some embodiments, each $R^1$ is independently hydrogen.

In some embodiments, the invention features a compound of formula (IIa):

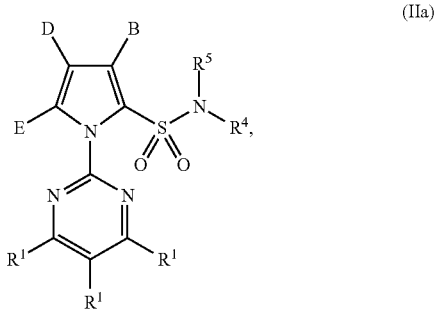

(IIa)

wherein n, B, D, E, $R^1$, $R^2$, $R^3$, $R^4$ and $R^5$ are defined as above.

In some embodiments, the invention features a compound of formula (IIb):

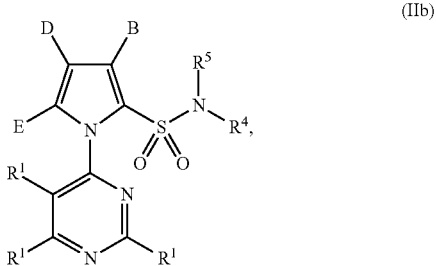

(IIb)

wherein n, B, D, E, $R^1$, $R^2$, $R^3$, $R^4$ and $R^5$ are defined as above.

In some embodiments, B, D and E are each independently selected from H.

In some embodiments, $R^5$ is hydrogen.

In some embodiments, each $R^1$ is independently hydrogen. In some embodiments, each $R^1$ is independently selected from $C_{1-8}$ alkyl, halogen or haloalkyl. In some embodiments, each $R^1$ is independently selected from halogen or haloalkyl. In some embodiments, each $R^1$ is independently selected from halogen (e.g., chlorine or fluorine). In some embodiments, each $R^1$ is independently haloalkyl (e.g., trifluoroalkyl).

In some embodiments, $R^4$ is selected from aryl or heteroaryl. In some embodiments, $R^4$ is aryl substituted with n occurrences of $R^2$. In some embodiments, $R^4$ is $C_{5-8}$ monocyclic aryl or $C_{8-14}$ bicyclic aryl. In some embodiments, $R^4$ is $C_{5-8}$ monocyclic aryl (e.g., optionally substituted phenyl). In some embodiments, $R^4$ is phenyl substituted with n occurrences of $R^2$.

In some embodiments, n is 0. In some embodiments, n is 1.

In some embodiments, $R^2$ is halo, $C_{1-4}$ alkyl or haloalkyl, each of which can be further substituted.

In some embodiments, $R^2$ is $C_{1-4}$ alkyl (e.g., ethyl). In some embodiments, $R^2$ is halo (e.g., chloro). In some embodiments, $R^2$ is haloalkyl (e.g., trifluoromethyl).

In some embodiments, n is 2. In some embodiments, both $R^2$ are $C_{1-4}$ alkyl (e.g., methyl). In some embodiments, n is 2. In some embodiments, both $R^2$ are halo (e.g., fluoro or chloro). In some embodiments, n is 2. In some embodiments, one $R^2$ is haloalkyl (e.g., trifluoroalkyl) and the other $R^2$ is —$OR^a$. In some embodiments, $R^a$ is alkyl (e.g., methyl or ethyl). In some embodiments, n is 2. In some embodiments, one $R^2$ is halo (e.g., fluoro or chloro) and the other $R^2$ is $C_{1-4}$ alkyl (e.g., methyl or ethyl).

In some embodiments, n is 2. In some embodiments, two $R^2$, together with the carbon atoms to which they are attached, form a 5-membered heterocyclic ring. In some embodiments, two $R^2$, together with the phenyl ring to which they are attached, form the following structure:

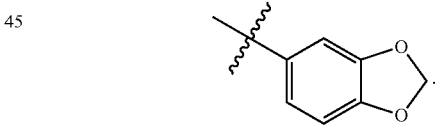

In some embodiments, n is 3. In some embodiments, all $R^2$ are halo (e.g., fluoro or chloro).

In another aspect, the invention features a pharmaceutical composition comprising a compound selected from Formula (II), (IIa) or (IIb) as described herein or a pharmaceutically acceptable salt thereof.

In another aspect, the invention features a method of treating a disorder described herein (e.g., cancer) comprising administering to a subject a compound of formula (II), (IIa) or (IIb) as described herein or a pharmaceutically acceptable salt thereof.

In another aspect, the invention features a method of preventing (e.g., preventing the onset of at least one symptom) or delaying the onset of a disorder as described herein (e.g., cancer) comprising administering to a subject a compound of formula (II), (IIa) or (IIb) as described herein or a pharmaceutically acceptable salt thereof.

In one aspect, the present invention features a compound or pharmaceutically acceptable salt thereof of formula (III):

(III)

wherein
$X^1$ is N or CE;
$X^2$ is N or CD;
$X^3$ is N or CB;
$X^4$ is N or CA, wherein at least one of $X^1$, $X^2$, $X^3$ and $X^4$ is N and at least one of $X^1$, $X^2$, $X^3$, $X^4$, is C—$SO_2$—$NR^4R^5$;
A, B, D and E are each independently selected from H, $R^3$ and —$SO_2$—$NR^4R^5$;
$Y^2$ is selected from N and $CR^1$;
each $R^4$ is independently selected from $C_{1-8}$ alkyl, aryl and heteroaryl, each of which is substituted with n occurrences of $R^2$;
$R^5$ is hydrogen or $C_{1-8}$ alkyl;
each $R^1$ is independently selected from hydrogen, $C_{1-8}$ alkyl, $C_{1-8}$ terminal alkynyl, $C_{1-8}$ alkoxy, halogen, haloalkyl and haloalkoxy;
each $R^2$ is independently selected from halo, haloalkyl, $C_{1-4}$ alkyl, $C_{2-4}$ alkenyl, $C_{2-4}$ alkynyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;
each $R^3$ is independently selected from $C_{1-8}$ alkyl, —$OR^a$, halogen, haloalkyl, haloalkoxy and optionally substituted heteroaryl;
each $R^a$ is independently selected from alkyl, haloalkyl, optionally substituted heteroaryl and optionally substituted heterocyclyl;
each $R^b$ is independently alkyl; and
each $R^c$ is independently selected from hydrogen and alkyl; and
n is 0, 1, 2 or 3.

In some embodiments, the invention features a compound of formula (IIIa):

(IIIa)

wherein n, B, D, E, $R^1$, $R^4$, $R^2$ and $R^5$ are defined as in formula (III).

In some embodiments, the invention features a compound of formula (IIIb):

(IIIb)

wherein n, B, E, $R^1$, $R^4$, $R^2$ and $R^5$ are defined as in formula (III).

In some embodiments, the invention features a compound of formula (IIIc):

(IIIc)

wherein n, B, D, $R^1$, $R^4$, $R^2$ and $R^5$ are defined as in formula (III).

In some embodiments, B and E are each independently selected from H.
In some embodiments, $R^5$ is hydrogen.
In some embodiments, each $R^1$ is independently hydrogen. In some embodiments, each $R^1$ is independently selected from $C_{1-8}$ alkyl, halogen or haloalkyl. In some embodiments, each $R^1$ is independently selected from halogen or haloalkyl. In some embodiments, each $R^1$ is independently selected from halogen (e.g., chlorine or fluorine). In some embodiments, each $R^1$ is independently haloalkyl (e.g., trifluoroalkyl).
In some embodiments, $R^4$ is selected from aryl or heteroaryl. In some embodiments, $R^4$ is aryl substituted with n occurrences of $R^2$. In some embodiments, $R^4$ is $C_{5-8}$ monocyclic aryl or $C_{8-14}$ bicyclic aryl. In some embodiments, $R^4$ is $C_{5-8}$ monocyclic aryl (e.g., optionally substituted phenyl). In some embodiments, $R^4$ is phenyl substituted with n occurrences of $R^2$.
In some embodiments, n is 0. In some embodiments, n is 1.
In some embodiments, $R^2$ is halo, $C_{1-4}$ alkyl or haloalkyl, each of which can be further substituted.
In some embodiments, $R^2$ is $C_{1-4}$ alkyl (e.g., methyl or ethyl). In some embodiments, $R^2$ is halo (e.g., chloro).
In some embodiments, n is 2. In some embodiments, both $R^2$ are $C_{1-4}$ alkyl (e.g., methyl or ethyl). In some embodiments, n is 2. In some embodiments, both $R^2$ are halo (e.g., fluoro or chloro). In some embodiments, n is 2. In some embodiments, one $R^2$ is haloalkyl (e.g., trifluoroalkyl) and the other $R^2$ is —$OR^a$. In some embodiments, $R^a$ is alkyl (e.g., methyl or ethyl). In some embodiments, n is 2. In some embodiments, one $R^2$ is $C_{1-4}$ alkyl (e.g., methyl or ethyl) and the other $R^2$ is halo (e.g., fluoro or chloro).

In some embodiments, n is 2. In some embodiments, two $R^2$, together with the carbon atoms to which they are attached, form a 5-membered heterocyclic ring. In some embodiments, two $R^2$, together with the phenyl ring to which they are attached, form the following structure:

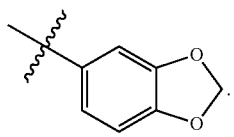 [SMILES: *c1ccc2c(c1)OCO2]

In some embodiments, n is 3. In some embodiments, all $R^2$ are halo (e.g., fluoro or chloro).

In another aspect, the invention features a pharmaceutical composition comprising a compound selected from formula (III), (IIIa), (IIIb) or (IIIc) as described herein or a pharmaceutically acceptable salt thereof.

In another aspect, the invention features a method of treating a disorder described herein (e.g., cancer) comprising administering to a subject a compound of formula (III), (IIIa), (IIIb) or (IIIc) as described herein or a pharmaceutically acceptable salt thereof.

In another aspect, the invention features a method of preventing (e.g., preventing the onset of at least one symptom) or delaying the onset of a disorder described here (e.g., cancer) comprising administering to a subject a compound of formula (III), (IIIa), (IIIb) or (IIIc) as described herein or a pharmaceutically acceptable salt thereof.

In another aspect, the invention features a compound or pharmaceutically acceptable salt thereof selected from the following formula:

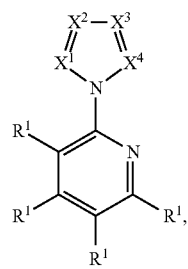

(IV)

wherein
n is 0, 1, 2 or 3;
$X^1$ is N or CE;
$X^2$ is N or CD;
$X^3$ is N or CB;
$X^4$ is N or CA, wherein at least one of $X^1$, $X^2$, $X^3$ and $X^4$ is N; and and at least one of $X^1$, $X^2$, $X^3$, $X^4$, is C—$SO_2$—$NR^4R^5$;
A, B, D and E are each independently selected from H and —$SO_2$—$NR^4R^5$;
each $R^4$ is independently selected from $C_{1-8}$ alkyl, aryl and heteroaryl, each of which is substituted with n occurrences of $R^2$;

each $R^5$ is independently hydrogen or $C_{1-8}$ alkyl;
each $R^1$ is independently selected from hydrogen, $C_{1-8}$ alkyl, $C_{1-8}$ alkoxy, halogen, haloalkyl and haloalkoxy;
each $R^2$ is independently selected from halo, haloalkyl, $C_{1-4}$alkyl, $C_{2-4}$ alkenyl, $C_{2-4}$ alkynylheteroaryl, aryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;
each $R^3$ is independently selected from $C_{1-8}$ alkyl, —$OR^a$, halogen, haloalkyl, haloalkoxy or optionally substituted heteroaryl;
$R^a$ is independently selected from alkyl, haloalkyl, optionally substituted heteroaryl and optionally substituted heterocyclyl;
each $R^b$ is independently alkyl; and
each $R^c$ is independently selected from hydrogen and alkyl.

In some embodiments, at least one of $X^3$ and $X^4$ are CH.
In some embodiments, at least one of A, B, D and E are H. In some embodiments, at least one of A, B, D and E are —$SO_2$—NH—$R^4$. In some embodiments, A is —$SO_2$—NH—$R^4$. In some embodiments, B is —$SO_2$—NH—$R^4$.

In some embodiments, the invention features a compound of formula (IVa):

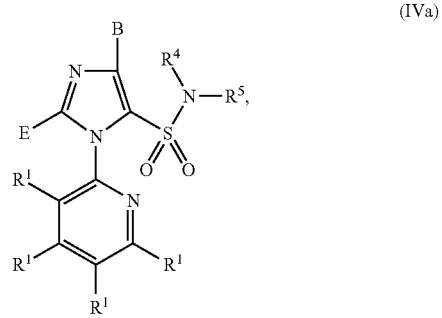

(IVa)

wherein n, B, E, $R^1$, $R^4$, $R^3$, $R^2$ and $R^5$ are defined as above.

In some embodiments, the invention features a compound of formula (IVb):

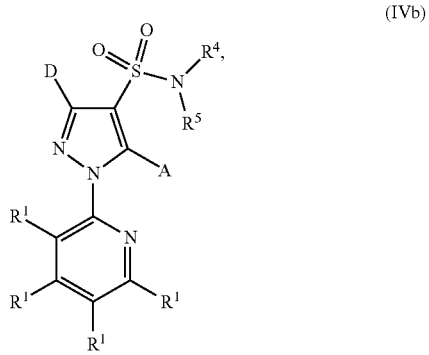

(IVb)

wherein n, A, D, E, $R^1$, $R^4$, $R^3$, $R^2$, and $R^5$ are defined as above.

In some embodiments, A, and D are H. In some embodiments, B and E are H.

In some embodiments, $R^5$ is hydrogen.

In some embodiments, each $R^1$ is independently H. In some embodiments, each $R^1$ is independently selected from $C_{1-8}$ alkyl, halogen or haloalkyl. In some embodiments, each $R^1$ is independently selected from halogen or haloalkyl. In some embodiments, each $R^1$ is independently selected from halogen (e.g., chlorine or fluorine). In some embodiments, each $R^1$ is independently haloalkyl (e.g., trifluoroalkyl).

In some embodiments, $R^4$ is selected from aryl or heteroaryl. In some embodiments, $R^4$ is aryl substituted with n occurrences of $R^2$. In some embodiments, $R^4$ is $C_{5-8}$ monocyclic aryl or $C_{8-14}$ bicyclic aryl. In some embodiments, $R^4$ is $C_{5-8}$ monocyclic aryl (e.g., phenyl). In some embodiments, $R^4$ is phenyl substituted with n occurrences of $R^2$. In some embodiments, $R^4$ is $C_{8-14}$ bicyclic aryl (e.g., napthyl). In some embodiments, $R^4$ is a 5-8 membered heteroaryl or a 8-14 membered heteroaryl. In some embodiments, $R^4$ is a 8-14 membered heteroaryl (e.g., 5-quinolyl or 6-quinolyl). In some embodiments, $R^4$ is quinolyl (e.g., 5-quinolyl or 6-quinolyl) substituted with n occurrences of $R^2$.

In some embodiments, n is 0. In some embodiments, n is 1.

In some embodiments, $R^2$ is selected from halo, $C_{1-4}$ alkyl, cyano, haloalkyl, —$OR^a$ or two $R^2$, taken together with the carbon atoms to which they are attached form an optionally substituted ring, each of which can be further substituted.

In some embodiments, $R^2$ is halo (e.g., chloro or fluoro). In some embodiments, $R^2$ is $C_{1-4}$ alkyl (e.g., methyl or ethyl). In some embodiments, $R^2$ is cyano. In some embodiments, $R^2$ is haloalkyl (e.g., trifluoromethyl). In some embodiments, $R^2$ is —$OR^a$. In some embodiments, $R^a$ is alkyl (e.g., methyl).

In some embodiments, n is 2. In some embodiments, both $R^2$ are $C_{1-4}$ alkyl (e.g., methyl). In some embodiments, n is 2. In some embodiments, both $R^2$ are halo (e.g., fluoro or chloro). In some embodiments, n is 2. In some embodiments, one $R^2$ is $C_{1-4}$ alkyl and the other is halo (e.g., methyl and chloro or methyl and fluoro). In some embodiments, n is 2. In some embodiments, both $R^2$ are haloalkyl (e.g., trifluoromethyl). In some embodiments, n is 2. In some embodiments, both $R^2$ are —$OR^a$. In some embodiments, both $R^a$ are alkyl (e.g, methyl). In some embodiments, n is 2. In some embodiments, one $R^2$ is haloalkyl (e.g., trifluoromethyl) and one is —$OR^a$. In some embodiments, $R^a$ is alkyl (e.g., methyl).

In some embodiments, n is 2. In some embodiments, two $R^2$, taken together with the carbon atoms to which they are attached, form a 6-membered heterocyclic ring. In some embodiments, two $R^2$, taken together with the phenyl ring to which they are attached, for the following structure:

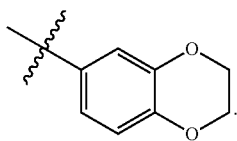 [SMILES: *c1ccc2c(c1)OCCO2]

In some embodiments, n is 3. In some embodiments, three $R^2$ are halo (e.g., fluoro).

In another aspect, the invention features a pharmaceutical composition comprising a compound selected from formula (IV), (IVa) or (IVb) as described herein or a pharmaceutically acceptable salt thereof.

In another aspect, the invention features a method of treating a disorder described herein (e.g., cancer) comprising administering to a subject a compound of formula (IV), (IVa) or (IVb) as described herein or a pharmaceutically acceptable salt thereof.

In another aspect, the invention features a method of preventing (e.g., preventing the onset of at least one symptom) or delaying the onset of a disorder described here (e.g., cancer) comprising administering to a subject a compound of formula (IV), (IVa) or (IVb) as described herein or a pharmaceutically acceptable salt thereof.

In another aspect, the invention features a pharmaceutical composition comprising a compound of formula (V):

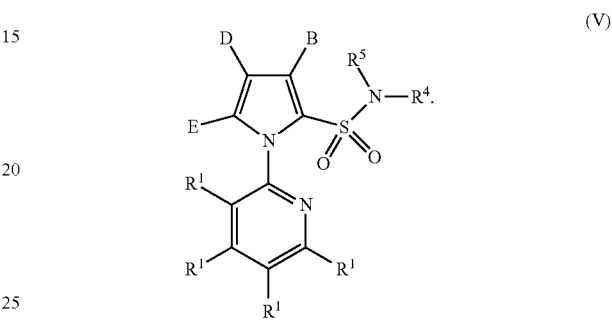

wherein

B, D and E are each independently selected from H and $R^3$;

each $R^1$ is independently selected from hydrogen, halo and haloalkyl;

$R^4$ is hydrogen, $C_{1-8}$ alkyl, and aryl, substituted with n occurrences of $R^2$;

each $R^2$ is independently selected from halo, haloalkyl, alkyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from halo, haloalkyl and —$OR^a$;

$R^5$ is hydrogen or $C_{1-8}$ alkyl;

$R^a$ is independently selected from alkyl, haloalkyl, optionally substituted heteroaryl and optionally substituted heterocyclyl;

each $R^b$ is independently alkyl;

each $R^c$ is independently selected from hydrogen and alkyl; and n is 0, 1, 2, or 3.

In some embodiments, B, D and E are each independently H.

In some embodiments, each $R^1$ is independently H. In some embodiments, each $R^1$ is independently halo (e.g., chloro). In some embodiments, each $R^1$ is independently haloalkyl (e.g., trifluoromethyl).

In some embodiments, one $R^1$ is halo and one $R^1$ is haloalkyl. In some embodiments, one $R^1$ is chloro and one $R^1$ is trifluoromethyl.

In some embodiments, $R^5$ is hydrogen.

In some embodiments, $R^5$ is $C_{1-8}$ alkyl (e.g., methyl).

In some embodiments, $R^4$ is hydrogen.

In some embodiments, $R^4$ is $C_{1-8}$ alkyl or aryl substituted with n occurrences of $R^2$. In some embodiments, $R^4$ is $C_{1-8}$ alkyl (e.g., methyl or ethyl) substituted with n occurrences of $R^2$.

In some embodiments, each $R^2$ is independently selected from halo, haloalkyl, alkyl, aryl, heteroaryl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted.

In some embodiments, n is 0. In some embodiments, n is 1. In some embodiments, $R^2$ is —$OR^a$. In some embodiments, $R^a$ is alkyl (e.g., methyl). In some embodiments, $R^2$ is optionally substituted heteroaryl. In some embodiments, $R^2$ is optionally substituted monocyclic heteroaryl (e.g., 3-pyridyl). In some embodiments, $R^2$ is optionally substituted aryl. In some embodiments, $R^2$ is optionally substituted monocyclic aryl (e.g., 4-chlorophenyl).

In some embodiments, $R^4$ is aryl (e.g., phenyl) substituted with n occurrences of $R^2$. In some embodiments, $R^4$ is phenyl substituted with n occurrences of $R^2$. In some embodiments, n is 0.

In some embodiments, n is 1. In some embodiments, $R^2$ is halo (e.g., fluoro or chloro). In some embodiments, $R^2$ is haloalkyl (e.g., trifluoromethyl). In some embodiments, $R^2$ is alkyl (e.g., methyl or ethyl). In some embodiments, $R^2$ is heteoaralkyl. In some embodiments, $R^2$ is optionally substituted monocyclic heteroaralkyl (e.g., methyl-4-trifluoromethyl-2-pyridyl). In some embodiments, $R^2$ is cyano. In some embodiments, $R^2$ is —$OR^a$. In some embodiments, $R^a$ is alkyl (e.g., methyl). In some embodiments, $R^2$ is —$COOR^b$. In some embodiments, $R^b$ is alkyl (e.g., ethyl). In some embodiments, $R^2$ is optionally substituted monocyclic heteroaryl. In some embodiments, $R^2$ is optionally substituted pyridyl. In some embodiments, $R^2$ is pyridyl substituted with haloalkyl (e.g., trifluoromethyl).

In some embodiments, n is 2. In some embodiments, both $R^2$ are halo (e.g., fluoro or chloro). In some embodiments, n is 2. In some embodiments, both $R^2$ are alkyl (e.g., methyl). In some embodiments, n is 2. In some embodiments, one $R^2$ is halo (e.g., fluoro or chloro) and one is alkyl (e.g., methyl). In some embodiments, n is 2. In some embodiments, one $R^2$ is halo and one is —$CONR^cR^{c'}$. In some embodiments, n is 2. In some embodiments, one $R^2$ is chloro and one is —$CONHR^{c'}$. In some embodiments, $R^c$ is alkyl (e.g., methyl or isopropyl). In some embodiments, n is 2. In some embodiments, one $R^2$ is alkyl and one is —$CONR^cR^{c'}$. In some embodiments, n is 2. In some embodiments, one $R^2$ is methyl and one is —$CONHR^{c'}$. In some embodiments, $R^{c'}$ is alkyl (e.g., methyl or isopropyl).

In some embodiments, n is 2. In some embodiments, one $R^2$ is haloalkyl (e.g., trifluoromethyl) and the other is —$OR^a$. In some embodiments, $R^a$ is alkyl (e.g., methyl). In some embodiments, n is 2. In some embodiments, one $R^2$ is halo and the other is —$OR^a$. In some embodiments, n is 2. In some embodiments, one $R^2$ is chloro and the other is —$OR^a$. In some embodiments, $R^a$ is optionally substituted heteroaryl. In some embodiments, n is 2. In some embodiments, both $R^2$ are —$OR^a$. In some embodiments, $R^a$ is alkyl (e.g., methyl). In some embodiments, $R^a$ is optionally substituted pyridyl. In some embodiments, $R^a$ is pyridyl substituted with haloalkyl (e.g., trifluoromethyl). In some embodiments, $R^a$ is optionally substituted heterocyclyl. In some embodiments, $R^a$ is an optionally substituted 5-membered heterocyclyl. In some embodiments, $R^a$ is optionally substituted pyrrolidinyl. In some embodiments, $R^a$ is N-methyl pyrrolidinyl. In some embodiments, $R^a$ is:

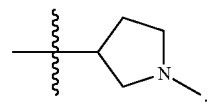 [SMILES: *C1CCN(C)C1]

In some embodiments, n is 2. In some embodiments, two $R^2$, together with the carbon atoms to which they are attached, form a 5-membered heterocyclic ring. In some embodiments, two $R^2$, together with the phenyl ring to which they are attached, form the following structure:

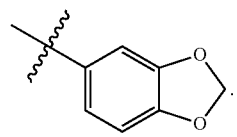 [SMILES: *c1ccc2c(c1)OCO2]

In some embodiments, n is 3. In some embodiments, each $R^2$ is halo (e.g., fluoro). In some embodiments, n is 3. In some embodiments, two $R^2$ are halo and one $R^2$ is —$CONR^cCR^{c'}$. In some embodiments, two $R^2$ are chloro and one $R^2$ is —$CONHR^{c'}$. In some embodiments, $R^{c'}$ is alkyl (e.g., methyl or isopropyl). In some embodiments, one $R^2$ is chloro, one $R^2$ is bromo, and one $R^2$ is —$CONHR^{c'}$. In some embodiments, $R^{c'}$ is alkyl (e.g., methyl or isopropyl). In some embodiments, n is 3. In some embodiments, one $R^2$ is halo, one $R^2$ is alkyl, and one $R^2$ is —$CONR^cR^{c'}$. In some embodiments, one $R^2$ is chloro, one $R^2$ is methyl, and one $R^2$ is —$CONHR^{c'}$. In some embodiments, $R^{c'}$ is alkyl (e.g., methyl or isopropyl). In some embodiments, one $R^2$ is bromo, one $R^2$ is methyl, and one $R^2$ is —$CONHR^{c'}$. In some embodiments, $R^c$ is alkyl (e.g., methyl or isopropyl).

In some embodiments, $R^3$ is halo (e.g., chloro or bromo). In some embodiments, $R^3$ is haloalkyl (e.g., trifluoromethyl). In some embodiments, $R^3$ is —$OR^4$. In some embodiments, $R^a$ is haloalkyl (e.g., difluoromethoxy, trifluoromethoxy or trifluoroethoxy). In some embodiments, $R^a$ is —$CH_2CF_3$.

In another aspect, the invention features a pharmaceutical composition comprising a compound of formula (Va):

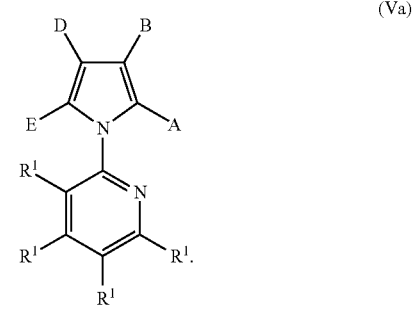

(Va)

wherein
B and D are each independently selected from H and $SO_2NR^4R^5$; wherein at least one of B or D is —$SO_2$—$NR^4R^5$;
A and E are each independently selected from H and $R^3$;
each $R^1$ is independently selected from hydrogen, halo and haloalkyl;
$R^4$ is hydrogen, $C_{1-8}$ alkyl, and aryl, substituted with n occurrences of $R^2$;

each R² is independently selected from halo, haloalkyl, alkyl, aryl, heteroaryl, aralkyl, heteroaralkyl, cyano, —OR^a, —COOR^b and —CONR^cR^c'; wherein two R², together with the carbons to which they are attached, may form an optionally substituted ring, each of which can be further substituted;

each R³ is independently selected from halo, haloalkyl and —OR^a;

R⁵ is hydrogen or C_{1-8} alkyl;

R^a is independently selected from alkyl, haloalkyl, optionally substituted heteroaryl and optionally substituted heterocyclyl;

each R^b is independently alkyl;

each R^c is independently selected from hydrogen and alkyl; and n is 0, 1, 2, or 3.

In another aspect, the invention features a method of treating a disorder described herein (e.g., cancer) comprising administering to a subject a compound of formula (V) or (Va) as described herein or a pharmaceutically acceptable salt thereof.

In another aspect, the invention features a method of preventing (e.g., preventing the onset of at least one symptom) or delaying the onset of a disorder described here (e.g., cancer) comprising administering to a subject a compound of formula (V) or (Va) as described herein or a pharmaceutically acceptable salt thereof.

In some embodiments, A and E are each H.

In some embodiments, B is SO₂NR⁴R⁵ and D is H. In some embodiments, B is H and D is SO₂NR⁴R⁵.

In one aspect, the present invention features a compound or pharmaceutically acceptable salt thereof of formula (VI):

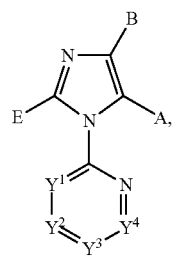

(VI)

wherein
A, B and E are each independently selected from H, —SO₂—NR⁴R⁵ and R³; wherein at least one of A, B or E is —SO₂—NR⁴R⁵;

Y¹, Y², Y³ and Y⁴ are each independently selected from N and CR¹, wherein at least one of Y¹, Y², Y³ and Y⁴ are N;

each R⁴ is independently selected from C_{1-8} alkyl, aryl and heteroaryl, each of which is substituted with n occurrences of R²;

each R⁵ is independently hydrogen or C_{1-8} alkyl;

each R¹ is independently selected from hydrogen, C_{1-8} alkyl, C_{1-8} terminal alkynyl, C_{1-8} alkoxy, halogen, haloalkyl and haloalkoxy;

each R² is independently selected from halo, haloalkyl, C_{1-4} alkyl, C_{2-4} alkenyl, C_{2-4} alknynyl, aryl, heteroaryl, aralkyl, heteroaralkyl, cyano, —OR^a, —COOR^b and —CONR^cR^c'; wherein two R², together with the carbons to which they are attached, may form an optionally substituted ring, each of which can be further substituted;

each R³ is independently selected from C_{1-8} alkyl, —OR^a, halogen, haloalkyl, haloalkoxy and optionally substituted heteroaryl;

each R^a is independently selected from alkyl, haloalkyl, optionally substituted heteroaryl and optionally substituted heterocyclyl;

each R^b is independently alkyl; and each R^c is independently selected from hydrogen and alkyl; and n is 0, 1, 2 or 3.

In some embodiments, at least one of Y¹, Y², Y³ and Y⁴ is N. In some embodiments, at least one of Y¹, Y², Y³ and Y⁴ are CH. In some embodiments, Y¹ is N. In some embodiments, Y³ is N.

In some embodiments, each R¹ is independently hydrogen.

In some embodiments, the invention features a compound of formula (VIa):

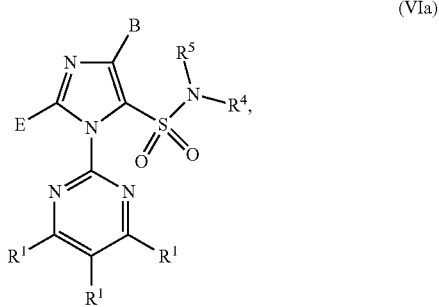

(VIa)

wherein n, B, E, R¹, R², R³, R⁴ and R⁵ are defined as above.

In some embodiments, the invention features a compound of formula (VIb):

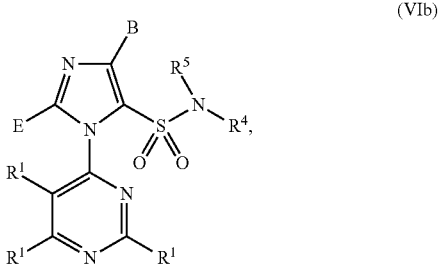

(VIb)

wherein n, B, E, R¹, R², R³, R⁴ and R⁵ are defined as above.

In some embodiments, B and E are each independently selected from H.

In some embodiments, R⁵ is hydrogen.

In some embodiments, each R¹ is independently hydrogen. In some embodiments, each R¹ is independently selected from C_{1-8} alkyl, halogen or haloalkyl. In some embodiments, each R¹ is independently selected from halogen or haloalkyl. In some embodiments, each R¹ is independently selected from halogen (e.g., chlorine or fluorine). In some embodiments, each R¹ is independently haloalkyl (e.g., trifluoroalkyl).

In some embodiments, R⁴ is selected from aryl or heteroaryl. In some embodiments, R⁴ is aryl substituted with n occurrences of R². In some embodiments, R⁴ is C_{5-8} monocyclic aryl or C_{8-14} bicyclic aryl. In some embodiments, R⁴ is C_{5-8} monocyclic aryl (e.g., optionally substituted phenyl). In some embodiments, R⁴ is phenyl substituted with n occurrences of R². In some embodiments, R² is heteroaryl substituted with n occurrences of R². In some embodiments, R⁴ is a 5-8 membered heteroaryl or 8-14 membered heteroaryl. In some embodiments, R⁴ is an 8-12 membered heteroaryl (e.g., 5-quinolyl or 6-quinolyl). In some embodiments, R⁴ is quinolyl (e.g., 5-quinolyl or 6-quinolyl) substituted with n occurrences of R².

In some embodiments, n is 0. In some embodiments, n is 1.

In some embodiments, R² is halo, $C_{1-4}$ alkyl or haloalkyl, each of which can be further substituted.

In some embodiments, R² is $C_{1-4}$ alkyl (e.g., ethyl). In some embodiments, R² is halo (e.g., fluoro or chloro). In some embodiments, R² is haloalkyl (e.g., trifluoromethyl).

In some embodiments, n is 2. In some embodiments, both R² are $C_{1-4}$ alkyl (e.g., methyl). In some embodiments, n is 2. In some embodiments, both R² are halo (e.g., fluoro or chloro). In some embodiments, n is 2. In some embodiments, one R² is haloalkyl (e.g., trifluoroalkyl) and the other R² is —OR$^a$. In some embodiments, R$^a$ is alkyl (e.g., methyl or ethyl). In some embodiments, n is 2. In some embodiments, on R² is halo (e.g., fluoro or chloro) and the other R² is $C_{1-4}$ alkyl (e.g., methyl or ethyl).

In some embodiments, n is 2. In some embodiments, two R², together with the carbon atoms to which they are attached, form a 5-membered heterocyclic ring. In some embodiments, two R², together with the phenyl ring to which they are attached, form the following structure:

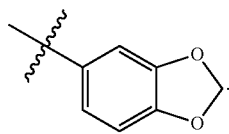 [SMILES: *c1ccc2c(c1)OCO2]

In some embodiments, n is 3. In some embodiments, all R² are halo (e.g., fluoro or chloro).

In another aspect, the invention features a pharmaceutical composition comprising a compound selected from Formula (VI), (VIa) or (VIb) as described herein or a pharmaceutically acceptable salt thereof.

In another aspect, the invention features a method of treating a disorder described herein (e.g., cancer) comprising administering to a subject a compound of formula (VI), (VIa) or (VIb) as described herein or a pharmaceutically acceptable salt thereof.

In another aspect, the invention features a method of preventing (e.g., preventing the onset of at least one symptom) or delaying the onset of a disorder as described herein (e.g., cancer) comprising administering to a subject a compound of formula (VI), (VIa) or (VIb) as described herein or a pharmaceutically acceptable salt thereof.

In one aspect, the present invention features a compound or pharmaceutically acceptable salt thereof of formula (VII):

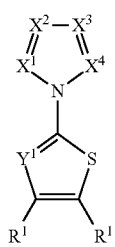

(VII)

wherein
X¹ is N or CE;
X² is N or CD;
X³ is N or CB;
X⁴ is N or CA, wherein at least one of X¹, X², X³ and X⁴ is N and at least one of X¹, X², X³, X⁴, is C—SO₂—NR⁴R⁵;
A, B, D and E are each independently selected from H, R³ and —SO₂—NR⁴R⁵;
Y¹ is selected from N and CR¹;
each R⁴ is independently selected from $C_{1-8}$ alkyl, aryl and heteroaryl, each of which is substituted with n occurrences of R²;
R⁵ is hydrogen or $C_{1-8}$ alkyl;
each R¹ is independently selected from hydrogen, $C_{1-8}$ alkyl, $C_{1-8}$ terminal alkynyl, $C_{1-8}$ alkoxy, halogen, haloalkyl and haloalkoxy;
each R² is independently selected from halo, haloalkyl, $C_{1-4}$ alkyl, $C_{2-4}$ alkenyl, $C_{2-4}$ alkynyl, aryl, heteroaryl, aralkyl, heteroaralkyl, cyano, —OR$^a$, —COOR$^b$ and —CONR$^c$R$^{c'}$; wherein two R², together with the carbons to which they are attached, may form an optionally substituted ring, each of which can be further substituted;
each R³ is independently selected from $C_{1-8}$ alkyl, —OR$^a$, halogen, haloalkyl, haloalkoxy and optionally substituted heteroaryl;
each R$^a$ is independently selected from alkyl, haloalkyl, optionally substituted heteroaryl and optionally substituted heterocyclyl;
each R$^b$ is independently alkyl; and
each R$^c$ is independently selected from hydrogen and alkyl; and
n is 0, 1, 2 or 3.

In some embodiments, the invention features a compound of formula (VIIa):

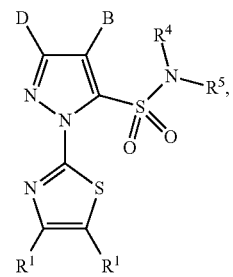

(VIIa)

wherein n, B, D, R¹, R⁴, R² and R⁵ are defined as in formula (VII).

In some embodiments, the invention features a compound of formula (VIIa):

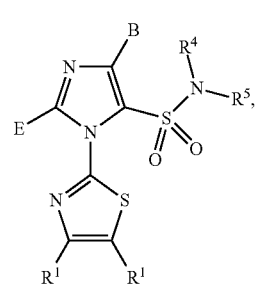

(VIIb)

wherein n, B, E, R¹, R⁴, R² and R⁵ are defined as in formula (VII).

In some embodiments, the invention features a compound of formula (VIIb):

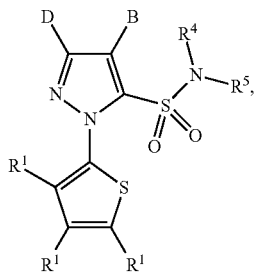

(VIIc)

wherein n, B, D, $R^1$, $R^4$, $R^2$ and $R^5$ are defined as in formula (VII).

In some embodiments, the invention features a compound of formula (VIIa):

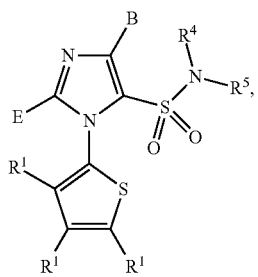

(VIId)

wherein n, B, E, $R^1$, $R^4$, $R^2$ and $R^5$ are defined as in formula (VII).

In some embodiments, B and E are each independently selected from H.

In some embodiments, B and D are each independently selected from H.

In some embodiments, $R^5$ is hydrogen.

In some embodiments, each $R^1$ is independently hydrogen. In some embodiments, each $R^1$ is independently selected from $C_{1-8}$ alkyl, halogen or haloalkyl. In some embodiments, each $R^1$ is independently selected from halogen or haloalkyl. In some embodiments, each $R^1$ is independently selected from halogen (e.g., chlorine or fluorine). In some embodiments, each $R^1$ is independently haloalkyl (e.g., trifluoroalkyl).

In some embodiments, $R^4$ is selected from aryl or heteroaryl. In some embodiments, $R^4$ is aryl substituted with n occurrences of $R^2$. In some embodiments, $R^4$ is $C_{5-8}$ monocyclic aryl or $C_{8-14}$ bicyclic aryl. In some embodiments, $R^4$ is $C_{5-8}$ monocyclic aryl (e.g., optionally substituted phenyl). In some embodiments, $R^4$ is phenyl substituted with n occurrences of $R^2$.

In some embodiments, n is 0. In some embodiments, n is 1.

In some embodiments, $R^2$ is halo, $C_{1-4}$ alkyl or haloalkyl, each of which can be further substituted.

In some embodiments, $R^2$ is $C_{1-4}$ alkyl (e.g., methyl or ethyl). In some embodiments, $R^2$ is halo (e.g., fluoro or chloro).

In some embodiments, n is 2. In some embodiments, both $R^2$ are $C_{1-4}$ alkyl (e.g., methyl or ethyl). In some embodiments, n is 2. In some embodiments, both $R^2$ are halo (e.g., fluoro or chloro). In some embodiments, n is 2. In some embodiments, one $R^2$ is haloalkyl (e.g., trifluoroalkyl) and the other $R^2$ is $-OR^a$. In some embodiments, $R^a$ is alkyl (e.g., methyl or ethyl). In some embodiments, n is 2. In some embodiments, one $R^2$ is $C_{1-4}$ alkyl (e.g., methyl or ethyl) and the other $R^2$ is halo (e.g., fluoro or chloro).

In some embodiments, n is 2. In some embodiments, two $R^2$, together with the carbon atoms to which they are attached, form a 5-membered heterocyclic ring. In some embodiments, two $R^2$, together with the phenyl ring to which they are attached, form the following structure:

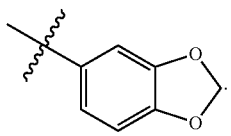 [SMILES: *c1ccc2c(c1)OCO2]

In some embodiments, n is 3. In some embodiments, all $R^2$ are halo (e.g., fluoro or chloro).

In another aspect, the invention features a pharmaceutical composition comprising a compound selected from formula (VII), (VIIa), (VIIb), (VIIc) or (VIId) as described herein or a pharmaceutically acceptable salt thereof.

In another aspect, the invention features a method of treating a disorder described herein (e.g., cancer) comprising administering to a subject a compound of formula (VII), (VIIa), (VIIb), (VIIc) or (VIId) as described herein or a pharmaceutically acceptable salt thereof.

In another aspect, the invention features a method of preventing (e.g., preventing the onset of at least one symptom) or delaying the onset of a disorder described here (e.g., cancer) comprising administering to a subject a compound of formula (VII), (VIIa), (VIIb), (VIIc) or (VIId) as described herein or a pharmaceutically acceptable salt thereof.

In one aspect, the invention features a method of modulating (e.g., increasing or decreasing) the level of PKM2 activity and/or glycolysis (e.g., modulating the endogenous ability of a cell in the patient to down regulate PKM2) in a patient in need thereof. The method comprises the step of administering an effective amount of a compound described herein to the patient in need thereof, thereby modulating (e.g., increasing or decreasing) the level of PKM2 activity and/or glycolysis in the patient. In some embodiments of the invention an activator is used to maintain PKM2 in its active conformation or activate pyruvate kinase activity in proliferating cells as a means to divert glucose metabolites into catabolic rather than anabolic processes in the patient.

In another aspect, the invention features a method of regulating cell proliferation in a patient in need thereof. The method comprises the step of administering an effective amount of a compound described herein to the patient in need thereof, thereby regulating cell proliferation in the patient. E.g., this method can modulate growth of a transformed cell, e.g., a cancer cell, or generally modulate growth in a PKM2-dependent cell that undergoes aerobic glycolysis.

In another aspect, the invention features a method of treating a patient suffering from or susceptible to a disease or disorder associated with the function of PKM2 in a patient in need thereof. The method comprises the step of administering an effective amount of a compound described herein to the patient in need thereof, thereby treating, preventing or ameliorating the disease or disorder in the patient. In another embodiment the modulator is provided in a pharmaceutical composition.

In another embodiment the method includes identifying or selecting a patient who would benefit from modulation (e.g., activation or inhibition) of PKM2. E.g., the patient can be identified on the basis of the level of PKM2 activity in a cell of the patient (e.g., as opposed to merely being in need of treatment of the disorder itself, e.g., cancer). In another embodiment the selected patient is a patient suffering from or susceptible to a disorder or disease identified herein, e.g., a disorder characterized by unwanted cell growth or proliferation, e.g., cancer, obesity, diabetes, atherosclerosis, restenosis, and autoimmune diseases.

In one aspect, the invention features a method of evaluating a candidate compound the method comprising:

optionally supplying the candidate compound;

contacting the compound with a cell, e.g., a cell having an intact plasma membrane;

evaluating the ability of the compound to interact intracellularly with, e.g., to form a complex with, to bind, e.g., specifically to, or to modulate (e.g., activate or inhibit) the activity of, a target kinase, e.g., pyruvate kinase, e.g., PKM2;

thereby evaluating the candidate compound.

In some embodiments, evaluating the candidate compound comprises evaluating the candidate compound for use as an anti-proliferative or anti-cancer agent and the ability of the candidate compound to interact intracellulary with the target compound is correlated to efficacy as an anti-proliferative or anti-cancer agent.

In some embodiments, evaluating the candidate compound comprises evaluating the ability of the candidate compound cross the cell membrane and the ability of the candidate compound to interact intracellulary with the target compound is correlated to with ability of the candidate compound to cross the cell membrane.

In some embodiments, evaluating the candidate compound comprises evaluating the ability of the candidate compound to modulate any of the following properties: a conformational state in the target kinase, binding of the target kinase to an endogenous modulator of target kinase activity, e.g., FBP or a phosphotyrsine containing polypeptide, or other property of a target kinase disclosed herein, and the ability of the candidate compound to interact with the target compound is correlated with one or more of said properties.

In some embodiments, the method further comprises separating the cell from candidate compound that has not entered the cell, e.g., by washing the cell or removing the cell from an animal to which the candidate compound has been administered.

In some embodiments, the method further comprises lysing (e.g., by disrupting or dissolving the cell membrane) the cell, e.g., prior to evaluating the ability of the candidate compound to interact with the target kinase.

In some embodiments, contacting the candidate compound with a cell comprises contacting the candidate compound with a whole animal, a tissue that is not part of a whole animal, an organ which is not part of a whole animal or a cell which is not part of a whole animal.

In some embodiments, the cell is a cultured cell, e.g., a primary cell, a secondary cell.

In some embodiments, the cell is a mammal, primate, human, rodent, mouse, rat, or hamster cell.

In some embodiments, the cell is a tumor or transformed cell, e.g., a solid tumor cell.

In some embodiments, a plurality of target compounds are evaluated, e.g., at least 10, 20, 50, 100, or 500 candidate compounds are evaluated.

In some embodiments, a plurality of candidate compounds are evaluated simultaneously, e.g., wherein each of a plurality of candidate compounds is evaluated individually but simultaneously, or wherein a plurality of candidate compounds are pooled and contacted with the same cell or same aliquot of cells.

In some embodiments, a plurality of candidate compounds are evaluated in an automated device.

In some embodiments, evaluating a candidate compound comprises providing a value for the ability of the candidate compound to interact with the target kinase and, optionally, comparing that value to a predetermined value, e.g., a value for a positive and or negative control.

In some embodiments, the method further comprises selecting a candidate compound have a value for interacting with the target kinase which has a preselected relationship with a reference value, e.g., the value for the candidate compound exceeds a preselected minimum value, e.g., a preselected minimum value for activation of the target kinase.

In some embodiments, the method further comprises evaluating, e.g., confirming, the ability of a candidate compound (e.g., a candidate compound which meets a predetermined level of interaction (e.g., complex formation, specific binding, or modulation (e.g., activation or inhibition) in the evaluating step) to interact with, e.g., to form a complex with, to bind specifically to, or to modulate (e.g., activate or inhibit) the activity of the target kinase in a second method.

In some embodiments, the method further comprises selecting a candidate compound and repeating the evaluation under the same or different conditions, e.g., at the same or a different concentration.

In some embodiments, the method further comprises selecting a candidate compound evaluated in a cell other than a whole animal and confirming the activity determined in the cell-based assay by evaluation in a whole animal.

In some embodiments, the method further comprises selecting a candidate compound and confirming the activity determined in the evaluation by a second, different assay.

In some embodiments, a plurality of structurally related candidate candidates are evaluated, e.g., a plurality of candidate candidates having a common core or scaffold.

In some embodiments, the method comprises providing a plurality of second generation candidate candidates which are analogs of a candidate compound.

In some embodiments, the method comprises evaluating a first candidate compound, comparing the structure of the first candidate compound to a second candidate compound and evaluating the second candidate compound In some embodiments, the candidate compound is contacted with cultured cells, e.g., cultured cells having a preselected level of confluency, e.g., from about 60% to about 95%, preferably from about 70% to about 90% confluent.

In some embodiments, the candidate compound is contacted with the cell for a preselected length of time, e.g., a time period sufficient to allow a positive control to enter the cell and interact with the target kinase.

In some embodiments, the contacting step comprises contacting the compound with the cell for at least about 0.1, 0.5, 1, 2, 3, 4, 5, or 6 hours.

In some embodiments, the compound forms a complex with the target kinase.

In some embodiments, the compound binds, e.g., specifically to the target kinase.

In some embodiments, the target kinase is PKM2 and the candidate compound induces a conformational change (e.g., from a non-activated or less activated conformation to an activated or more activated conformation or from an activated or more activated conformation to a non-activated or less activated conformation) in the target kinase.

In some embodiments, the target kinase is PKM2 and the candidate compound increases the activity of PKM2.

In some embodiments, the target kinase is PKM2 and the candidate compound decreases the activity of PKM2.

In some embodiments, the method further comprises evaluating the presence and/or amount of lactate, e.g., in the media.

In some embodiments, the lysing step comprises snap-freezing the cell, e.g., on dry ice.

In some embodiments, the lysing step comprises adding a lysis buffer, e.g., a detergent-containing (e.g., Triton-containing) lysis buffer (e.g., a lysis buffer described in Table 3), to the cell.

In some embodiments, the detergent is used at a concentration that does not disrupt the interaction (e.g., binding) between the compound and the kinase, e.g., pyruvate kinase, e.g., PKM2, e.g., at no more than about 0.1, 0.5, 1, 1.5, 2, or 5%.

In one aspect, the invention features a method of evaluating a candidate compound the method comprising:
  optionally supplying the candidate compound;
  contacting the candidate compound with a cell, which cell is outside an animal, e.g., a cell having an intact plasma membrane;
  separating the cell from candidate compound that has not entered the cell;
  lysing said cell under conditions that do not abolish the binding of the candidate compound to PKM2; and
  evaluating the ability of the compound to interact intracellularly with, e.g., to form a complex with, to bind, e.g., specifically to, or to modulate (e.g., activate or inhibit) the activity of PKM2;
  thereby evaluating the candidate compound.

In one aspect, the invention features a method of evaluating a candidate compound the method comprising:
  optionally supplying the candidate compound;
  contacting the candidate compound with a cell which is part of a whole animal;
  lysing said cell under conditions that do not abolish the binding of the candidate compound to PKM2; and
  evaluating the ability of the compound to interact intracellularly with, e.g., to form a complex with, to bind, e.g., specifically to, or to modulate (e.g., activate or inhibit) the activity of PKM2;
  thereby evaluating the candidate compound.

In another embodiment the compound described herein is administered at a dosage and frequency sufficient to increase lactate production or oxidative phosphorylation.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, and —$CH_2CH_2CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively. The term "aralkylamino" refers to a —NH(aralkyl) radical. The term alkylaminoalkyl refers to a (alkyl)NH-alkyl-radical; the term dialkylaminoalkyl refers to a (alkyl)$_2$N-alkyl-radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted (e.g., by one or more substituents). The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any ring atom can be substituted (e.g., by one or more substituents). The cycloalkenyl groups can contain fused rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom may optionally be the point of attachment of the heterocycloalkenyl substituent. Any ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "selective" is meant at least 2-fold, 3-fold, 4-fold, 5-fold, 6-fold, or 10-fold greater modulation (e.g., inhibition) of M2 than M1.

The term "activator" as used herein means an agent that (measurably) increases the activity of a pyruvate kinase (e.g., PKM2) or causes pyruvate kinase (e.g., PKM2) activity to increase to a level that is greater than PKM2's basal levels of activity. For example, the activator may mimic the effect caused by a natural ligand (e.g., FBP). The activator effect caused by the agent may be to the same, or to a greater, or to a lesser extent than the activating effect caused by a natural ligand, but the same type of effect is caused. Peptides, nucleic acids, and small molecules may be activators. An agent can be evaluated to determine if it is an activator by measuring either directly or indirectly the activity of the pyruvate kinase when subjected to the agent. The activity of the agent can be measured, for example, against a control substance. In some instances, the activity measured of the agent is for activation of PKM2. The activity of PKM2 can be measured, for example, by monitoring the concentration of a substrate such as ATP or NADH.

The term "inhibitor" as used herein means an agent that measurably slows, stops, decreases or inactivates the enzymatic activity of pyruvate kinase (e.g., PKM2) to decrease to a level that is less than the pyruvate kinase's (e.g., PKM2's) basal levels of activity. Inhibitors of pyruvate kinase (e.g., PKM2) may be peptides or nucleic acids. An agent can be evaluated to determine if it is an inhibitor by measuring either directly or indirectly the activity of the pyruvate kinase when subjected to the agent. The activity of the agent can be measured, for example, against a control substance. In some instances, the activity measured of the agent is for inhibition of PKM2. The activity of PKM2 can be measured, for example, by monitoring the concentration of a substrate such as ATP or NADH.

The term "modulate" refers to an increase or decrease, e.g., in the activity of an enzyme in response to exposure to a compound or composition described herein, e.g., the activation or inhibition of PKM2, in at least a sub-population of cells in a subject such that a desired end result is achieved (e.g., a therapeutic result). In some embodiments, a compound as described herein inhibits a target described herein, e.g., PKM2. In some embodiments, a compound as described herein is activates a target described herein, e.g., PKM2.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Compounds

Described herein are compounds and compositions that modulate PKM2, for example, activate or inhibit PKM2. Compounds that modulate PKM2, e.g., activate or inhibit PKM2, can be used to treat disorders such as neoplastic disorders (e.g., cancer) or fat related disorders (e.g., obesity).

Exemplary compounds include the compounds of Formulas (I), (II), (III), (IV), (V), (VI) and (VII) described herein. In some embodiments, a compound described herein modulates PKM2 by interacting (e.g., binding) with the FBP binding pocket. For example, a compound described herein can compete with FBP binding in PKM2.

In some embodiments a compound described herein has one or more properties described herein, e.g., one or more of the following properties: it is an allosteric modulator (e.g., inhibitor or activator); it modulates the release of FBP (e.g., inhibits or promotes); it is a modulator (e.g., agonist or antagonist) of FBP, e.g., an agonist which binds with a lower, about the same, or higher affinity than does FBP; it modulates (e.g., inhibits or promotes) the dissolution of tetrameric PKM2; it modulates (e.g., promotes or inhibits) the assembly of tetrameric PKM2; it selectively modulates (e.g., inhibits or activates) PKM2 over at least one other isoform of PK, e.g., it is selective for PKM2 over PKR, PKM1, or PKL; is has an affinity for PKM2 which is greater than its affinity for at least one other isoform of PK, e.g., PKR, PKM1, or PKL.

In another embodiment the activator of PKM2 utilized in the methods and compositions of this invention operates by or has one or more of the following mechanisms or properties:
 a. it is an allosteric activator of PKM2;
 b. it modulates (e.g., stabilizes or inhibits) the binding of FBP in a binding pocket of PKM2;
 c. it modulates (e.g., inhibits or promotes) the release of FBP from a binding pocket of PKM2;
 d. it is a modulator (e.g., an agonist or antagonist), e.g., an analog, of FBP, e.g., an agonist which binds PKM2 with a lower, about the same, or higher affinity than does FBP;
 e. it modulates (e.g., inhibits or promotes) the dissolution of tetrameric PKM2;
 f. it modulates (e.g., inhibits or promotes) the assembly of tetrameric PKM2;
 g. it modulates (e.g., stabilizes or inhibits) the tetrameric conformation of PKM2;
 h. it modulates (e.g., inhibits or promotes) the binding of a phosphotyrosine containing polypeptide to PKM2;
 i. it modulates (e.g., inhibits or promotes) the ability of a phosphotyrosine containing polypeptide to induce release of FBP from PKM2, e.g., by inducing a change in the conformation of PKM2, e.g., in the position of Lys 433, thereby hindering the release of FBP;
 k. it binds to or changes the position of Lys 433 relative to the FBP binding pocket;
 l. it selectively modulates (e.g., activates or inhibits) PKM2 over at least one other isoform of PK, e.g., it is selective for PKM2 over one or more of PKR, PKM1, or PKL;
 m. it has an affinity for PKM2 which is greater than its affinity for at least one other isoform of PK, e.g., PKR, PKM1, or PKL.

A compound described herein may be an activator of PKM2. Exemplary compounds are shown in Table 1. As shown in Table 1, A refers to an activator of PKM2 with an $EC_{50}$<100 nM. B refers to an activator of PKM2 with an $EC_{50}$ between 100 nM and 500 nM. C refers to an activator of PKM2 with an $EC_{50}$ between 500 nM and 1000 nM. D refers to an activator of PKM2 with an $EC_{50}$ between 1 μM and 10 μM. E refers to an activator of PKM2 with an $EC_{50}$>10 μM ND means not determined.

Ex vivo data is provided as follows: + refers to a compound having an activity of ≤1 μM; ++ refers to a compound having an activity of >1 μM; ND means not determined

TABLE 1

| Structure | PKM2_AC50 | Ex-Vivo_AC50 |
|---|---|---|
| 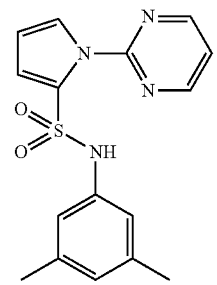 [SMILES: Cc1cc(C)cc(NS(=O)(=O)c2cccn2-c2ncccn2)c1] | A | + |
|  | D | ND |
| 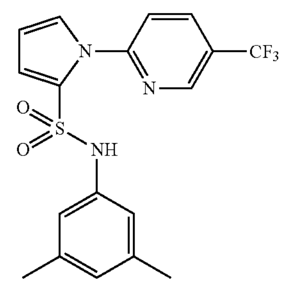 [SMILES: Cc1cc(C)cc(NS(=O)(=O)c2cccn2-c2ccc(C(F)(F)F)cn2)c1] | B | + |
|  | D | ND |

TABLE 1-continued
| Structure | Ex-PKM2_AC50 | Vivo_AC50 |
|---|---|---|
| 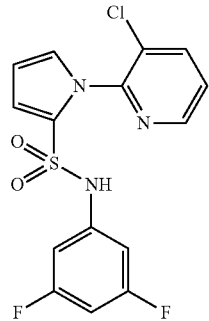 [SMILES: O=S(=O)(Nc1cc(F)cc(F)c1)c1cccn1-c1ncccc1Cl] | C | ND |
| 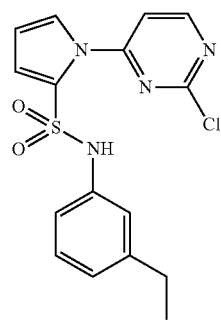 [SMILES: CCc1cccc(NS(=O)(=O)c2cccn2-c2ccnc(Cl)n2)c1] | B | ++ |
| 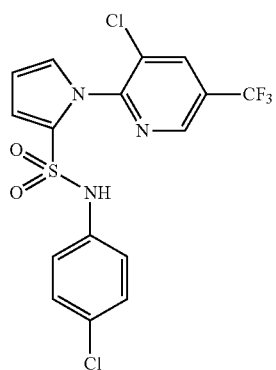 [SMILES: O=S(=O)(Nc1ccc(Cl)cc1)c1cccn1-c1ncc(C(F)(F)F)cc1Cl] | A | + |
| 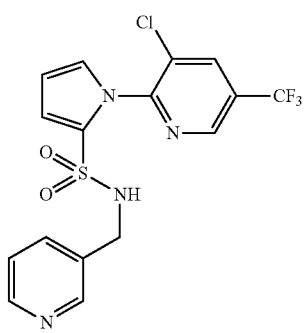 [SMILES: O=S(=O)(NCc1cccnc1)c1cccn1-c1ncc(C(F)(F)F)cc1Cl] | D | ND |
TABLE 1-continued
| Structure | Ex-PKM2_AC50 | Vivo_AC50 |
|---|---|---|
| 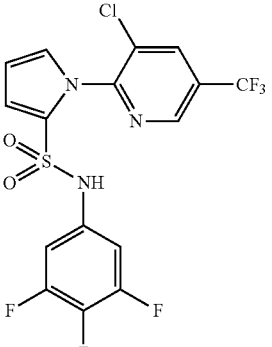 | B | ND |
| 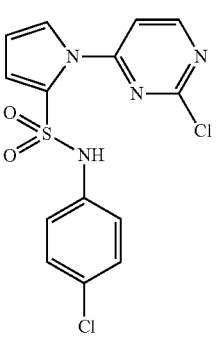 [SMILES: O=S(=O)(Nc1ccc(Cl)cc1)c1cccn1-c1ccnc(Cl)n1] | C | ND |
| 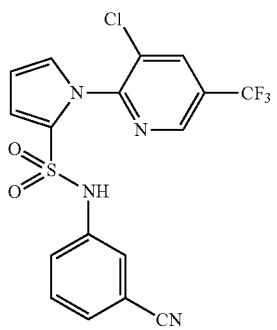 [SMILES: N#Cc1cccc(NS(=O)(=O)c2cccn2-c2ncc(C(F)(F)F)cc2Cl)c1] | B | ND |
| 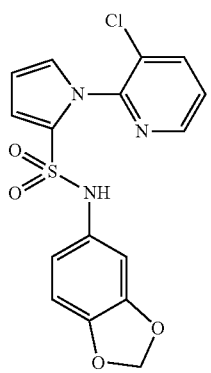 [SMILES: O=S(=O)(Nc1ccc2c(c1)OCO2)c1cccn1-c1ncccc1Cl] | A | + |

TABLE 1-continued
| Structure | PKM2_AC50 | Ex-Vivo_AC50 |
|---|---|---|
| 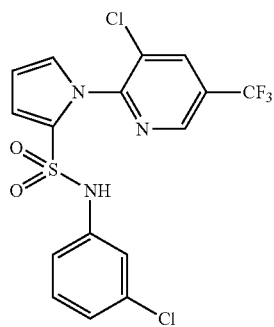 | A | + |
| 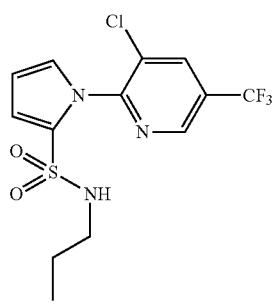 [SMILES: CCCNS(=O)(=O)c1cccn1-c1ncc(C(F)(F)F)cc1Cl] | D | ND |
| 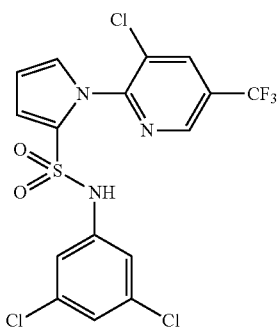 [SMILES: O=S(=O)(Nc1cc(Cl)cc(Cl)c1)c1cccn1-c1ncc(C(F)(F)F)cc1Cl] | D | ND |
| 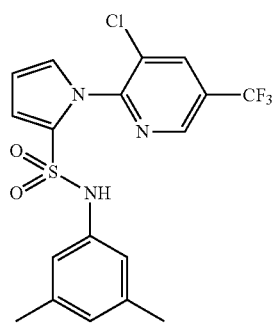 [SMILES: Cc1cc(C)cc(NS(=O)(=O)c2cccn2-c2ncc(C(F)(F)F)cc2Cl)c1] | A | + |
TABLE 1-continued
| Structure | PKM2_AC50 | Ex-Vivo_AC50 |
|---|---|---|
| 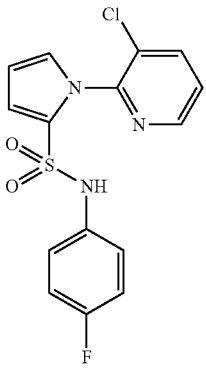 [SMILES: O=S(=O)(Nc1ccc(F)cc1)c1cccn1-c1ncccc1Cl] | D | ND |
| 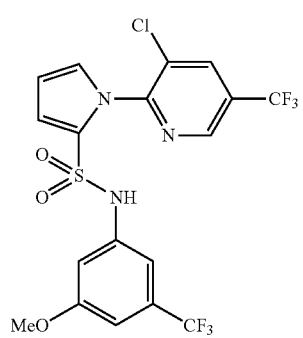 [SMILES: COc1cc(NS(=O)(=O)c2cccn2-c2ncc(C(F)(F)F)cc2Cl)cc(C(F)(F)F)c1] | C | ND |
| 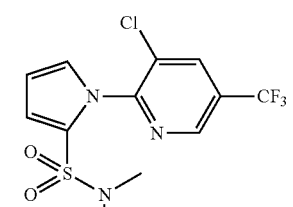 | E | ND |
| 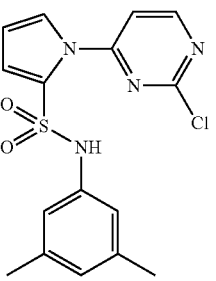 [SMILES: Cc1cc(C)cc(NS(=O)(=O)c2cccn2-c2ccnc(Cl)n2)c1] | A | ++ |
| 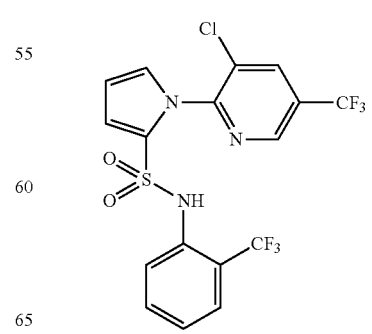 | D | ND |

TABLE 1-continued

| Structure | PKM2_AC50 | Ex-Vivo_AC50 |
|---|---|---|
| (3-ethylphenyl sulfonamide, 3-Cl-5-CF3-pyridinyl pyrrole) | C | ND |
| (4-F-3-methylphenyl sulfonamide, 3-Cl-5-CF3-pyridinyl pyrrole) | A | + |
| (3-methoxycarbonylphenyl sulfonamide, 3-Cl-5-CF3-pyridinyl pyrrole) | D | ND |
| (3,5-dimethoxyphenyl sulfonamide, 3-Cl-5-CF3-pyridinyl pyrrole) | B | ND |

TABLE 1-continued

| Structure | PKM2_AC50 | Ex-Vivo_AC50 |
|---|---|---|
| (4-methylphenyl sulfonamide, 3-Cl-5-CF3-pyridinyl pyrrole) | A | + |
| (4-Cl-3-methylphenyl sulfonamide, 3-Cl-5-CF3-pyridinyl pyrrole) | A | + |
| (4-F-phenyl sulfonamide, 5-CF3-pyridinyl pyrrole) | D | ND |
| (4-Cl-phenyl sulfonamide, 3-Cl-pyridinyl pyrrole) | B | + |

TABLE 1-continued
| Structure | Ex-PKM2_AC50 | Vivo_AC50 |
|---|---|---|
| 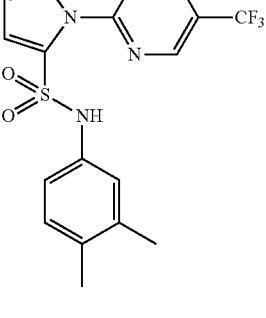 | A | + |
| 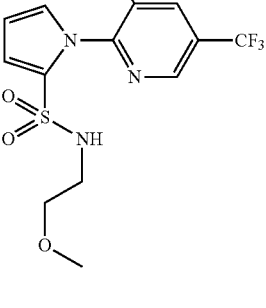 | E | ND |
| 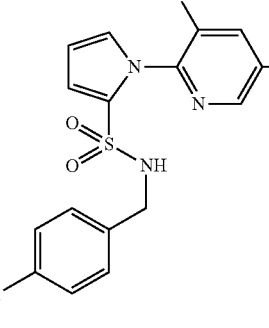 | E | ND |
| 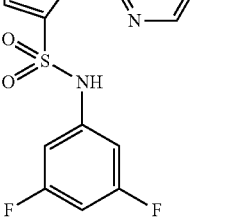 | A | + |
TABLE 1-continued
| Structure | Ex-PKM2_AC50 | Vivo_AC50 |
|---|---|---|
| | C | ND |
| 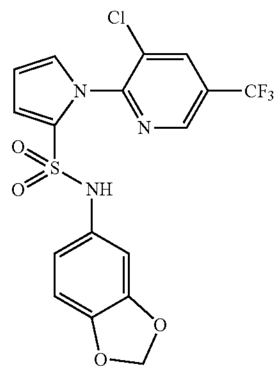 [SMILES: O=S(=O)(Nc1ccc2c(c1)OCO2)c1cccn1-c1ncc(C(F)(F)F)cc1Cl] | A | + |
| | C | ND |
| 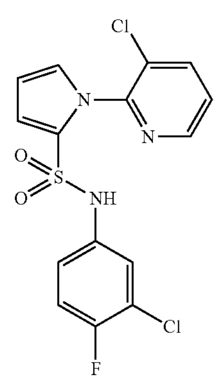 [SMILES: O=S(=O)(Nc1ccc(F)c(Cl)c1)c1cccn1-c1ncccc1Cl] | B | ND |

TABLE 1-continued
| Structure | PKM2_AC50 | Ex-Vivo_AC50 |
|---|---|---|
| 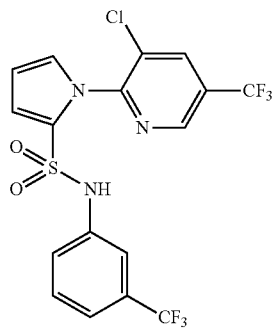 [SMILES: O=S(=O)(Nc1cccc(C(F)(F)F)c1)c1cccn1-c1ncc(C(F)(F)F)cc1Cl] | B | ND |
| 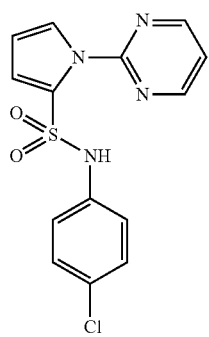 [SMILES: O=S(=O)(Nc1ccc(Cl)cc1)c1cccn1-c1ncccn1] | D | ND |
| 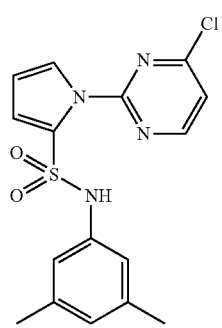 [SMILES: Cc1cc(C)cc(NS(=O)(=O)c2cccn2-c2nccc(Cl)n2)c1] | A | ++ |
| 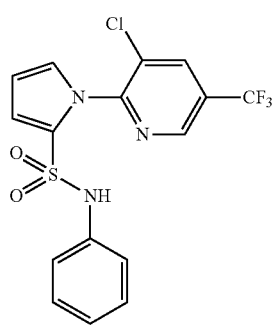 [SMILES: O=S(=O)(Nc1ccccc1)c1cccn1-c1ncc(C(F)(F)F)cc1Cl] | A | + |
TABLE 1-continued
| Structure | PKM2_AC50 | Ex-Vivo_AC50 |
|---|---|---|
| 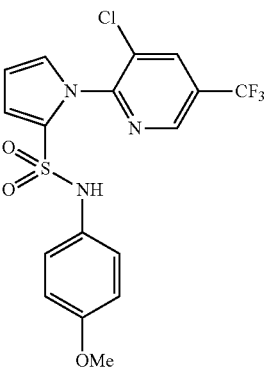 [SMILES: COc1ccc(NS(=O)(=O)c2cccn2-c2ncc(C(F)(F)F)cc2Cl)cc1] | B | ND |
| 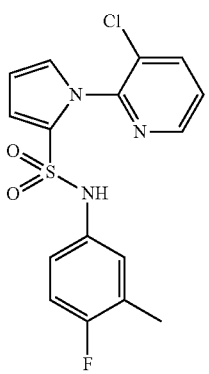 [SMILES: Cc1cc(NS(=O)(=O)c2cccn2-c2ncccc2Cl)ccc1F] | A | ND |
| 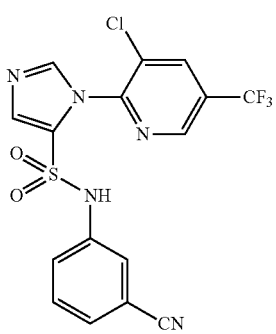 | D | ND |
| 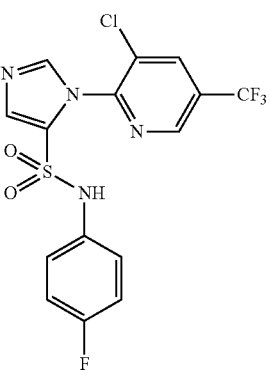 | D | ND |

TABLE 1-continued
| Structure | PKM2_AC50 | Ex-Vivo_AC50 |
|---|---|---|
| 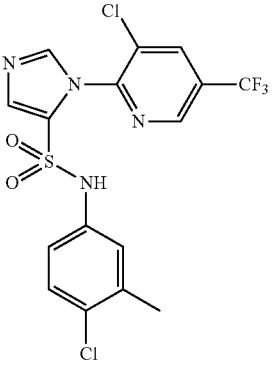 [SMILES: Cc1cc(NS(=O)(=O)c2cncn2-c2ncc(C(F)(F)F)cc2Cl)ccc1Cl] | B | + |
| 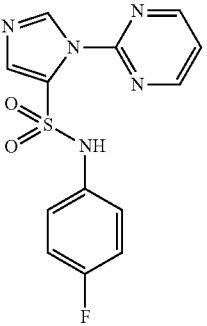 | D | ND |
| 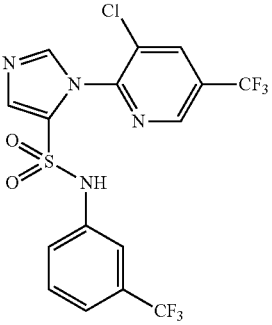 [SMILES: O=S(=O)(Nc1cccc(C(F)(F)F)c1)c1cncn1-c1ncc(C(F)(F)F)cc1Cl] | D | ND |
| 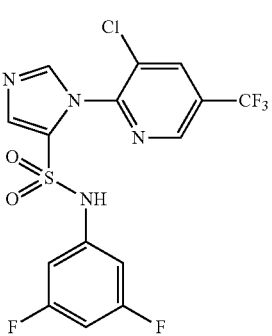 [SMILES: O=S(=O)(Nc1cc(F)cc(F)c1)c1cncn1-c1ncc(C(F)(F)F)cc1Cl] | C | ND |
TABLE 1-continued
| Structure | PKM2_AC50 | Ex-Vivo_AC50 |
|---|---|---|
| 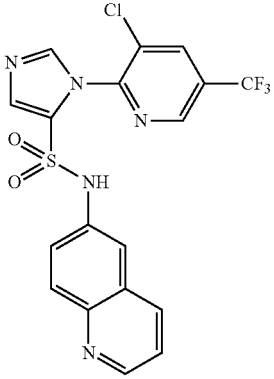 | D | ND |
| 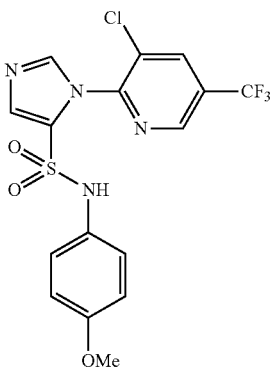 [SMILES: COc1ccc(NS(=O)(=O)c2cncn2-c2ncc(C(F)(F)F)cc2Cl)cc1] | D | ND |
| 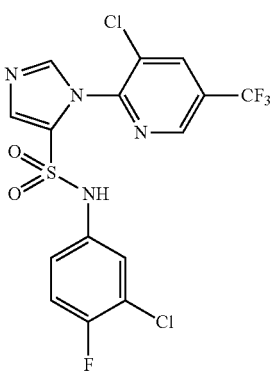 [SMILES: O=S(=O)(Nc1ccc(F)c(Cl)c1)c1cncn1-c1ncc(C(F)(F)F)cc1Cl] | B | + |
| 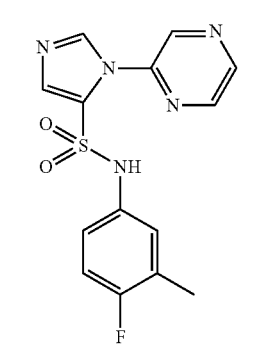 [SMILES: Cc1cc(NS(=O)(=O)c2cncn2-c2cnccn2)ccc1F] | B | ND |

TABLE 1-continued
| Structure | PKM2_AC50 | Ex-Vivo_AC50 |
|---|---|---|
| 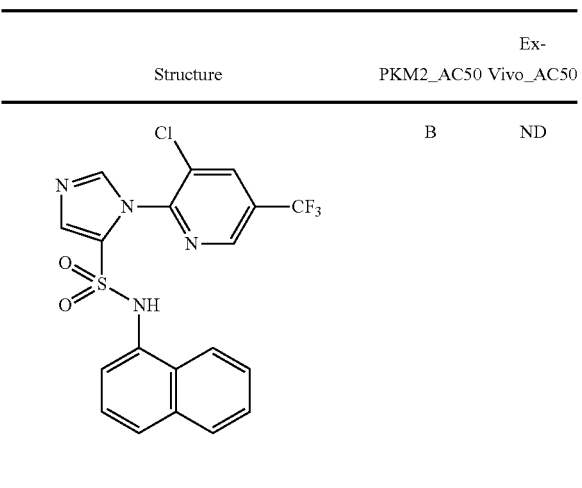 | B | ND |
| | D | ND |
| | D | ND |
| | D | ND |
TABLE 1-continued
| Structure | PKM2_AC50 | Ex-Vivo_AC50 |
|---|---|---|
| 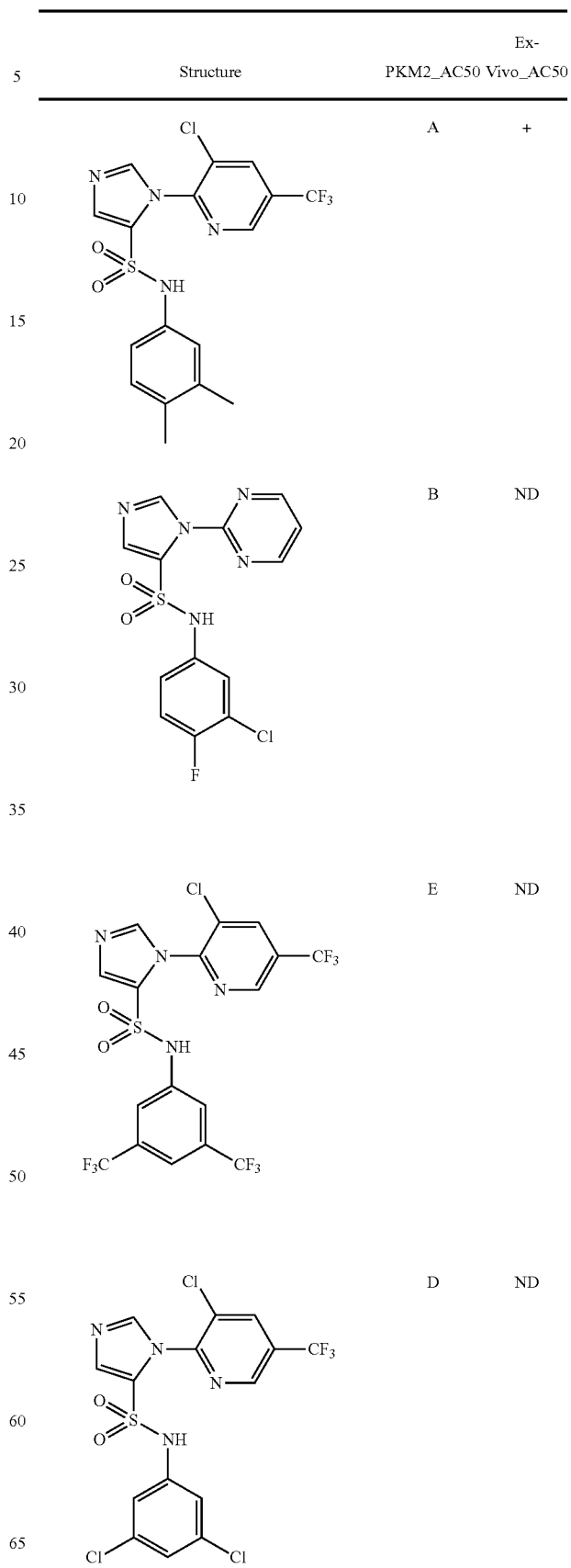 | A | + |
| 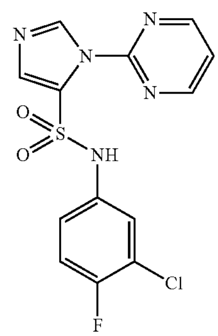 [SMILES: O=S(=O)(Nc1ccc(F)c(Cl)c1)c1cncn1-c1ncccn1] | B | ND |
| 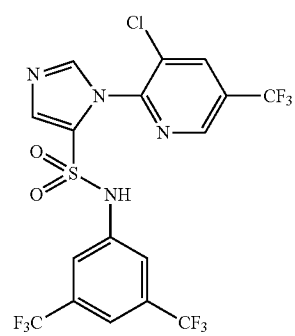 | E | ND |
| 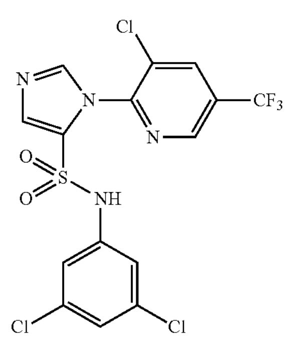 [SMILES: O=S(=O)(Nc1cc(Cl)cc(Cl)c1)c1cncn1-c1ncc(C(F)(F)F)cc1Cl] | D | ND |

TABLE 1-continued
| Structure | Ex-PKM2_AC50 | Vivo_AC50 |
|---|---|---|
| 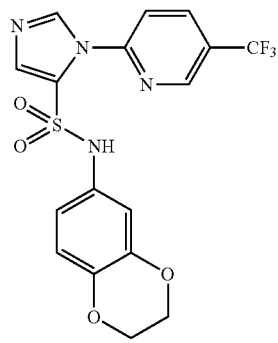 [SMILES: O=S(=O)(Nc1ccc2c(c1)OCCO2)c1cncn1-c1ccc(C(F)(F)F)cn1] | E | ND |
| 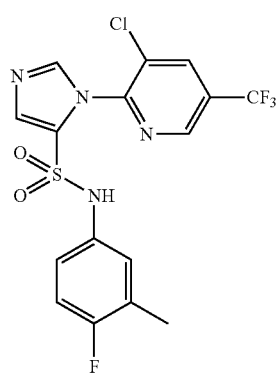 [SMILES: Cc1cc(NS(=O)(=O)c2cncn2-c2ncc(C(F)(F)F)cc2Cl)ccc1F] | A | + |
| 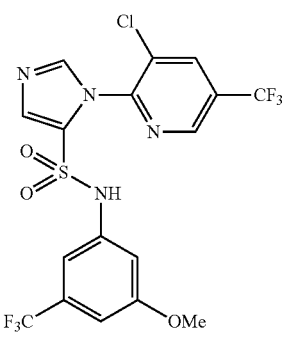 [SMILES: COc1cc(NS(=O)(=O)c2cncn2-c2ncc(C(F)(F)F)cc2Cl)cc(C(F)(F)F)c1] | D | ND |
| 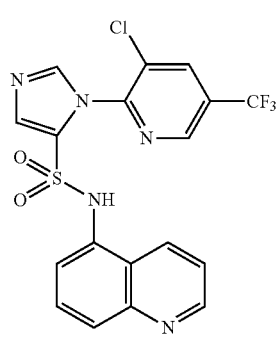 [SMILES: O=S(=O)(Nc1cccc2ncccc12)c1cncn1-c1ncc(C(F)(F)F)cc1Cl] | D | ND |
TABLE 1-continued
| Structure | Ex-PKM2_AC50 | Vivo_AC50 |
|---|---|---|
| 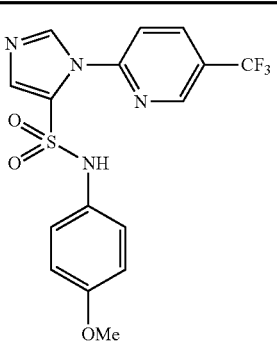 | D | ND |
| 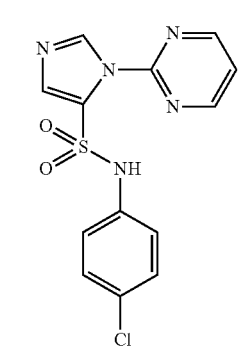 [SMILES: O=S(=O)(Nc1ccc(Cl)cc1)c1cncn1-c1ncccn1] | D | ND |
| 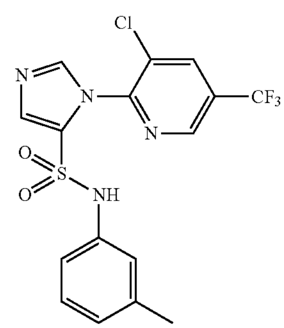 [SMILES: Cc1cccc(NS(=O)(=O)c2cncn2-c2ncc(C(F)(F)F)cc2Cl)c1] | A | + |
| 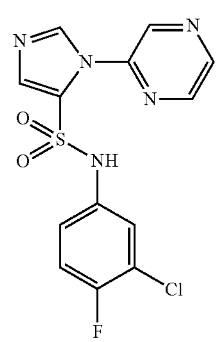 [SMILES: O=S(=O)(Nc1ccc(F)c(Cl)c1)c1cncn1-c1cnccn1] | B | ND |

TABLE 1-continued

| Structure | PKM2_AC50 | Ex-Vivo_AC50 |
|---|---|---|
| (3-chloro-5-CF₃-pyridinyl imidazole sulfonamide, N-2-naphthyl) | A | + |
| (5-CF₃-pyridinyl imidazole sulfonamide, N-4-fluorophenyl) | D | ND |
| (3-chloro-5-CF₃-pyridinyl imidazole sulfonamide, N-3,5-dimethoxyphenyl) | C | ND |
| (3-chloro-5-CF₃-pyridinyl imidazole sulfonamide, N-3,5-dimethylphenyl) | A | + |
| (pyrimidinyl imidazole sulfonamide, N-(4-fluoro-3-methylphenyl)) | A | ND |
| (3-chloro-5-CF₃-pyridinyl imidazole sulfonamide, N-3-chlorophenyl) | B | + |
| (5-CF₃-pyridinyl imidazole sulfonamide, N-3,5-dimethylphenyl) | B | ND |
| (3-chloro-5-CF₃-pyridinyl imidazole sulfonamide, N-3-ethylphenyl) | B | ND |
| (3-chloro-5-CF₃-pyridinyl pyrazole sulfonamide, N-4-methoxyphenyl) | D | ND |

TABLE 1-continued

| Structure | PKM2_AC50 | Ex-Vivo_AC50 |
|---|---|---|
| [pyrazole-SO2NH-(4-chlorophenyl); pyrazole N-linked to 3-chloro-5-(trifluoromethyl)pyridin-2-yl] | B | ND |
| [5-aminopyrazole sulfonamide with 3,5-dimethylphenyl-SO2NH; pyrazole N-linked to 3-chloro-5-(trifluoromethyl)pyridin-2-yl] | E | ND |
| [5-aminopyrazole sulfonamide with 4-chlorophenyl-SO2NH; pyrazole N-linked to 3-chloro-5-(trifluoromethyl)pyridin-2-yl] | ND | ND |
| [pyrazole-SO2NH-(4-chlorophenyl); pyrazole N-linked to 5-(trifluoromethyl)pyridin-2-yl] | D | ND |
| [pyrazole-SO2NH-(4-methoxyphenyl); pyrazole N-linked to 5-(trifluoromethyl)pyridin-2-yl] | E | ND |

TABLE 1-continued

| Structure | PKM2_AC50 | Ex-Vivo_AC50 |
|---|---|---|
| [pyrazole-SO2NH-(3,5-dimethylphenyl); pyrazole N-linked to 3-chloro-5-(trifluoromethyl)pyridin-2-yl] | A | + |
| [imidazole-SO2NH-(3,4,5-trifluorophenyl); imidazole N-linked to 3-chloro-5-(trifluoromethyl)pyridin-2-yl] | D | ND |
| [imidazole-SO2NH-(3-CF3-5-OMe-phenyl); imidazole N-linked to 3-chloro-5-(trifluoromethyl)pyridin-2-yl] | C | ND |
| [pyrrole-SO2NH-(3,4,5-trifluorophenyl); pyrrole N-linked to 3-chloro-5-(trifluoromethyl)pyridin-2-yl] | B | ND |

TABLE 1-continued
| Structure | PKM2_AC50 | Ex-Vivo_AC50 |
|---|---|---|
| 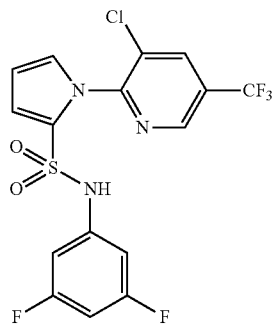 [SMILES: O=S(=O)(Nc1cc(F)cc(F)c1)c1cccn1-c1ncc(C(F)(F)F)cc1Cl] | A | + |
| 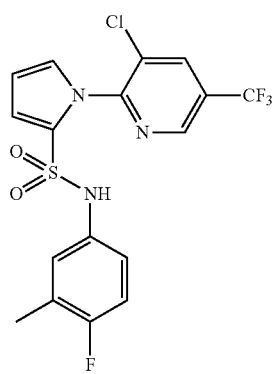 [SMILES: Cc1cc(NS(=O)(=O)c2cccn2-c2ncc(C(F)(F)F)cc2Cl)ccc1F] | A | + |
| 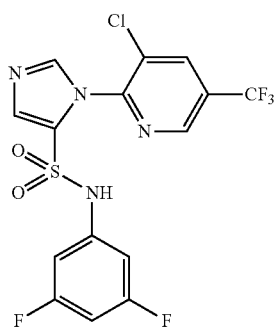 [SMILES: O=S(=O)(Nc1cc(F)cc(F)c1)c1cncn1-c1ncc(C(F)(F)F)cc1Cl] | C | ND |
| 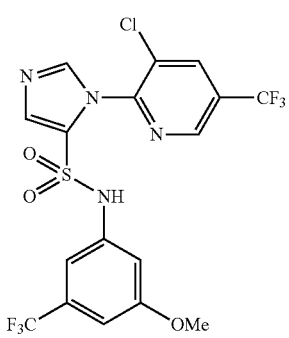 [SMILES: COc1cc(NS(=O)(=O)c2cncn2-c2ncc(C(F)(F)F)cc2Cl)cc(C(F)(F)F)c1] | D | ND |
TABLE 1-continued
| Structure | PKM2_AC50 | Ex-Vivo_AC50 |
|---|---|---|
| 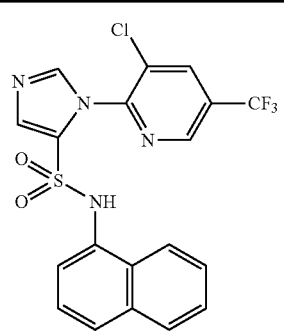 | B | ND |
| 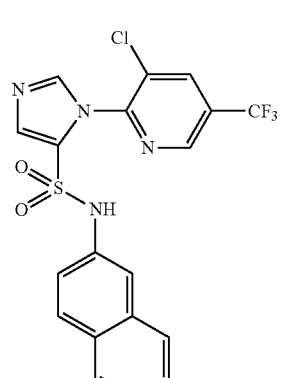 | B | + |
| 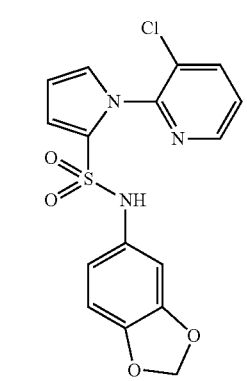 [SMILES: O=S(=O)(Nc1ccc2c(c1)OCO2)c1cccn1-c1ncccc1Cl] | A | + |
| 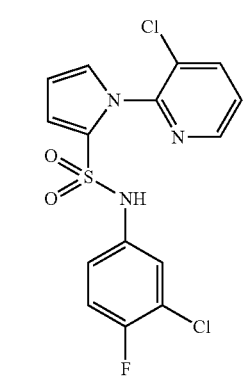 [SMILES: O=S(=O)(Nc1ccc(F)c(Cl)c1)c1cccn1-c1ncccc1Cl] | B | ND |

TABLE 1-continued
| Structure | PKM2_AC50 | Ex-Vivo_AC50 |
|---|---|---|
| 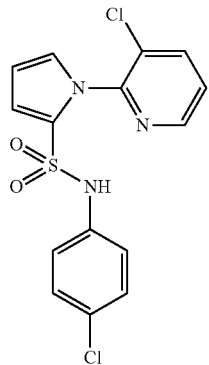 [SMILES: O=S(=O)(Nc1ccc(Cl)cc1)c1cccn1-c1ncccc1Cl] | B | ND |
| 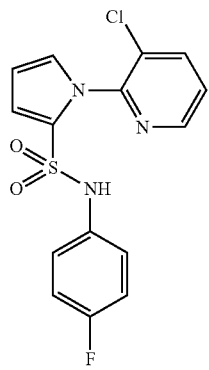 [SMILES: O=S(=O)(Nc1ccc(F)cc1)c1cccn1-c1ncccc1Cl] | D | ND |
| 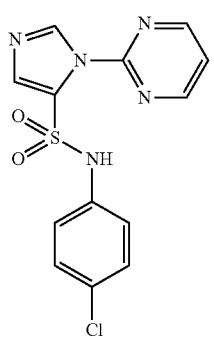 | D | ND |
| 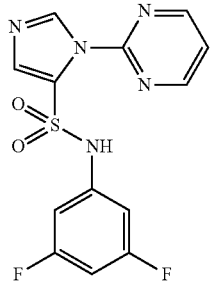 [SMILES: O=S(=O)(Nc1cc(F)cc(F)c1)c1cncn1-c1ncccn1] | D | ND |
TABLE 1-continued
| Structure | PKM2_AC50 | Ex-Vivo_AC50 |
|---|---|---|
| 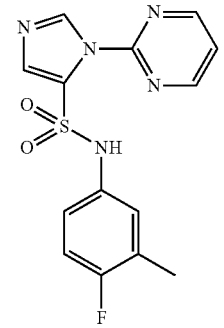 [SMILES: Cc1cc(NS(=O)(=O)c2cncn2-c2ncccn2)ccc1F] | B | + |
| 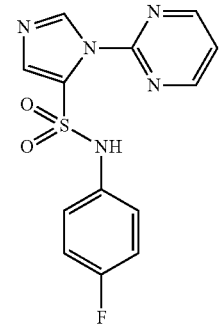 [SMILES: O=S(=O)(Nc1ccc(F)cc1)c1cncn1-c1ncccn1] | D | ND |
| 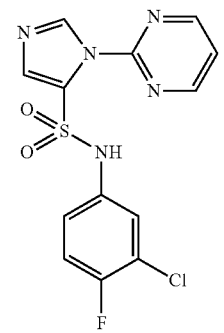 [SMILES: O=S(=O)(Nc1ccc(F)c(Cl)c1)c1cncn1-c1ncccn1] | B | + |
| 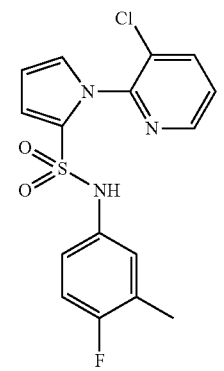 [SMILES: Cc1cc(NS(=O)(=O)c2cccn2-c2ncccc2Cl)ccc1F] | B | + |

TABLE 1-continued

| Structure | PKM2_AC50 | Vivo_AC50 |
|---|---|---|
| (3-Cl-pyridin-2-yl-pyrrole sulfonamide with 3,5-difluorophenyl) | A | ND |
| (3-Cl-5-CF3-pyridin-2-yl-imidazole sulfonamide with quinolin-6-yl) | D | ND |
| (3-Cl-5-CF3-pyridin-2-yl-imidazole sulfonamide with quinolin-5-yl) | D | ND |
| (pyrazin-2-yl-imidazole sulfonamide with 4-fluoro-3-methylphenyl) | B | ND |

TABLE 1-continued

| Structure | PKM2_AC50 | Vivo_AC50 |
|---|---|---|
| (pyrazin-2-yl-imidazole sulfonamide with 3-chloro-4-fluorophenyl) | B | ND |
| (pyrimidin-2-yl-imidazole sulfonamide with benzo[1,3]dioxol-5-yl) | C | ND |
| (2-Cl-pyrimidin-4-yl-imidazole sulfonamide with 4-chlorophenyl) | D | ND |
| (2-Cl-pyrimidin-4-yl-pyrrole sulfonamide with 3-MeO-5-CF3-phenyl) | C | ND |

TABLE 1-continued

| Structure | PKM2_AC50 | Ex-Vivo_AC50 |
|---|---|---|
| (2-chloropyrimidin-4-yl pyrrole sulfonamide with 3,4,5-trifluorophenyl) | D | ND |
| (2-chloropyrimidin-4-yl pyrrole sulfonamide with 3-chloro-4-fluorophenyl) | A | ++ |
| (4-chloropyrimidin-2-yl pyrrole sulfonamide with 3-chloro-4-fluorophenyl) | B | ND |
| (4-chloropyrimidin-2-yl pyrrole sulfonamide with benzo[1,3]dioxol-5-yl) | B | ND |
| (imidazol-1-yl pyrazine sulfonamide with 4-chlorophenyl) | D | + |
| (imidazol-1-yl pyrazine sulfonamide with benzo[1,3]dioxol-5-yl) | B | ND |
| (2-chloropyrimidin-4-yl pyrrole sulfonamide with 3,5-difluorophenyl) | C | ND |
| (2-chloropyrimidin-4-yl pyrrole sulfonamide with 3-trifluoromethylphenyl) | C | ND |

TABLE 1-continued
| Structure | PKM2_AC50 | Ex-Vivo_AC50 |
|---|---|---|
| 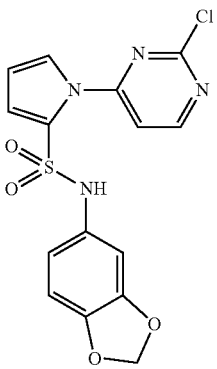 [SMILES: O=S(=O)(Nc1ccc2c(c1)OCO2)c1cccn1-c1ccnc(Cl)n1] | A | ND |
| 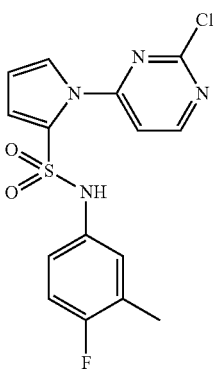 [SMILES: Cc1cc(NS(=O)(=O)c2cccn2-c2ccnc(Cl)n2)ccc1F] | A | ND |
| 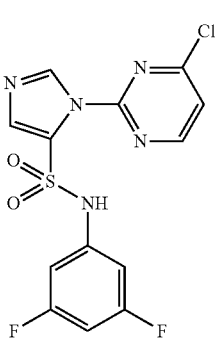 [SMILES: O=S(=O)(Nc1cc(F)cc(F)c1)c1cncn1-c1nccc(Cl)n1] | D | ND |
| 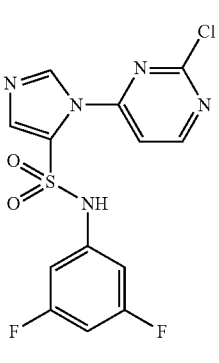 [SMILES: O=S(=O)(Nc1cc(F)cc(F)c1)c1cncn1-c1ccnc(Cl)n1] | E | ND |
TABLE 1-continued
| Structure | PKM2_AC50 | Ex-Vivo_AC50 |
|---|---|---|
| 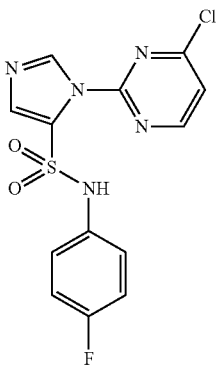 [SMILES: O=S(=O)(Nc1ccc(F)cc1)c1cncn1-c1nccc(Cl)n1] | D | ND |
| 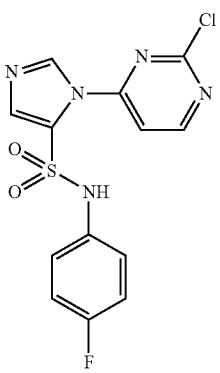 [SMILES: O=S(=O)(Nc1ccc(F)cc1)c1cncn1-c1ccnc(Cl)n1] | D | ND |
| 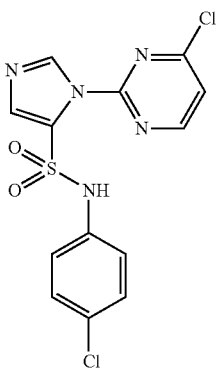 [SMILES: O=S(=O)(Nc1ccc(Cl)cc1)c1cncn1-c1nccc(Cl)n1] | D | ND |
| 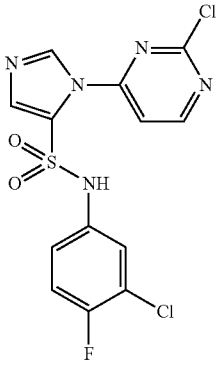 [SMILES: O=S(=O)(Nc1ccc(F)c(Cl)c1)c1cncn1-c1ccnc(Cl)n1] | B | ND |

TABLE 1-continued
| Structure | PKM2_AC50 | Ex-Vivo_AC50 |
|---|---|---|
| 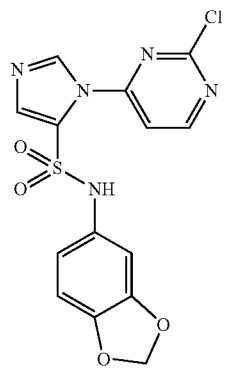 [SMILES: O=S(=O)(Nc1ccc2c(c1)OCO2)c1cncn1-c1ccnc(Cl)n1] | C | ND |
| 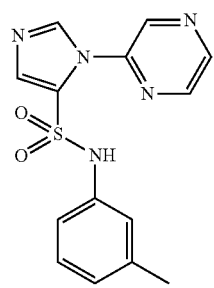 [SMILES: Cc1cccc(NS(=O)(=O)c2cncn2-c2cnccn2)c1] | B | ND |
| | A | ND |
| | C | ND |
TABLE 1-continued
| Structure | PKM2_AC50 | Ex-Vivo_AC50 |
|---|---|---|
| 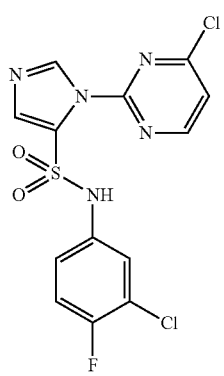 [SMILES: O=S(=O)(Nc1ccc(F)c(Cl)c1)c1cncn1-c1nccc(Cl)n1] | D | ND |
| 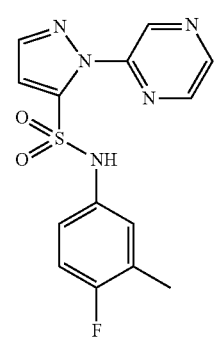 [SMILES: Cc1cc(NS(=O)(=O)c2ccnn2-c2cnccn2)ccc1F] | B | ND |
| | B | ND |
| | A | ND |

TABLE 1-continued

| Structure | PKM2_AC50 | Ex-Vivo_AC50 |
|---|---|---|
| (pyrazole-thiazole sulfonamide, 3-Cl phenyl) | D | ND |
| (pyrazole-thiazole sulfonamide, 4-F-3-methyl phenyl) | D | ND |
| (pyrazole-thiazole sulfonamide, 3-Cl-4-F phenyl) | D | ND |
| (pyrazole-thiophene sulfonamide, 3-Cl phenyl) | E | ND |
| (pyrazole-thiophene sulfonamide, 4-F-3-methyl phenyl) | D | ND |

TABLE 1-continued

| Structure | PKM2_AC50 | Ex-Vivo_AC50 |
|---|---|---|
| (pyrazole-thiophene sulfonamide, 3-Cl-4-F phenyl) | E | ND |
| (imidazole-thiazole sulfonamide, 3-Cl-4-F phenyl) | C | ND |
| (imidazole-thiophene sulfonamide, 3-Cl phenyl) | D | ND |
| (imidazole-thiophene sulfonamide, 3-Cl phenyl) | D | ND |
| (imidazole-thiophene sulfonamide, 4-F-3-methyl phenyl) | D | ND |

TABLE 1-continued

| Structure | PKM2_AC50 | Ex-Vivo_AC50 |
|---|---|---|
| (imidazole-thiophene-sulfonamide-chloro-fluorophenyl) | D | ND |
| (imidazole-thiazole-sulfonamide-chlorophenyl) | C | ND |
| (imidazole-thiazole-sulfonamide-methyl-fluorophenyl) | B | ND |

The compounds described herein can be made using a variety of synthetic techniques. Scheme 1 below depicts a representative synthesis of certain compounds described herein.

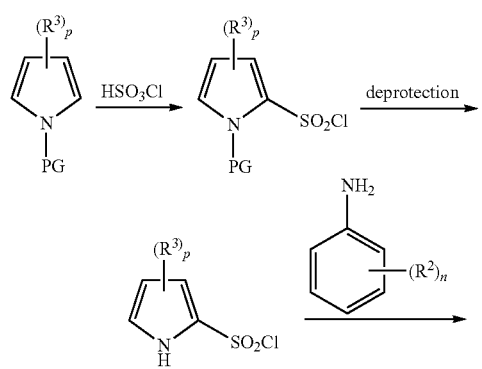

Scheme 1.

PG = protecting group
LG = leaving group
R¹, R², R³, m, n, and p = as defined herein As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention including hydrates and other solvates.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds of this invention may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio.*, (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Methods of Evaluating Compounds

The compounds described herein can be evaluated for ability to modulate PKM2 (e.g., activate or inhibit PKM2) by methods known in the art. Exemplary methods include contacting the compound with a cell-based assay which allows assessment of the ability to modulate (e.g., activate or inhibit) PKM2. E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate or inhibit PKM2). The evaluation could also include measuring a change in pyruvate or a determination of an alteration in mitochondrial membrane potential, e.g., as measured by fluorescent potentiometric dyes.

PKM1 and PKM2 for use in the screening method may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., *E. coli*) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

The activity of the PKM enzyme measured in the screening assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 2.

TABLE 2

| Component of Reaction Condition | Amount in Inhibition Assay | Amount in Activation Assay |
|---|---|---|
| ADP | 0.1-5.0 mM | 0.1-5.0 mM |
| Phosphoenolpyruvate | 0.1-5.0 mM | 0.1-5.0 mM |
| NADH | 10-1000 µM | 10-1000 µM |
| Lactate dehydrogenase | 0.1-10 units | 0.1-10 units |
| Fructose-1,6-bisphosphate | 1-500 µM | 0 |
| DTT | 0.1-50 mM | 0.1-50 mM |
| Brij 35 | 0.01-1% | 0.01-1% |
| Glycerol | 0.1-10% | 0.1-10% |
| Pyruvate Kinase M2 (used for screen) | 1-100 pg | 1-100 pg |
| DMSO | 1-10% | 1-10% |

Candidate inhibitory compounds are chosen if they demonstrate specificity for PKM2 and inhibition of the PKM2 enzyme greater than 10, 15, 20, 25, 30, 35, 40, 45, 50, 55, 60, 65, 70, 75, 80, 85, 90, 95, 99, or 99.9%.

Candidate activator compounds are chosen if they demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, specific candidate activators of PKM2 can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Exemplary screening assays also include ex vivo assays, for example, an ex vivo assay described herein.

Methods of Treatment

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Cancer Combination Therapies

In some embodiments, a compound described herein is administered together with an additional cancer treatment. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclindepdendent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary anbitodies include Ctuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g. a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can modulate PKM2. Accordingly, a patient and/or subject can be selected for treatment using a compound described herein by first evaluating the patient and/or subject to determine whether the subject is in need of modulation of PKM2, and if the subject is determined to be in need of modulation of PKM2, then optionally administering to the subject a compound described herein.

A subject can be evaluated as being in need of modulation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor). In some embodiments, the patient is evaluated using a radiological assay or evaluation of hemolytic parameters.

EXAMPLES

Example 1

PKM2 Assay

Procedure:
PKM2 stock enzyme solution was diluted in Reaction Buffer
2 µL of compound was added into each well first, and then 180 µL of the Reaction Mix was added.
Reaction mixture with compound (without ADP) were incubated for 30 minutes at 4° C.
Plates were re-equilibrated to room temperature prior to adding 20 µL ADP to initiate the reaction.
Reaction progress was measured as changes in absorbance at 340 nm wavelength at room temperature (25° C.)
Reaction Mix: PKM2 (50 ng/well), ADP (0.7 mM), PEP (0.15 mM), NADH (180 µM), LDH (2 units) in Reaction Buffer
Reaction Buffer: 100 mM KCl, 50 mM Tris pH 7.5, 5 mM MgCl2, 1 mM DTT, 0.03% BSA.

Example 2

PKM2 Ex-Vivo Assay

Described herein is a method to measure the activity of PKM2 activators in living cells and tissue. One of ordinary skill in the art would recognize and understand that this method can be adapted to high throughput format, and can accommodate a variety of cell lines and growth conditions.

In the assay, cells are treated with a compound described herein (i.e., a PKM2 activator). This compound is capable of entering the cell and binding to PKM2, inducing an activated conformation. The excess unbound compound is washed away with PBS, and the cells are lysed by snap-freezing on dry ice, followed by addition of a detergent-containing lysis buffer. The lysate, in which activated PKM2 remains intact, is removed and added to a chemical cocktail including the chemicals necessary to measure pyruvate kinase activity, in an assay that is coupled to the LDHa enzyme. The amount of pyruvate kinase activity that is measured is normalized to the total protein content in the lysate, and related to the concentration of PKM2 activator that was added to the cell. This allows an $AC_{50}$ (concentration at which PKM2 is activated 50%) value to be derived. The total fold-increase in activity over mock-treated cells can also be calculated, and the "maximum level of activation" can be used to distinguish between compounds that fully activate PKM2 and compounds that can only partially activate PKM2.

In the case of measuring PKM2 activity from tissue (for example, in a cell tumor), animals harboring the tissue/tumor of interest are dosed with a compound. After a specified period of time in which exposure has been achieved in the target tissue/tumor of interest, the tissue/tumor is harvested from the animal, snap-frozen, and then lysed and homogenized. The amount of pyruvate kinase activity in this lysate can then be quantitated as described above.

Materials:
Lysis buffer*
20 mM Tris-HCl (pH 7.5)
150 mM NaCl
1 mM $Na_2EDTA$
1 mM EGTA 1% Triton
2.5 mM sodium pyrophosphate
1 mM beta-glycerophosphate
1 mM $Na_3VO_4$
1 μg/ml leupeptin
1 mM PMSF**
* This lysis buffer (without PMSF) is available from Cell Signaling Technology as a 10× stock (#9803)
** 1 mM PMSF is added fresh from a 100 mM stock solution made up in isopropanol. The stock solution can be stored at 4 degrees indefinitely.

Pyruvate Kinase Assay Master Mix (Same for PKM2 Activator Assay):

TABLE 3

| KCl | 100 mM |
|---|---|
| Tris (pH 7.5) | 50 mM |
| $MgCl_2$ | 5.0 mM |
| $PEP$ | 0.10 mM |
| NADH | 0.18 mM |
| DTT | 1.00 mM |
| BSA | 0.3 mg/mL |
| LDH | 0.5 units |
| $H_2O$ | to 180 uL |

ADP Solution:

| ADP | 7.0 mM |
|---|---|
| $H_2O$ | to 20 uL |

Procedure:

On the first day (day 1) cells are normally cultured in RPMI-1640 (Lonza #12-115° F.) (with 25 mM Hepes, L-glutamine)/10% FBS. The cells are subsequently trypsinized and plated in RPMI-1640 (Lonza, #12-918F) (no phenol red, supplemented with L-glutamine @300 mg/L (Sigma, #G8540))/10% FBS at the following densities in 96 well plates:

A549: 40k/well 100 uL final volume of media per well.

On the second day (Day 2), the cells should be 70-90% confluent. The cells are then treated with a compound described herein dissolved in media at final assay concentrations in a 96-well assay block (500 uL) (Costar, #3956). The final DMSO concentration is 0.1% (0.5 μL into 500 uL). Compound dilutions in DMSO are prepared so that the final DMSO concentration is constant at all compound concentrations. The media for the assay is RPMI-1640 (no phenol red, with L-glutamine @300 mg/L).

The media is then aspirated carefully from the cells using a multi-channel aspirator. 100 μL of media w/compounds is added onto cells with a multichannel pipette. Each compound concentration is then assayed in triplicate (a duplicate assay is also sufficient).

The cells are treated for 1-4 hrs (this time is determined empirically compared to DMSO reference treatment). During the cell treatment, PBS (containing calcium and magnesium) and lysis buffer is cooled on ice.

The cells are lysed and the pyruvate kinase activity is assayed. The remaining media is aspirated and the cells are washed 2× with 100 uL ice-cold PBS. The PBS is removed, and the cell plate frozen on dry ice for 5 minutes. The cells are lysed in 50 μL cold lysis buffer. Cells are subsequently kept on ice for 5 minutes, and then agitated on a plate shaker for 5 minutes (repeat 3×). Remove 10 μL for protein quantitation (or use $OD_{280}$ on entire plate).

In a fresh plate, 170 uL of pyruvate kinase assay master mix was added to each well (see end for recipe). 10 uL of cell lysate was then transferred into each well. The assay was initiated upon addition of 20 uL of ADP solution. The rates were then calculated against the initial rates to determine pyruvate kinase specific activity.

The concentration and type of detergent in the lysis buffer can be varied to accommodate the specific physicochemical properties of the specific PKM2 activator. For instance, the interaction between some PKM2 activators and PKM2 can be disrupted by higher detergent concentrations, but preserved when cells are lysed with lower detergent concentrations.

Example 3

Compounds and Synthesis

Scheme 1:

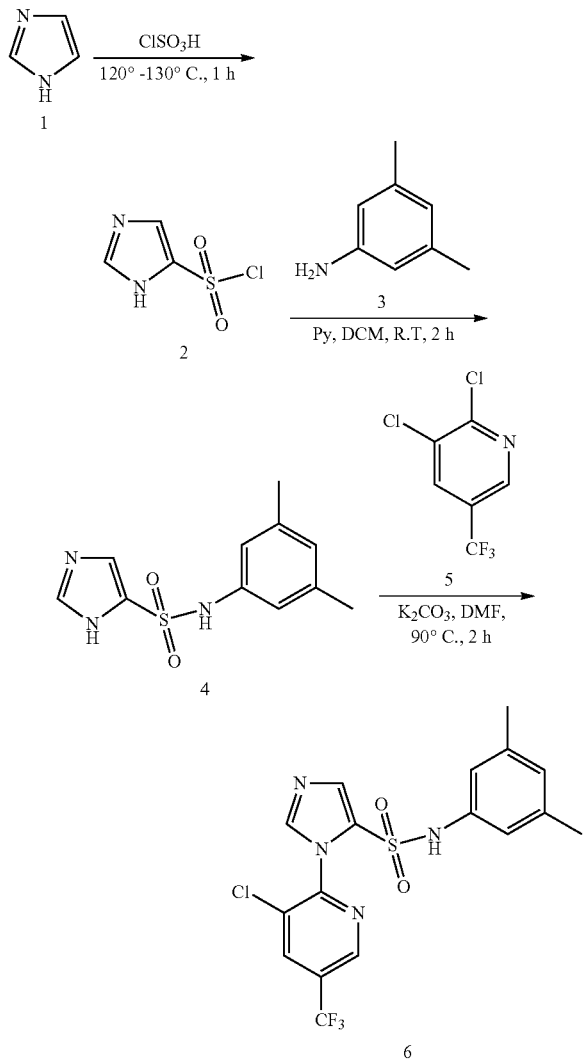

General Procedure for Compound 2: Chlorosulfonic acid (24 mL) was added slowly over a period of 15 min to imidazole (4.0 g, 58.82 mmol) at 0° C. The resulting mixture was heated at 120-130° C. for 3 h. After completion of SM, the reaction mixture was quenched with ice cold water (25 mL) and extracted with DCM (3×40 mL). The combined organic layers were dried over Na₂SO₄ and concentrated under reduced pressure. The desired Compound-2 was obtained as a solid (3.0 g, 42% yield).

¹H NMR (500 MHz, DMSO-d₆) δ: 14.29 (bs, 1H), 8.90 (s, 1H), 7.64 (s, 1H); Mass (M+1): 166.9.

General Procedure for Compound 4: To a solution of compound-3 (500 mg, 4.13 mmol) in DCM (10 mL) under a nitrogen atmosphere, pyridine (0.65 ml, 8.26 mmol) was added and stirred at room temperature for 15 min. The reaction mixture was then cooled to 0° C. followed by the dropwise addition of Compound-2 (820 mg, 4.96 mmol) in DCM (4 mL). The resulting reaction mixture was stirred for 2 h at room temperature. After completion of the reaction, 0.5N HCl solution was added and extracted with DCM (2×10 mL). The combined organic layers were washed with brine (1×20 mL), dried over Na₂SO₄ and concentrated under reduced pressure to provide the desired compound 4 as a solid (500 mg, 50% yield).

General Procedure for Compound 6: In a two neck RB flask, compound-4 (50 mg, 0.2 mmoL), compound-5 (51 mg, 0.24 mmoL) and K₂CO₃ (54 mg, 0.4 mmoL) were charged in DMF (6 mL) under N₂ atmosphere. The resulting reaction mixture was stirred at 90° C. for 3 h. The progress of the reaction was monitored by TLC. After completion of SM, the reaction mixture was quenched with water (15 mL) and extracted with ethyl acetate (2×20 mL). The combined organic layers were dried over Na₂SO₄ and concentrated under reduced pressure. The crude product was purified by column chromatography (Silica gel 60-120, 3:7, ethyl acetate/hexane) to obtain the desired compound-6 as a solid (40 mg, 47% yield).

¹H NMR (500 MHz, DMSO-D6) δ: 10.29 (s, 1H), 9.03 (s, 1H), 8.84 (s, 1H), 8.37 (s, 1H), 8.32 (s, 1H), 7.82 (s, 2H), 6.63 (s, 1H), 2.18 (s, 6H); HPLC Purity: 93.13%; Mass (M+1): 431.1.

1-(3-chloro-5-(trifluromethyl)pyridine-2-yl)-N-(3,5-dimethylphenyl)-1H-imidazole-5-sulfonamide

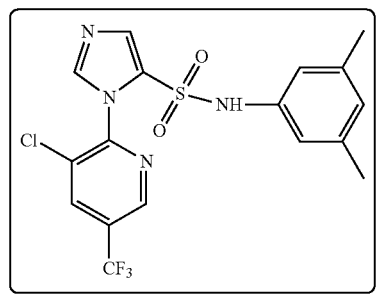 [SMILES: Cc1cc(C)cc(NS(=O)(=O)c2cncn2-c2ncc(C(F)(F)F)cc2Cl)c1]

¹H NMR (500 MHz, DMSO-d₆) δ: 10.29 (s, 1H), 9.03 (s, 1H), 8.84 (s, 1H), 8.37 (s, 1H), 8.32 (s, 1H), 7.82 (s, 2H), 6.63 (s, 1H), 2.18 (s, 6H); HPLC Purity: 93.13%; Mass (M+1): 431.1.

1-(3-chloro-5-(trifluromethyl)pyridine-2-yl)-N-(4-methoxyphenyl)-1H-imidazole-5-sulfonamide

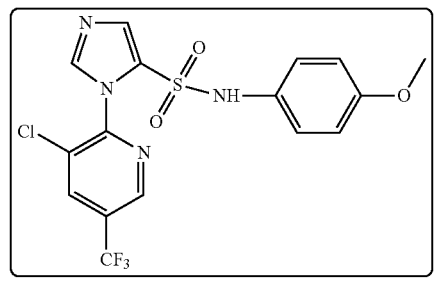 [SMILES: COc1ccc(NS(=O)(=O)c2cncn2-c2ncc(C(F)(F)F)cc2Cl)cc1]

¹H NMR (500 MHz, DMSO-d₆) δ: 10.04 (bs, 1H), 9.01 (s, 1H), 8.83 (s, 1H), 8.38 (s, 1H), 8.18 (s, 1H), 7.08 (d, 2H), 6.82 (d, 2H), 3.67 (s, 3H); HPLC Purity: 91.04%; Mass (M+1): 433.

N-(4-methoxyphenyl)-1-5-(trifluromethyl)pyridine-2-yl)-1H-imidazole-5-sulfonamide

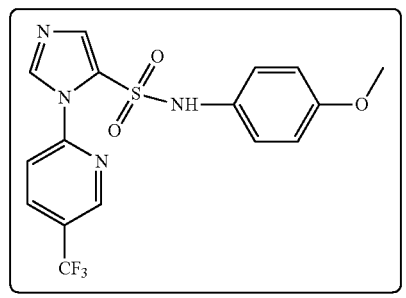 [SMILES: COc1ccc(NS(=O)(=O)c2cncn2-c2ccc(C(F)(F)F)cn2)cc1]

¹H NMR (500 MHz, DMSO-d₆) δ: 10.11 (s, 1H), 8.97 (s, 1H), 8.81 (s, 1H), 8.52 (m, 2H), 8.19 (d, 1H), 7.48 (d, 2H), 6.82 (d, 2H), 3.65 (s, 3H); HPLC Purity: 96.12%; Mass (M+1): 399.

N-(2,3-dihydrobenzo[b][1,4]dioxin-6-yl)-1-5-(trifluromethyl)pyridine-2-yl)-1H-imidazole-5-sulfonamide

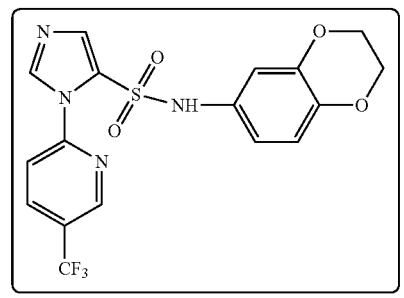 [SMILES: O=S(=O)(Nc1ccc2c(c1)OCCO2)c1cncn1-c1ccc(C(F)(F)F)cn1]

¹H NMR (500 MHz, DMSO-d₆) δ: 10.53 (s, 1H), 8.96 (s, 1H), 8.79 (s, 1H), 8.58 (s, 1H), 8.56 (s, 1H), 8.18 (d, 1H), 6.66 (s, 2H), 6.63 (d, 1H) 4.17 (t, 4H); HPLC Purity: 98.48%; Mass (M+1): 427.

89

1-(3-chloro-5-(trifluromethyl)pyridin-2-yl)-N-(2,3-dihydrobenzo[b][1,4]dioxin-6-yl)-1H-imidazole-5-sulfonamide

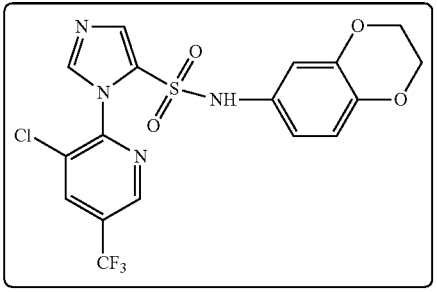 [SMILES: O=S(=O)(Nc1ccc2c(c1)OCCO2)c1cncn1-c1ncc(C(F)(F)F)cc1Cl]

$^1$H NMR (500 MHz, DMSO-d$_6$) δ: 10.13 (s, 1H), 9.02 (s, 1H), 8.84 (s, 1H), 8.39 (s, 1H), 8.22 (s, 1H), 6.78-6.58 (m, 3H), 4.18 (s, 4H); HPLC Purity: 96.98%; Mass (M+1): 461.

N-(4-flurophenyl)-1-(5-(trifluromethyl)pyridine-2-yl)-1H-imidazole-5-sulfonamide

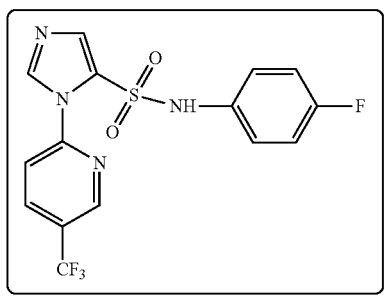 [SMILES: O=S(=O)(Nc1ccc(F)cc1)c1cncn1-c1ccc(C(F)(F)F)cn1]

$^1$H NMR (500 MHz, DMSO-d$_6$) δ: 10.42 (s, 1H), 8.97 (s, 1H), 8.80 (s, 1H), 8.62 (s, 1H), 8.46 (d, 1H), 8.19 (d, 1H), 7.23 (d, 2H), 7.08 (d, 2H); HPLC Purity: 99.35%; Mass (M+1): 387.

1-(3-chloro-5-(trifluromethyl)pyridin-2-yl)-N-(4-flurophenyl)-1H-imidazole-5-sulfonamide

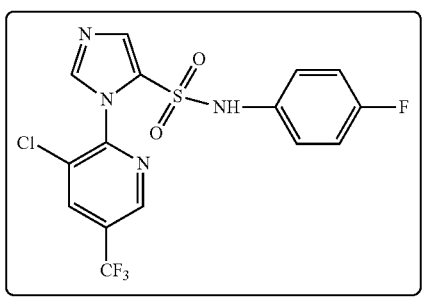 [SMILES: O=S(=O)(Nc1ccc(F)cc1)c1cncn1-c1ncc(C(F)(F)F)cc1Cl]

$^1$H NMR (500 MHz, DMSO-d$_6$) δ: 10.42 (s, 1H), 9.02 (s, 1H), 8.84 (s, 1H), 8.39 (s, 1H), 8.24 (s, 1H), 7.22 (d, 2H), 7.08 (d, 2H); HPLC Purity: 92.78%; Mass (M+1): 421.

90

N-(3,5-dimethylphenyl)-1-(5-(trifluromethyl)pyridine-2-yl)-1H-imidazole-5-sulfonamide

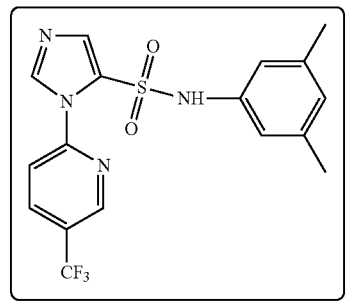 [SMILES: Cc1cc(C)cc(NS(=O)(=O)c2cncn2-c2ccc(C(F)(F)F)cn2)c1]

$^1$H NMR (500 MHz, DMSO-d$_6$) δ: 10.28 (s, 1H), 8.96 (s, 1H), 8.78 (s, 1H), 8.63 (s, 1H), 8.33 (d, 1H), 8.19 (d, 1H), 7.82 (s, 2H), 7.62 (s, 1H), 2.18 (s, 6H); HPLC Purity: 99.23%; Mass (M+1): 397.1.

1-(3-chloro-5-(trifluromethyl)pyridin-2-yl)-N-(3,5-dimethoxyphenyl)-1H-imidazole-5-sulfonamide

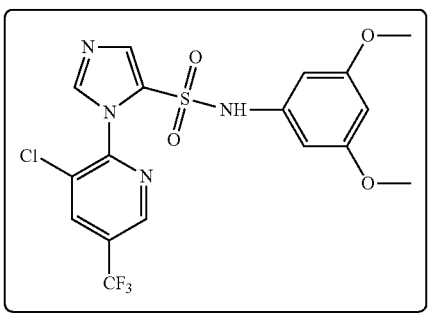 [SMILES: COc1cc(NS(=O)(=O)c2cncn2-c2ncc(C(F)(F)F)cc2Cl)cc(OC)c1]

$^1$H NMR (500 MHz, DMSO-d$_6$) δ: 10.41 (s, 1H), 9.02 (s, 1H), 8.87 (s, 1H), 8.38 (s, 2H), 6.39 (s, 2H), 6.17 (s, 1H), 3.67 (s, 6H); HPLC Purity: 97.82%; Mass (M+1): 463.1.

N-(4-chloro-3-methylphenyl)-1-(3-chloro-(5-(trifluromethyl)pyridine-2-yl)-1H-imidazole-5-sulfonamide

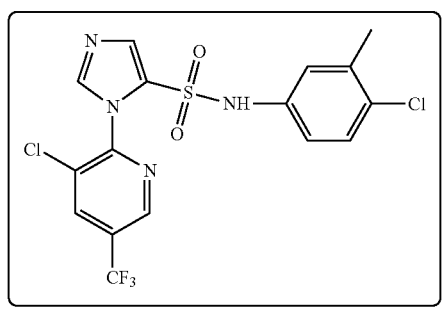 [SMILES: Cc1cc(NS(=O)(=O)c2cncn2-c2ncc(C(F)(F)F)cc2Cl)ccc1Cl]

$^1$H NMR (500 MHz, DMSO-d$_6$) δ: 10.53 (s, 1H), 9.03 (s, 1H), 8.84 (s, 1H), 8.37 (d, 2H), 7.28 (d, 1H), 7.16 (s, 1H), 7.03 (d, 1H), 2.22 (s, 3H); HPLC Purity: 98.76%; Mass (M+1): 451.

91

1-(3-chloro-5-(trifluromethyl)pyridin-2-yl)-N-(3,4-dimethylphenyl)-1H-imidazole-5-sulfonamide

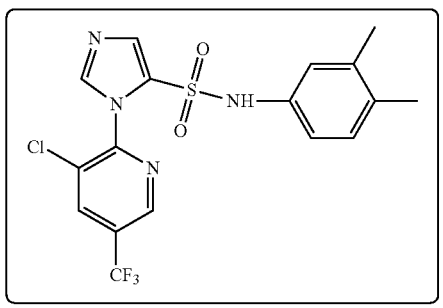 [SMILES: Cc1ccc(NS(=O)(=O)c2cncn2-c2ncc(C(F)(F)F)cc2Cl)cc1C]

$^1$H NMR (500 MHz, DMSO-d$_6$) δ: 10.21 (s, 1H), 9.02 (s, 1H), 8.85 (s, 1H), 8.38 (s, 2H), 8.24 (s, 1H), 6.98-6.87 (m, 3H), 2.13 (s, 6H); HPLC Purity: 99.06%; Mass (M+1): 431.

1-(3-chloro-5-(trifluromethyl)pyridin-2-yl)-N-(3-chlorophenyl)-1H-imidazole-5-sulfonamide

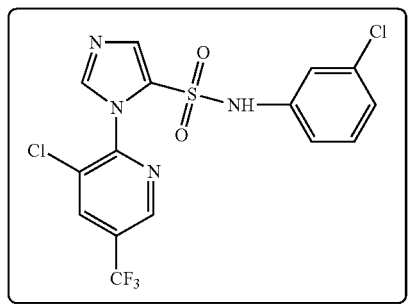 [SMILES: O=S(=O)(Nc1cccc(Cl)c1)c1cncn1-c1ncc(C(F)(F)F)cc1Cl]

$^1$H NMR (500 MHz, DMSO-d$_6$) δ: 10.78 (s, 1H), 9.03 (s, 1H), 8.84 (s, 1H), 8.38 (d, 2H), 7.31-7.24 (m, 2H), 7.16 (d, 1H), 7.08 (d, 1H); HPLC Purity: 95.26%; Mass (M+1): 436.9.

1-(3-chloro-5-(trifluromethyl)pyridin-2-yl)-N-(3-(trifluromethyl)phenyl)-1H-imidazole-5-sulfonamide

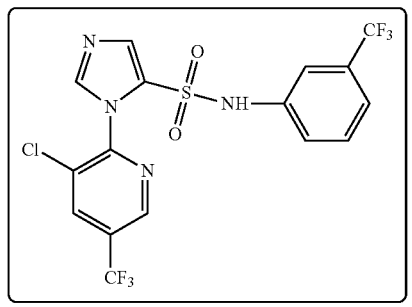 [SMILES: O=S(=O)(Nc1cccc(C(F)(F)F)c1)c1cncn1-c1ncc(C(F)(F)F)cc1Cl]

$^1$H NMR (500 MHz, DMSO-d$_6$) δ: 10.96 (s, 1H), 9.02 (s, 1H), 8.87 (s, 1H), 8.38 (d, 2H), 7.52-7.38 (m, 4H); HPLC Purity: 90.31%; Mass (M+1): 471.1.

92

1-(3-chloro-5-(trifluromethyl)pyridin-2-yl)-N-(3,5-dichlorophenyl)-1H-imidazole-5-sulfonamide

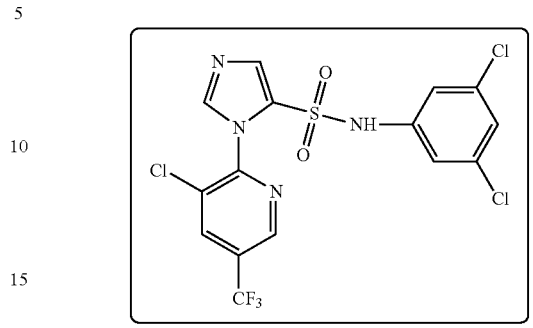

$^1$H NMR (500 MHz, DMSO-d$_6$) δ: 11.03 (s, 1H), 9.03 (s, 1H), 8.49 (s, 1H), 8.39 (s, 1H), 7.24-7.21 (m, 4H); HPLC Purity: 97.52%; Mass (M+1): 472.8.

1-(3-chloro-5-(trifluromethyl)pyridin-2-yl)-N-(3-ethylphenyl)-1H-imidazole-5-sulfonamide

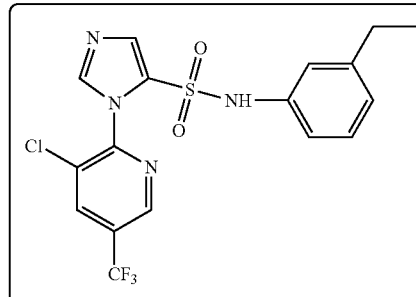

$^1$H NMR (500 MHz, DMSO-d$_6$) δ: 10.38 (s, 1H), 9.02 (s, 1H), 8.84 (s, 1H), 8.37 (d, 2H), 7.17 (m, 1H), 7.01 (m, 2H), 6.86 (d, 1H), 2.52 (q, 2H), 1.13 (t, 3H); HPLC Purity: 93.13%; Mass (M+1): 431.1.

1-(3-chloro-5-(trifluromethyl)pyridin-2-yl)-N-(3-cyanophenyl)-1H-imidazole-5-sulfonamide

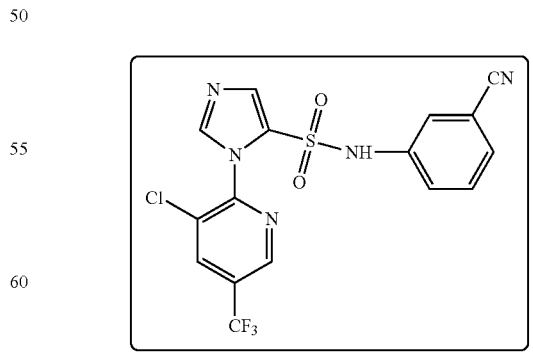

$^1$H NMR (500 MHz, DMSO-d$_6$) δ: 10.99 (s, 1H), 9.04 (s, 1H), 8.87 (s, 1H), 8.44 (s, 1H), 8.38 (s, 1H), 7.51 (m, 4H); HPLC Purity: 90.19%; Mass (M+1): 428.1.

Scheme 2:

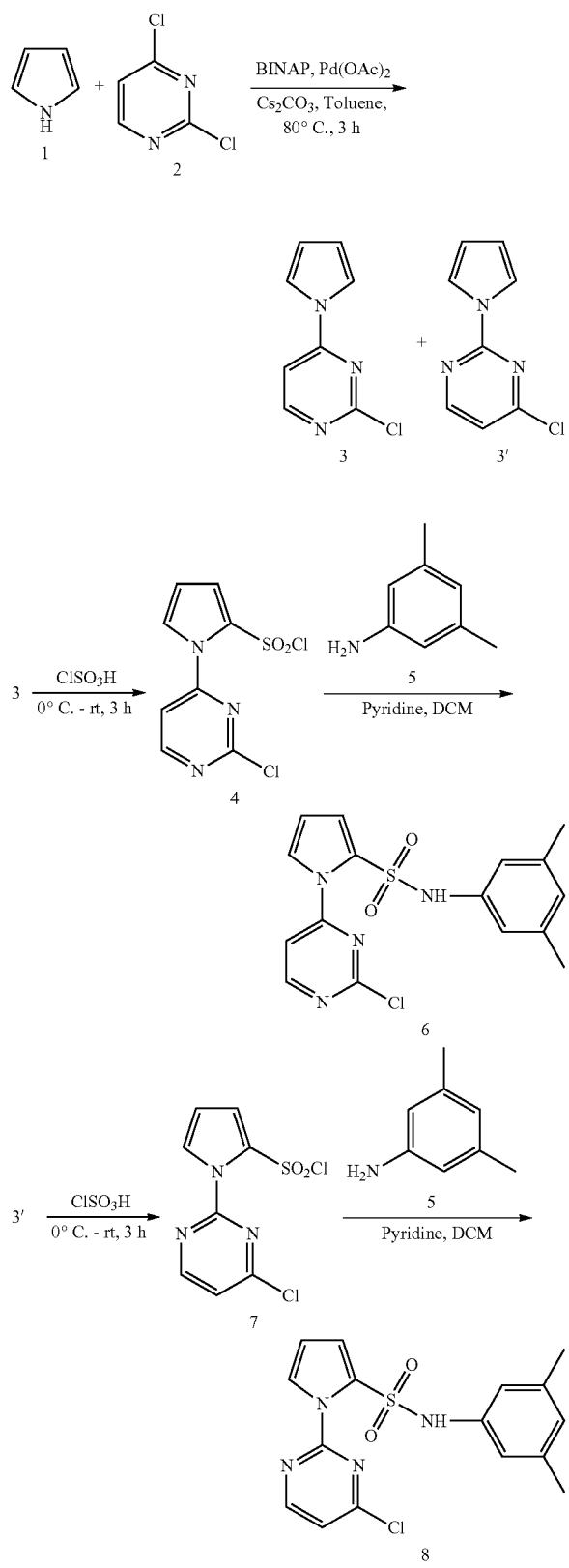

General Procedure for Compound 3&3': In a two neck RB flask, compound-2 (3.0 g, 0.02 mole), pyrrole (2.69 g, 0.04 mole) and Cs$_2$CO$_3$ (19.68 g, 0.06 mole) were charged in toluene (60 mL) under N$_2$ atmosphere. BINAP (620 mg, 0.00099 mole) and Pd(OAc)$_2$ (990 mg, 0.004 mole) were then added to the reaction mixture under N$_2$ atmosphere and stirred at 80° C. for 3 h. The progress of the reaction was monitored by TLC. After completion of SM, the reaction mixture was filtered through celite and quenched with water (5 mL). The organic layer was separated, dried over Na$_2$SO$_4$ and concentrated under reduced pressure. The crude product was subjected to silica gel column chromatography (silica gel 60-120, 1:9, ethyl acetate/hexane) to separate the sulfonyl chlorides 3 & 3' as viscous oil (compound-3: 1.1 g 30.55% and compound-3': 684 mg 19.0%). Overall 49.55% yield obtained.

$^1$H NMR (500 MHz, DMSO-d$_6$) δ: 8.53 (d, 1H), 7.54 (d, 2H), 7.15 (d, 1H), 6.41 (d, 2H); Mass (M+1): 180.

General Procedure for Compound 4: In a single neck RB flask, to compound-3 (100 mg, 0.59 mmol) was added chlorosulfonic acid (690 mg, 5.9 mmol) slowly over a period of 15 min at 0° C. The resulting mixture was stirred for 3 h at room temperature. After completion of SM, the reaction mixture was quenched with water (3 mL) and extracted with DCM (2×5 mL). The combined organic layers were dried over Na$_2$SO$_4$ and concentrated under reduced pressure. The crude compound was washed with pentane and dried under vacuum to provide the desired compound-4 as a solid (60 mg, 38.7%).

General Procedure for Compound 6: In a two neck RB flask, compound-5 (9.5 mg, 0.16 mmol) and pyridine (0.15 mL) were taken and stirred for 10 minutes at 0° C. Compound-4 (30 mg, 0.1 mmol) was then added at 0° C. and the resulting mixture was stirred for 3 h at room temperature. After completion of the reaction, HCl solution (6N, 4 mL) was added and extracted with DCM (2×5 mL). The combined organic layers were washed with brine (1×20 mL), dried over anhydrous Na$_2$SO$_4$ and concentrated under reduced pressure. The crude product was purified by column chromatography (silica gel 60-120, 2:8, ethyl acetate/hexane) to provide the desired compound-6 as a solid (20.4 mg, 68.1%).

$^1$H NMR (500 MHz, DMSO-d$_6$) δ: 8.81 (s, 1H), 8.19 (s, 1H), 7.97 (s, 1H), 7.81 (s, 1H), 6.81 (s, 2H), 6.69 (s, 1H), 6.58 (s, 1H), 2.19 (s, 6H); HPLC Purity: 92.07%; Mass (M+1): 362.9.

General Procedure for Compound 7: In a single neck RB flask, to compound-3' (100 mg, 0.59 mmol) was added chlorosulfonic acid (690 mg, 5.9 mmol) over a period of 15 min at 0° C. The resulting mixture was then stirred for 3 h at room temperature. Upon completion of SM (as indicated by TLC), the reaction mixture was quenched with water (3 mL) and extracted with DCM (2×5 mL). The combined organic layers were dried over Na$_2$SO$_4$ and concentrated under reduced pressure. The crude compound was washed with pentane and dried under vacuum to provide the desired compound-7 as a solid (35 mg, 22% yield).

General Procedure for Compound 8: In a two neck RB flask, compound-5 (14.9 mg, 0.12 mmol) and pyridine (0.1 mL) were transferred and stirred for 10 minutes at 0° C. Compound-7 (20 mg, 0.08 mmol) was then added at 0° C. The resulting mixture was stirred for 3 h at room temperature. After completion of the reaction, HCl (6N, 4 mL) was added and extracted with DCM (2×5 mL). The combined organic layers were washed with brine (1×20 mL), dried over Na$_2$SO$_4$ and concentrated under reduced pressure. The crude product was purified by column chromatography (silica gel 60-120, 2:8, ethyl acetate/hexane) to provide the desired compound-8 as a solid (18.62 mg, 71% yield).

$^1$H NMR (500 MHz, DMSO-d$_6$) δ: 10.0 (s, 1H), 8.81 (s, 1H), 8.01 (s, 1H), 7.78 (s, 1H), 7.63 (s, 1H), 6.82 (s, 2H), 6.68 (s, 1H), 6.54 (s, 1H), 2.19 (s, 6H); HPLC Purity: 98.01%; Mass (M+1): 363.

1-(4-chloropyrimidin-2-yl)-N-(3,5-dimethylphenyl)-1H-pyrrole-2-sulfonamide

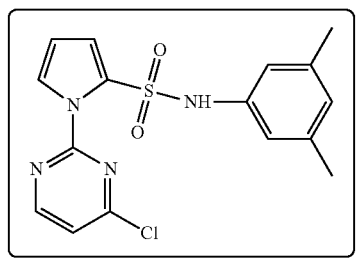 [SMILES: Cc1cc(C)cc(NS(=O)(=O)c2cccn2-c2nccc(Cl)n2)c1]

$^1$H NMR (500 MHz, DMSO-d$_6$) δ: 10.0 (s, 1H), 8.81 (s, 1H), 8.01 (s, 1H), 7.78 (s, 1H), 7.63 (s, 1H), 6.82 (s, 2H), 6.68 (s, 1H), 6.54 (s, 1H), 2.19 (s, 6H); HPLC Purity: 98.01%; Mass (M+1): 363.

1-(2-chloropyrimidin-4-yl)-N-(3,5-dimethylphenyl)-1H-pyrrole-2-sulfonamide

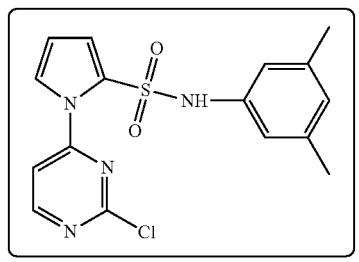 [SMILES: Cc1cc(C)cc(NS(=O)(=O)c2cccn2-c2ccnc(Cl)n2)c1]

$^1$H NMR (500 MHz, DMSO-d$_6$) δ: 8.81 (s, 1H), 8.19 (s, 1H), 7.97 (s, 1H), 7.81 (s, 1H), 6.81 (s, 2H), 6.69 (s, 1H), 6.58 (s, 1H), 2.19 (s, 6H); HPLC Purity: 92.07%; Mass (M+1): 362.9.

N-(4-chlorophenyl)-1-(2-chloropyrimidin-2-yl)-1H-pyrrole-2-sulfonamide

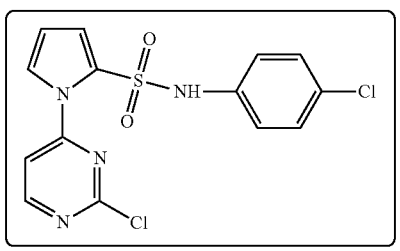 [SMILES: O=S(=O)(Nc1ccc(Cl)cc1)c1cccn1-c1ccnc(Cl)n1]

$^1$H NMR (500 MHz, DMSO-d$_6$) δ: 10.34 (s, 1H), 8.82 (s, 1H), 8.23 (s, 1H), 8.07 (s, 1H), 7.37 (d, 2H), 7.08 (d, 2H), 6.57 (s, 1H); HPLC Purity: 96.74%; Mass (M+1): 369.

N-(4-chlorophenyl)-1-(4-chloropyrimidin-2-yl)-1H-pyrrole-2-sulfonamide

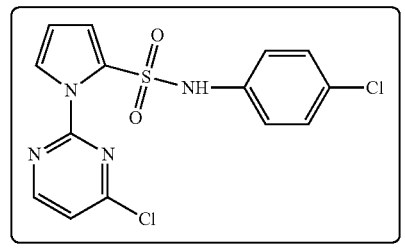 [SMILES: O=S(=O)(Nc1ccc(Cl)cc1)c1cccn1-c1nccc(Cl)n1]

$^1$H NMR (500 MHz, DMSO-d$_6$) δ: 10.29 (s, 1H), 8.90 (s, 1H), 8.02 (s, 1H), 7.77 (s, 1H), 7.64 (s, 1H), 7.33 (d, 2H), 7.18 (d, 2H), 6.54 (s, 1H); HPLC Purity: 91.17%; Mass (M+1): 368.9.

N-(4-chlorophenyl)-1-(pyrimidin-2-yl)-1H-pyrrole-2-sulfonamide

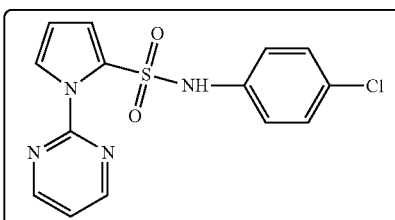

$^1$H NMR (500 MHz, DMSO-d$_6$) δ: 10.27 (s, 1H), 8.83 (d, 2H), 8.07 (s, 1H), 7.79 (s, 1H), 7.48 (d, 1H), 7.32 (d, 2H), 7.18 (d, 2H), 6.53 (s, 1H); HPLC Purity: 97.05%; Mass (M+1): 334.9.

N-(3,5-dimethylphenyl)-1-(pyrimidin-2-yl)-1H-pyrrole-2-sulfonamide

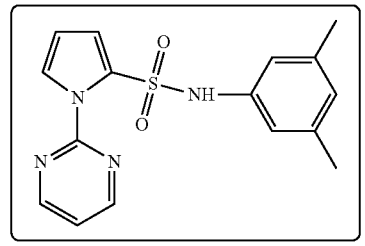 [SMILES: Cc1cc(C)cc(NS(=O)(=O)c2cccn2-c2ncccn2)c1]

$^1$H NMR (500 MHz, DMSO-d$_6$) δ: 9.88 (s, 1H), 8.84 (d, 2H), 8.04 (s, 1H), 7.78 (s, 1H), 7.43 (d, 1H), 6.79 (s, 2H), 6.63 (s, 1H), 6.49 (s, 1H); HPLC Purity: 97.48%; Mass (M+1): 329.

Scheme 3.

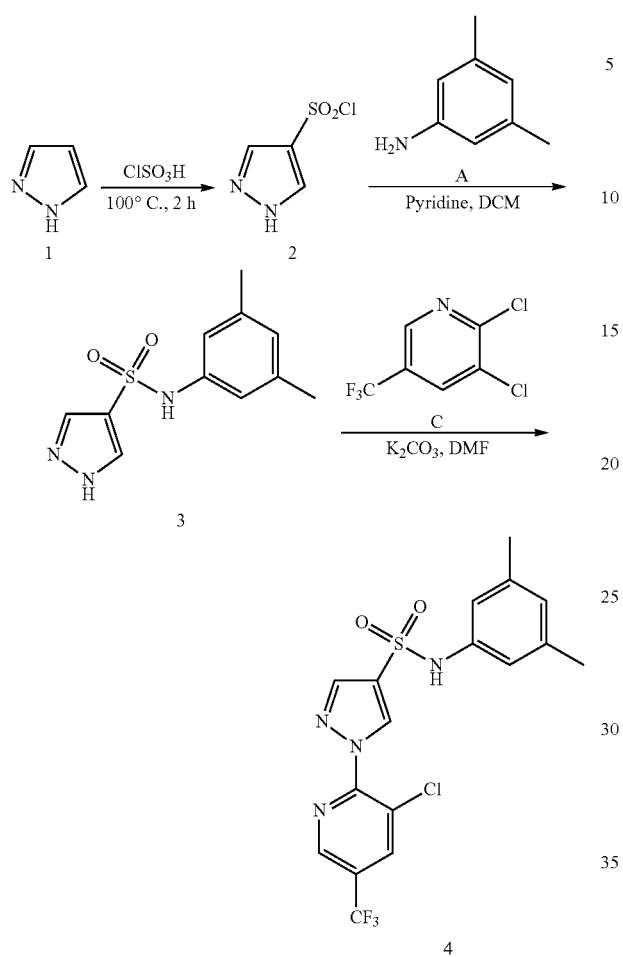

General Procedure for Compound 2: In a single neck RB flask chlorosulfonic acid (9.7 ml, 145 mmol) was added slowly over a period of 15 minutes to pyrazole (2.0 g, 29.0 mmol) at 0° C. The resulting mixture was then heated at 100° C. for 3 h. Upon completion, the reaction mixture was quenched with ice cold water (25 mL) and extracted with DCM (3×40 mL). The combined organic layers were dried over $Na_2SO_4$ and concentrated under reduced pressure. The desired product 2 was obtained as a solid (4.8 g, 63% yield).

$^1$H NMR (500 MHz, CDCl3) δ: 8.19 (s, 2H).

General Procedure for Compound 3: To a stirred solution of compound-2 (60 mg, 0.496 mmol) in DCM (10 mL) under a nitrogen atmosphere, pyridine was added (0.1 mL, 0.99 mmol) and stirred at room temperature for 15 minutes. The reaction mixture was then cooled to 0° C. followed by the dropwise addition of compound-2 solution (91.1 mg, 0.545 mmol in 4 mL of DCM). The resulting mixture was stirred for 2 h at room temperature. After completion of the reaction, 0.5N HCl solution was added and extracted with DCM (2×10 mL). The combined organic layers were washed with brine (1×20 mL), dried over $Na_2SO_4$ and concentrated under reduced pressure to furnish the desired compound-4 as a solid (120 mg, 97% yield).

$^1$H NMR (500 MHz, CDCl$_3$) δ: 10.4 (bs, 1H), 7.81 (s, 2H), 6.79 (s, 1H), 6.72 (s, 2H), 6.47 (s, 1H), 2.23 (s, 6H); Mass (M+1): 252.

General Procedure for Compound 4: In a two neck RB flask, compound-3 (50 mg, 0.2 mmol), compound-C (0.03 ml, 0.29 mmol) and $K_2CO_3$ (83 mg, 0.6 mmol) were charged in DMF (5 mL) under $N_2$ atmosphere and stirred at 90° C. for 3 h. The progress of the reaction was monitored by TLC. After completion of SM, the reaction mixture was quenched with water (15 mL) and extracted with ethyl acetate (2×20 mL). The combined organic layers were dried over $Na_2SO_4$ and concentrated under reduced pressure. The crude product was purified by column chromatography (Silica gel 60-120, 3:7, ethyl acetate/hexane) to give the desired product 4 as a solid (70 mg, 81.3% yield).

1-(3-chloro-5-(trifluromethyl)pyridin-2-yl)-N-(3,5-dimethylphenyl)-1H-pyrazole-4-sulfonamide

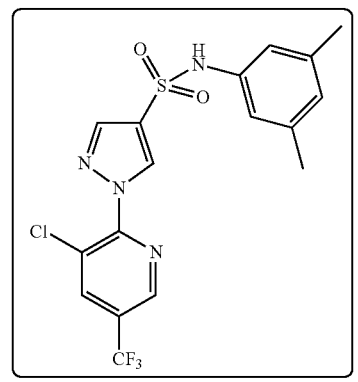 [SMILES: Cc1cc(C)cc(NS(=O)(=O)c2cnn(-c3ncc(C(F)(F)F)cc3Cl)c2)c1]

$^1$H NMR (500 MHz, DMSO-d$_6$) δ: 10.10 (s, 1H), 9.01 (s, 1H), 8.82 (s, 1H), 8.75 (s, 1H), 8.15 (s, 1H), 6.81 (s, 2H), 6.77 (s, 1H), 2.19 (s, 6H); HPLC Purity: 94.73%; Mass (M+1): 431.1.

N-(4-methoxyphenyl)-1-(5-(trifluromethyl)pyridin-2-yl)-1H-pyrazole-4-sulfonamide

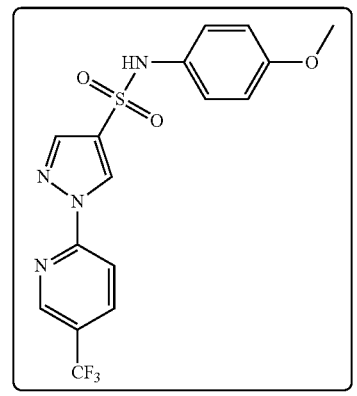 [SMILES: COc1ccc(NS(=O)(=O)c2cnn(-c3ccc(C(F)(F)F)cn3)c2)cc1]

$^1$H NMR (500 MHz, DMSO-d$_6$) δ: 9.98 (s, 1H), 8.97 (s, 1H), 8.81 (s, 1H), 8.45 (d, 1H), 8.10 (d, 1H), 8.05 (s, 1H), 7.07 (d, 2H), 6.85 (d, 2H), 3.68 (s, 3H); HPLC Purity: 99.35%.

N-(4-chlorophenyl)-1-(5-(trifluromethyl)pyridin-2-yl)-1H-pyrazole-4-sulfonamide

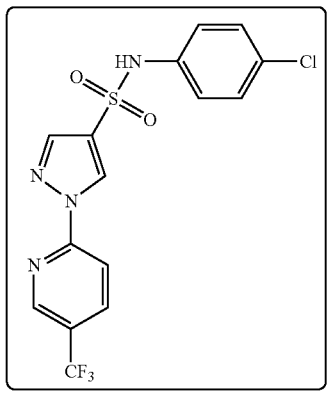 [SMILES: O=S(=O)(Nc1ccc(Cl)cc1)c1cnn(-c2ccc(C(F)(F)F)cn2)c1]

¹H NMR (500 MHz, DMSO-d₆) δ: 10.51 (s, 1H), 8.97 (s, 2H), 8.46 (d, 1H), 8.18 (s, 1H), 8.12 (d, 1H), 7.38 (d, 2H), 7.21 (d, 2H); HPLC Purity: 99.60%; Mass (M+1): 403.

1-(3-chloro-5-(trifluromethyl)pyridin-2-yl)-N-(4-chlorophenyl)-1H-pyrazole-4-sulfonamide

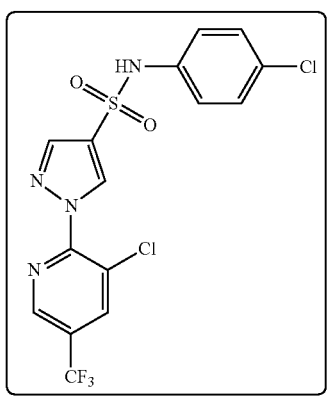 [SMILES: O=S(=O)(Nc1ccc(Cl)cc1)c1cnn(-c2ncc(C(F)(F)F)cc2Cl)c1]

¹H NMR (500 MHz, DMSO-d₆) δ: 10.49 (s, 1H), 9.01 (s, 1H), 8.83 (s, 1H), 8.78 (s, 1H), 8.13 (s, 1H), 7.38 (d, 2H), 7.19 (d, 2H); HPLC Purity: 99.52%; Mass (M+1): 437.

1-(3-chloro-5-(trifluromethyl)pyridin-2-yl)-N-(4-methoxyphenyl)-1H-pyrazole-4-sulfonamide

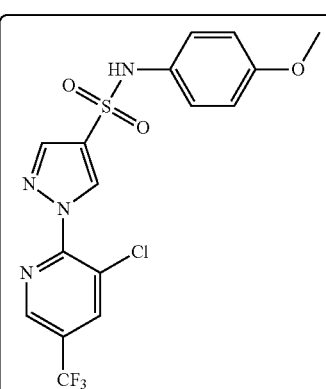

¹H NMR (500 MHz, DMSO-d₆) δ: 9.98 (s, 1H), 9.01 (s, 1H), 8.81 (s, 1H), 8.64 (s, 1H), 8.02 (s, 1H), 7.07 (d, 2H), 6.84 (d, 2H), 3.68 (s, 3H); HPLC Purity: 99.35%; Mass (M+1): 432.9.

Scheme 4.

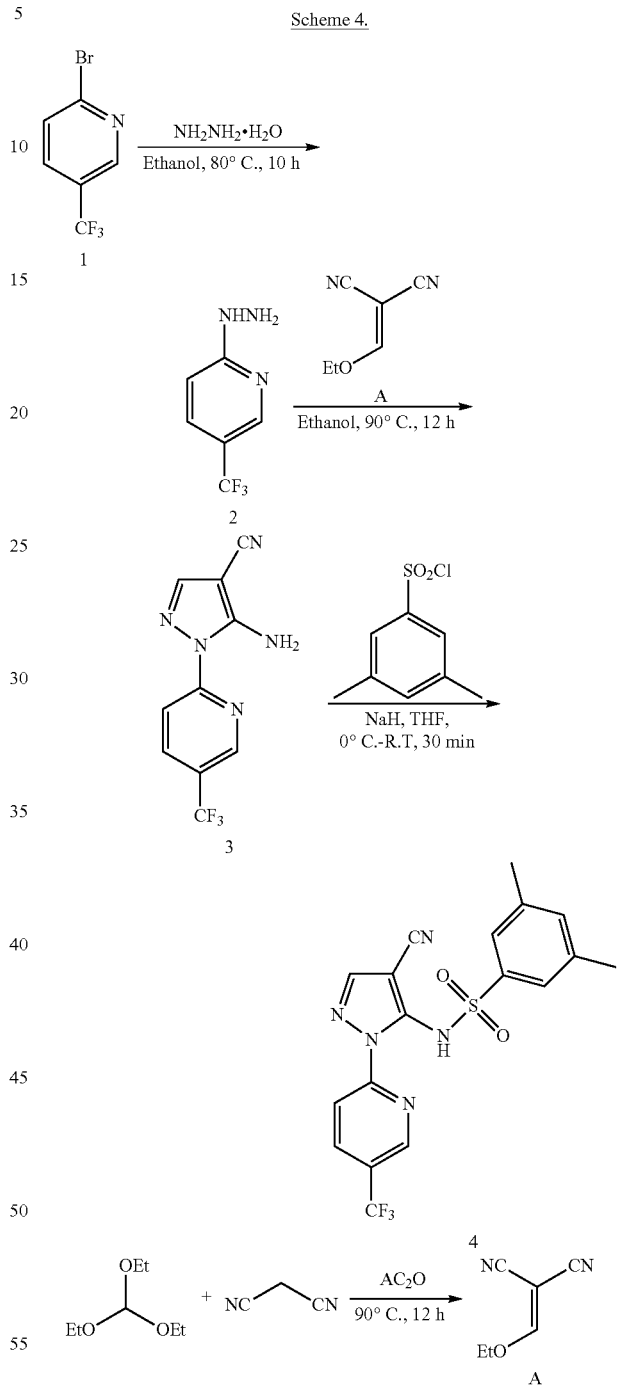

General Procedure for Preparation of Compound A: A solution of mixture of triethyl orthoformate (11.2 g, 75 mmol) and malononitrile (5.0 g, 75 mmol) in acetic anhydride (15 mL) was heated to 90° C. for 12 h. After completion of reaction (TLC shows absent of S.M), the solvent (excess acetic anhydride and acetic acid) was removed under high vacuum. The residue (6.0 g, 65.2% of yield) was used in the next reaction without further purification.

¹H NMR (500 MHz, DMSO-d6) δ: 8.59 (s, 1H), 4.55 (m, 2H), 1.38 (m, 3H).

General Procedure for Compound 2: To a stirred solution of 2-bromo-5-(trifluoromethyl)pyridine (compound-1) (1.0 g, 4.0 mmol) in ethanol (5 mL), hydrazine hydrate (980 mg, 20 mmol) was added at room temperature and the reaction mixture was heated to 90° C. for 12 h. After completion of reaction (TLC shows absent of S.M), the solvent was removed under high vacuum. The residue was treated with water (30 mL) and extracted with ethyl acetate (2×50 mL). The organic layer was washed with brine (50 mL), dried over sodium sulfate, filtered and concentrated to provide the desired compound-2 as a brown color solid. (700 mg, 90% yield).

$^1$H NMR (500 MHz, DMSO-d$_6$) δ: 8.42 (d, 2H), 8.25 (s, 1H), 5.0 (bs, 3H); Mass (M+1): 178.

General Procedure for Compound 3: A solution of 2-hydrazinyl-5-(trifluoromethyl)pyridine (compound-2) (250 mg, 1.4 mmol) and 2-(ethoxymethylene)malononitrile (compound-A) (170 mg, 1.4 mmol) in ethanol (10 mL) was heated to 90° C. for 12 h. After completion of reaction (TLC shows absent of S.M), the solvent was removed under high vacuum. The residue was treated with water (30 mL) and extracted with ethyl acetate (2×50 mL). The organic layer was washed with brine (50 mL), dried over sodium sulphate, filtered and concentrated to provide the desired compound-3 as an off white color solid. (280 mg, 80% yield).

$^1$H NMR (500 MHz, DMSO-d$_6$) δ: 8.91 (s, 1H), 8.45 (d, 1H), 8.32 (s, 2H), 8.15 (d, 1H), 8.0 (s, 1H); Mass (M+1): 254.

General Procedure for Compound 4: In a two neck RB flask, compound-3 (50 mg, 0.1 mmoL) was taken in THF (4 mL) and cooled to 0° C. under nitrogen atmosphere. NaH (60% NaH, 5 mg, 0.1 mmol) was added to the reaction mixture and stirred for 10 min followed by the addition of solution of 3,5-dimethylbenzene-1-sulphonyl chloride (44 mg, 0.2 mmoL) in THF (2 mL) at 0° C. The reaction mixture was then stirred for 30 min. at room temperature. After completion of the reaction, the reaction mixture was quenched with ice cold water and extracted with ethyl acetate, and the organic layer was washed with brine (10 mL), dried over sodium sulphate, filtered and concentrated to provide the desired compound-4 as a solid (60 mg, 81.2% yield).

$^1$H NMR (500 MHz, DMSO-d$_6$) δ: 8.83 (s, 1H), 8.28 (d, 1H), 8.17 (d, 1H), 7.77 (s, 1H), 7.31 (s, 2H), 7.01 (s, 1H), 2.21 (s, 6H); HPLC Purity: 98.81%; Mass (M+1): 422.

N-(4-cyano-1-(5-(trifluromethyl)pyridin-2-yl)-1H-pyrazole-3,5 dimethylbenzenesulfonamide

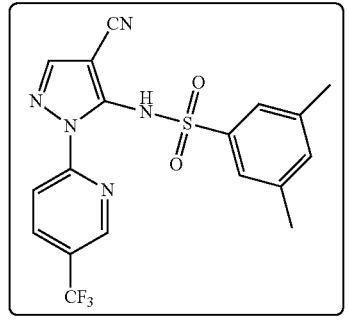 [SMILES: Cc1cc(C)cc(S(=O)(=O)Nc2c(C#N)cnn2-c2ccc(C(F)(F)F)cn2)c1]

$^1$H NMR (500 MHz, DMSO-d$_6$) δ: 8.83 (s, 1H), 8.28 (d, 1H), 8.17 (d, 1H), 7.77 (s, 1H), 7.31 (s, 2H), 7.01 (s, 1H), 2.21 (s, 6H); HPLC Purity: 98.81%; Mass (M+1): 422.

4-chloro-N-(4-cyano-1-(5-(trifluromethyl)pyridin-2-yl)-1H-pyrazol-5-yl) benzenesulfonamide

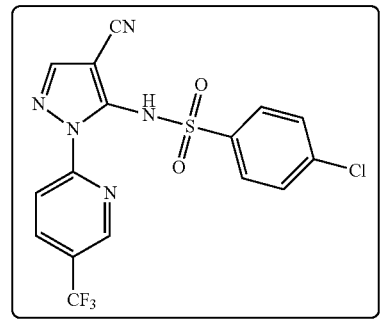 [SMILES: N#Cc1cnn(-c2ccc(C(F)(F)F)cn2)c1NS(=O)(=O)c1ccc(Cl)cc1]

$^1$H NMR (500 MHz, DMSO-d$_6$) δ: 8.88 (s, 1H), 8.31 (d, 1H), 8.14 (bs, 1H), 7.73 (m, 3H), 7.41 (m, 2H); HPLC Purity: 97.80%; Mass (M+1): 428.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

We claim:

1. A compound of Formula (IV) or a pharmaceutically acceptable salt thereof, wherein:

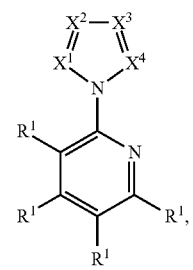

(IV)

$X^1$ is N or CE;
$X^2$ is N or CD;
$X^3$ is N or CB;
$X^4$ is N or CA, wherein at least one of $X^1$, $X^2$, $X^3$ and $X^4$ is N; and at least one of $X^1$, $X^2$, $X^3$, $X^4$, is C—SO$_2$—NR$^4$R$^5$;
A, B, D and E are each independently selected from H and —SO$_2$—NR$^4$R$^5$;
each $R^4$ is independently selected from C$_{1-8}$ alkyl, aryl and heteroaryl, each of which is substituted with n occurrences of $R^2$;
n is 0, 1, 2 or 3;
each $R^5$ is independently hydrogen or C$_{1-8}$ alkyl;
each $R^1$ is independently selected from hydrogen, C$_{1-8}$ alkoxy, halogen, haloalkyl and haloalkoxy;
each $R^2$ is independently selected from halo, haloalkyl, C$_{1-4}$alkyl, C$_{2-4}$ alkenyl, C$_{2-4}$ alkynylheteroaryl, aryl, aralkyl, heteroaralkyl, cyano, —OR$^a$, —COOR$^b$ and —CONR$^c$R$^{c'}$; wherein two R$^2$, together with the carbons to which they are attached, may form an optionally substituted ring, each of which can be further substituted;

R$^a$ is independently selected from alkyl, haloalkyl, optionally substituted heteroaryl and optionally substituted heterocyclyl;

each R$^b$ is independently alkyl;

each R$^c$ is independently selected from hydrogen and alkyl; and each R$^{c'}$ is independently alkyl.

2. The compound of claim 1 or a pharmaceutically acceptable salt thereof, wherein at least one of X$^3$ and X$^4$ are CH.

3. The compound of claim 1 or a pharmaceutically acceptable salt thereof, wherein at least one of A, B, D and E are H.

4. The compound of claim 1 or a pharmaceutically acceptable salt thereof, wherein B is —SO$_2$—NH—R$^4$.

5. The compound of claim 1 or a pharmaceutically acceptable salt thereof having Formula (IVa):

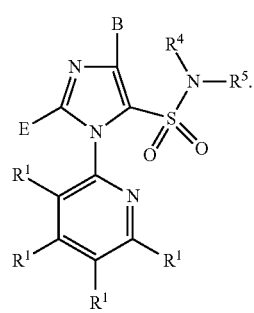

(IVa)

6. The compound of claim 1 or a pharmaceutically acceptable salt thereof having Formula (IVb):

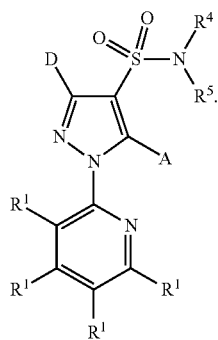

(IVb)

7. The compound of claim 1 or a pharmaceutically acceptable salt thereof, wherein each R$^1$ is independently selected from halogen or haloalkyl.

8. The compound of claim 1 or a pharmaceutically acceptable salt thereof, wherein each R$^1$ is independently selected from chlorine and trifluoroalkyl.

9. The compound of claim 1 or a pharmaceutically acceptable salt thereof, wherein R$^4$ is aryl substituted with n occurrences of R$^2$.

10. The compound of claim 1 or a pharmaceutically acceptable salt thereof, wherein R$^2$ is selected from halo, C$_{1-4}$ alkyl, cyano, haloalkyl, —OR$^a$ or two R$^2$, taken together with the carbon atoms to which they are attached form an optionally substituted ring, each of which can be further substituted.

11. The compound of claim 1 or a pharmaceutically acceptable salt thereof, wherein R$^2$ is selected from halo and C$_{1-4}$ alkyl.

12. The compound of claim 1 or a pharmaceutically acceptable salt thereof, wherein n is 2.

13. The compound of claim 1 or a pharmaceutically acceptable salt thereof selected from:

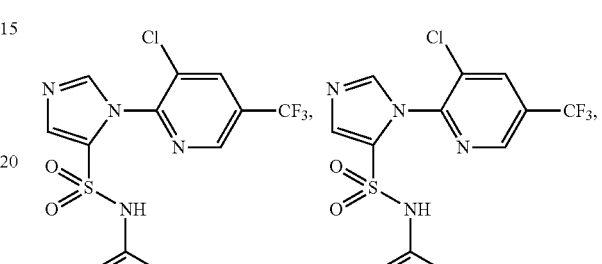

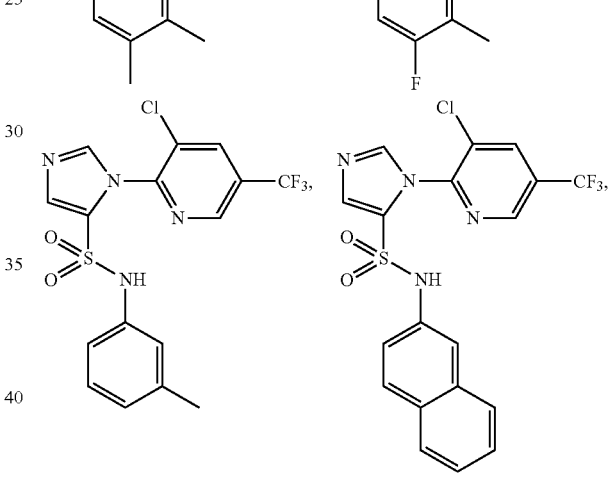

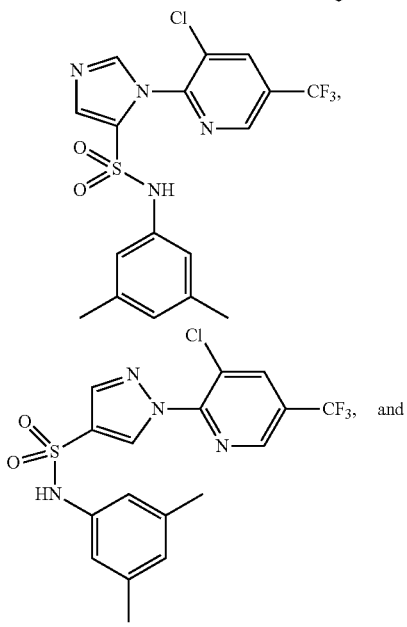

-continued

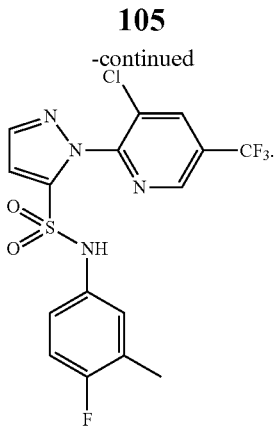

14. A compound of Formula (II) or a pharmaceutically acceptable salt thereof, wherein:

(II)

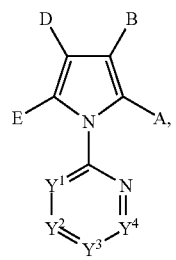

A, B, D and E are each independently selected from H, —$SO_2$—$NR^4R^5$ and $R^3$; wherein at least one of A, B, D, or E is —$SO_2$—$NR^4R^5$;

$Y^1$, $Y^2$, $Y^3$ and $Y^4$ are each independently selected from N and $CR^1$, wherein at least one of $Y^1$, $Y^2$, $Y^3$ and $Y^4$ are N;

each $R^4$ is independently selected from $C_{1-8}$ alkyl, aryl and heteroaryl, each of which is substituted with n occurrences of $R^2$;

each $R^5$ is independently hydrogen or $C_{1-8}$ alkyl;

each $R^1$ is independently selected from hydrogen, $C_{1-8}$ alkyl, $C_{1-8}$ terminal alkynyl, $C_{1-8}$ alkoxy, halogen, haloalkyl and haloalkoxy;

each $R^2$ is independently selected from halo, haloalkyl, $C_{1-4}$ alkyl, $C_{2-4}$ alkenyl, $C_{2-4}$ alkynyl, aryl, heteroaryl, aralkyl, heteroaralkyl, cyano, —$OR^a$, —$COOR^b$ and —$CONR^cR^{c'}$; wherein two $R^2$, together with the carbons to which they are attached, may form an optionally substituted ring, each of which can be further substituted;

each $R^3$ is independently selected from $C_{1-8}$ alkyl, —$OR^a$, halogen, haloalkyl, haloalkoxy and optionally substituted heteroaryl;

each $R^a$ is independently selected from alkyl, haloalkyl, optionally substituted heteroaryl and optionally substituted heterocyclyl;

each $R^b$ is independently alkyl;

each $R^c$ is independently selected from hydrogen and alkyl;

each $R^{c'}$ is independently alkyl; and n is 0, 1, 2 or 3.

15. The compound of claim 14 or a pharmaceutically acceptable salt thereof having Formula (IIa):

(IIa)

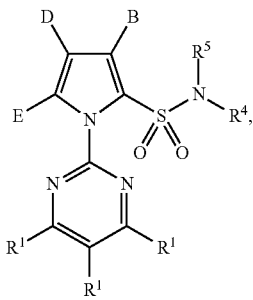

16. The compound of claim 14 or a pharmaceutically acceptable salt thereof having Formula (IIb):

(IIb)

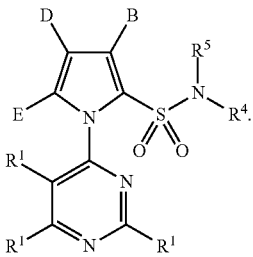

17. The compound of claim 14 or a pharmaceutically acceptable salt thereof, wherein $R^4$ is aryl substituted with n occurrences of $R^2$.

18. The compound of claim 14 or a pharmaceutically acceptable salt thereof, wherein $R^2$ is halo, $C_{1-4}$ alkyl or haloalkyl; or two $R^2$, together with the carbon atoms to which they are attached, form a 5-membered heterocyclic ring.

19. The compound of claim 14 or a pharmaceutically acceptable salt thereof selected from:

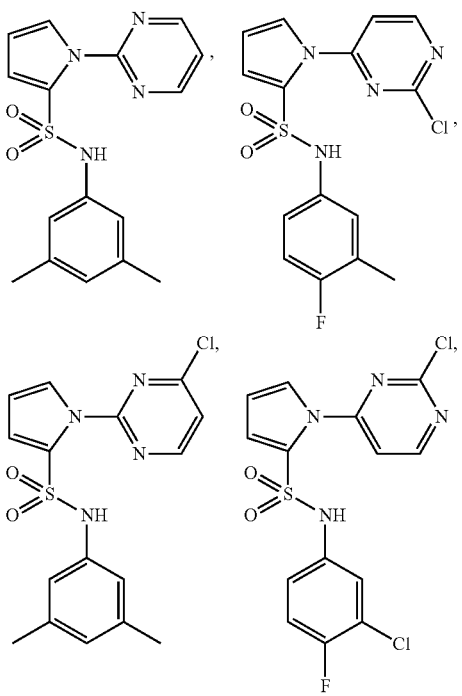

-continued

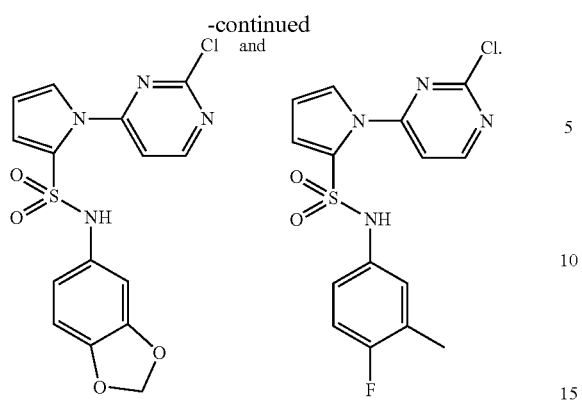

20. A pharmaceutical composition comprising a compound of claim 1 or a pharmaceutically acceptable salt thereof, and a pharmaceutically acceptable carrier.

21. A pharmaceutical composition comprising a compound of claim 14 or a pharmaceutically acceptable salt thereof, and a pharmaceutically acceptable carrier.

22. A method of treating breast cancer, the method of comprising administering to a patient in need thereof a therapeutically effective amount of a compound of claim 1 or a pharmaceutically acceptable salt thereof.

23. A method of treating breast cancer, the method comprising administering to a patient in need thereof a therapeutically effective amount of a compound of claim 14 or a pharmaceutically acceptable salt thereof.

* * * * *

UNITED STATES PATENT AND TRADEMARK OFFICE
CERTIFICATE OF CORRECTION

PATENT NO. : 9,938,259 B2
APPLICATION NO. : 15/488174
DATED : April 10, 2018
INVENTOR(S) : Francesco G. Salituro et al.

Page 1 of 1

It is certified that error appears in the above-identified patent and that said Letters Patent is hereby corrected as shown below:

In the Claims

Claim 19, Column 106, Line 41, delete " 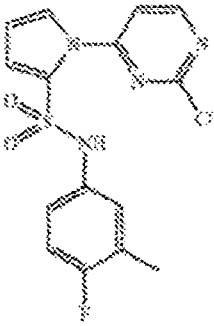 " and replace with

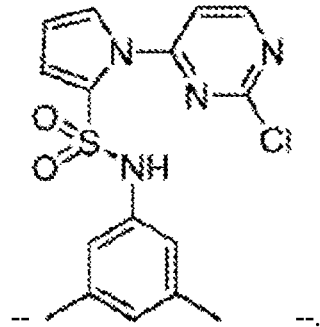 --.

Signed and Sealed this
Tenth Day of July, 2018

Andrei Iancu
*Director of the United States Patent and Trademark Office*